United States Patent [19]
Poss et al.

[11] Patent Number: 5,808,102
[45] Date of Patent: Sep. 15, 1998

[54] PHOSPHORUS BEARING TAXANES INTERMEDIATES

[75] Inventors: Michael A. Poss, Lawrenceville; Jerome L. Moniot, Chester; Ivan D. Trifunovich, Monmouth Junction; David J. Kucera, Warren; John K. Thottahil, Robbinsville, all of N.J.; Shu-Hui Chen, Hamden; Jianmei Wei, East Hartford, both of Conn.

[73] Assignee: Bristol-Myers Squibb Company, Princeton, N.J.

[21] Appl. No.: 916,298

[22] Filed: Aug. 22, 1997

Related U.S. Application Data

[63] Continuation of Ser. No. 600,353, Feb. 12, 1996, which is a continuation of Ser. No. 171,792, Dec. 22, 1993, abandoned, which is a continuation-in-part of Ser. No. 995,443, Dec. 23, 1992, abandoned.

[51] Int. Cl.$^6$ .................................................. C07D 305/14
[52] U.S. Cl. ..................... 549/220; 548/110; 548/237; 549/510; 549/511; 549/473; 549/214
[58] Field of Search ............................................. 549/220

[56] References Cited

U.S. PATENT DOCUMENTS

| | | | |
|---|---|---|---|
| 4,203,900 | 5/1980 | Kaiser | 548/239 |
| 4,303,439 | 12/1981 | Howe et al. | 548/236 |
| 4,354,029 | 10/1982 | Kaiser et al. | 548/239 |
| 4,360,678 | 11/1982 | Howe et al. | 548/236 |
| 4,443,611 | 4/1984 | Kaiser | 548/239 |
| 4,543,414 | 9/1985 | Larson | 548/239 |
| 4,743,700 | 5/1988 | Jommi et al. | 548/216 |
| 4,814,470 | 3/1989 | Colin et al. | 519/510 |
| 4,857,653 | 8/1989 | Colin et al. | 549/510 |
| 4,876,399 | 10/1989 | Holton et al. | 549/510 |
| 4,924,011 | 5/1990 | Denis et al. | 549/510 |
| 4,924,012 | 5/1990 | Colin et al. | 519/510 |
| 5,015,744 | 5/1991 | Holton | 549/510 |
| 5,136,060 | 8/1992 | Holton | 549/510 |
| 5,208,237 | 5/1993 | Hewawasam | 544/361 |
| 5,254,580 | 10/1993 | Chen | 549/510 |
| 5,272,171 | 12/1993 | Ueda | 549/510 |
| 5,420,337 | 5/1995 | Patel et al. | 560/41 |
| 5,476,954 | 12/1995 | Bourzat et al. | 549/510 |
| 5,646,176 | 7/1997 | Golk et al. | 549/220 |

FOREIGN PATENT DOCUMENTS

| | | |
|---|---|---|
| 1061330 | 8/1979 | Canada . |
| 245825 | 11/1987 | European Pat. Off. . |
| 0359516 | 3/1990 | European Pat. Off. . |
| 0400971 | 12/1990 | European Pat. Off. . |
| 0428376 | 5/1991 | European Pat. Off. . |
| 1695918 | 5/1971 | Germany . |
| 2919891 | 12/1980 | Germany . |
| 55-145650 | 11/1980 | Japan . |
| 60-222-416 | 11/1985 | Japan . |
| 61-005-015 | 1/1986 | Japan . |
| 61-115-022 | 6/1986 | Japan . |
| 61-51578 | 11/1986 | Japan . |
| 91-09224 | 5/1992 | South Africa . |
| 90/02738 | 3/1990 | WIPO . |
| WO 92/09589 | 6/1992 | WIPO . |
| 92-09589 | 7/1992 | WIPO . |
| 94-14787 | 7/1994 | WIPO . |

OTHER PUBLICATIONS

Boyd et al.; "Cyclization of Acylaminoalkanols to 2–Oxazolines"; *JACS*, vol. 82, pp. 2032–2034 (1960).

Boyd et al.; "Sulfonic Acid Esters as Alkylating Agents: Formation of 2–Oxazolines"; *JACS*, vol. 75, pp. 5896–5897 (1953).

Bubel et al.; "Reaction of Acetyloxiranes with Acetonitrile", Chem. Heterocycl. Compd. (Engl. Transl.), 18,8, pp. 773–775 (1982).

Cason et al.; "Synthesis in the Peri–Substituted Naphthalene Series", *J. Org. Chem.*, vol. 15, pp. 617–626 (1950).

Commercon et al., "Improved Protection and Esterification of Precursor of the Taxotere® and Taxol Side Chains", Tetrahedron Letters, vol. 33, No. 36, pp. 5185–5188 (1992).

Corey et al., "Highly Enantioselective Routes to Darzens and Acetate Aldol Products from Achiral Aldehydes and t–Butyl Bromoacetate", Tetrahedron Letters, vol. 32, No. 25, pp. 2857–2860 (1991).

Deng et al., "A Practical, Highly Enantioselective Synthesis of the Taxol Side Chain via Asymmetric Catalysis", J. Org. Chem., vol. 57, pp. 4320–4323 (1992).

Denis et al., "Direct, Highly Efficient Synthesis from (S)–(+)–Phenylglycine of the Taxol and Taxotere Side Chains", J. Org. Chem., vol. 56, pp. 6939–6942 (1991).

Denis et al., "A Highly Efficient, Practical Approach to Natural Taxol", J. Am. Chem. Soc., vol. 110, pp. 5917–5919 (1988).

Denis et al., "An Improved Synthesis of the Taxol Side Chain and of RP 56976", J. Org. Chem., vol. 55, pp. 1957–1959 (1990).

Denis et al., "An Efficient, Enantioselective Synthesis of the Taxol Side Chain", J. Org. Chem., vol. 51, pp. 46–50 (1986).

Eliel et al, "Atrolactic Acid", Col. vol. IV, Organic Syntheses, pp. 58–62 (1963).

Georg et al., "Asymmetric Synthesis of β–lactams and N–Benzoyl–3–Phenylisoserines Via the Staudinger Reaction", Tetrahedron Letters, vol. 32, No. 27, pp. 3151–3154 (1991).

Drefahl et al., Stereochemischer Verlauf von Ringschlubreaktionen der diastereomeren DL–1–Amino–1.2–diphenyl–propanole–(2), Chemische Berichte, 91, pp. 1092–1099 (1958).

(List continued on next page.)

*Primary Examiner*—Donald G. Daus
*Attorney, Agent, or Firm*—Suzanne E. Babajko; Frank P. Hoffman

[57] ABSTRACT

Novel methods for the preparation of sidechain-bearing taxanes, comprising the preparation of an oxazoline compound, coupling the oxazoline compound with a taxane having a hydroxyl group directly bonded at C-13 thereof to form an oxazoline sidechain-bearing taxane, and opening the oxazoline ring of the oxazoline sidechain-bearing taxane so formed. Novel compounds prepared by the methods of the present invention are also provided.

2 Claims, No Drawings

OTHER PUBLICATIONS

Ghera et al., Formation of $\Delta^2$–Oxazolines by Cyclization of N–Acyl–β–Hydroxyamines on Zinc Acetate. An Oxazoline Complex of Zinc Acetate, J.C.S. Chem. Comm., pp. 639–640 (1972).

Harada et al., "Optical Resolution and Configuration of cis–β–Phenylglycidic Acid", Bulletin of the Chemical Society of Japan, vol. 47 (11), pp. 2911–2912 (1974).

Hauptmann et al., The Synthesis of Cystine–β,β'–dicarboxylic Acid, J. Am. Chem. Soc., vol. 77, pp. 704–707 (1955).

Hauptmann et al., "Reaction of Trans–Epoxy–Succinic Acid with Ammonia and Amines: β–Hydroxyaspartic acid and its N–alkyl Derivatives", Anais Assoc. Brasil. Quim., 19, pp. 173–183 (1960) (also, Chemical Abstracts, vol. 57, 16732h).

Heine et al., "Aziridines. XVI. Isomerization of Some 1–Aroylaziridines", J. Org. Chem., 32, pp. 3069–3074 (1967).

Honig et al., "Chemo–Enzymatic Synthesis of All Isomeric 3–Phenylserines and Isoserines", Tetrahedron, vol. 46, No. 11, pp. 3841–3850 (1990).

Kato et al., "Studies on Ketene and Its Derivatives. XLII. Ring–Expansion of 1–Acetoacetylaziridine", Yakugaku Zasshi vol. 91, pp. 384–392 (1971).

Kimball et al., "Ethyl α–Phenylacetoacetate", Organic Syntheses, Coll. vol. 2, pp. 284–286 (1943).

Magri et al., "Modified Taxols, 4. Synthesis and Biological Activity of Taxols Modified in the Side Chain", J. of Nat. Products, vol. 51, No. 2, pp. 298–306 (1988).

Nathansohn et al., "Steroids Possessing Nitrogen Atoms. IV Further Studies on the Synthesis of[17α,16α,–d]–oxazolinocorticoids", *Steroids*, 13, pp. 383–397 (1969).

Ojima et al., "New and Efficient Routes to Norstatine and its Analogs with High Enantiomeric Purity by β–lactam Synthon Method", Tetrahedron Letters, vol. 33, No. 39, pp. 5737–5740 (1992).

Ojima et al., "Efficient and Practical Asymmetric Synthesis of the Taxol C–13 Side Chain, N–Benzoyl–(2R,3S)–3–phenylisoserine and Its Analogues via Chiral 3–Hydroxy–4–aryl–β–lactams through Chiral Ester Enolate–Imine Cyclocondensation", J. Org. Chem., 56, pp. 1681–1683 (1991).

Ojima et al., "New and Efficient Approaches to the Semi-synthesis of Taxol and its C–13 Side Chain Analogs by Means of β–lactam Synthon Method", Tetrahedron, vol. 48, No. 34, pp. 6985–7012 (1992).

Pelchowicz et al., "Substituted Tryptamines and Their Derivatives", Journal of the Chemical Society, pp. 4699–4701 (1960).

Pfister et al., "The Synthesis of DL–Threonine. II. Interconversion of DL–Threonine and DL–Allothreonine", *JACS*, pp. 1101–1105 (1949).

Riordan et al., "Some Reactions of DL–trans–4,5–Dicarbomethoxy–2–phenyl–2–oxazoline", J. Org. Chem., vol. 40, No. 22, pp. 3219–3221 (1975).

Schmidt et al., "Synthesis of (4R)–4–(E)–2–Butenyl)–4, N–Dimethyl–L–Threonine (MeBMT), The Characteristic Amino Acid of Cyclosporine", Tetrahedron Letters, vol. 28, No. 25, pp. 2849–2852 (1987).

Solladie–Cavallo et al., "Synthesis of (2S,3R)–3–Amino–2–hydroxy–5–methylhexanoic Acid: Bridging Effect of KF", J. Org. Chem., vol. 55, pp. 4750–4754 (1990).

Wani et al., "Plant Antitumor Agents. VI. The Isolation and Structure of Taxol, a Novel Antileukemic and Antitumor Agent from *Taxus brevifolia*"; J. Amer. Chem. Society, pp. 2325–2327 (1971).

Zvonkova et al., "Synthesis of a Structural Analog of Sphingomyelin", J. Org. Chem. USSR (Engl. Transl.), 10, pp. 1637–1640 (1974).

Denis et al. J. Am. Chem Soc. vol. 110 pp. 5917–5919 (1988).

Magri et al. J. Nat. Prod. vol. 51 No. 2 pp. 298–306 (1988).

Gou et al. J. Org. Chem. vol. 58 No. 5 pp. 1287–1289 (1993).

PHOSPHORUS BEARING TAXANES INTERMEDIATES

CROSS REFERENCE TO RELATED APPLICATIONS

This is a continuation of application Ser. No. 08/600,353, filed Feb. 12, 1996, which is a continuation of application Ser. No. 08/171,792, filed Dec. 22, 1993 abandoned which is a continuation-in-part of application Ser. No. 07/995,443 filed Dec. 23, 1992, abandoned.

FIELD OF THE INVENTION

The present invention relates to methods for the preparation of sidechain-bearing taxanes and intermediates thereof, and to the novel compounds prepared by these methods.

BACKGROUND OF THE INVENTION

Taxanes are diterpene compounds which find utility in the pharmaceutical field. For example, taxol, a taxane having the structure:

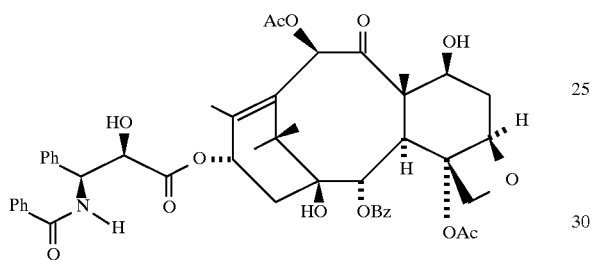

where Ph is phenyl, Ac is acetyl and Bz is benzoyl, has been found to be an effective anticancer agent. Naturally occurring taxanes such as taxol may be found in plant materials, and have been isolated therefrom. Such taxanes may, however, be present in plant materials in relatively small amounts so that, in the case of taxol, for example, large numbers of the slow-growing yew trees forming a source for the compound may be required. The art has thus continued to search for synthetic, including semi-synthetic routes for the preparation of taxanes such as taxol and analogs thereof, as well as routes for the preparation of intermediates used in the preparation of these compounds.

SUMMARY OF THE INVENTION

The present invention provides a novel, overall method for the preparation of novel sidechain-bearing taxanes, comprising the following steps (a) through (e):

(a) preparing an oxazoline compound of the following formula I or a salt thereof:

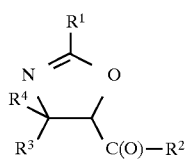

where
$R^1$ is $R^5$, $R^7$—O—, $R^7$—S—, or $(R^5)(R^6)N$—;
$R^2$ is $R^7$—O—, $R^7$—S—, or $(R^5)(R^6)N$—;
$R^3$ and $R^4$ are independently $R^5$, $R^5$—O—C(O)—, or $(R^5)(R^6)N$—C(O)—;
$R^5$ and $R^6$ are independently hydrogen, alkyl, alkenyl, alkynyl, cycloalkyl, cycloalkenyl, aryl, or heterocyclo; and $R^7$ is alkyl, alkenyl, alkynyl, cycloalkyl, cycloalkenyl, aryl or heterocyclo;

(b) converting the oxazoline of formula I or salt thereof to an oxazoline of the formula II or a salt thereof:

where $R^1$, $R^3$ and $R^4$ are as defined above;

(c) coupling the oxazoline of the formula II or salt thereof with a taxane having a hydroxyl group directly bonded to C-13 thereof, or salt thereof, to form an oxazoline sidechain-bearing taxane of the following formula III or a salt thereof:

where $R^1$, $R^3$ and $R^4$ are as defined above, and T is a taxane moiety preferably a compound of Formula IX bonded directly through C-13 of said moiety;

(d) contacting the oxazoline sidechain-bearing taxane of the formula III or salt thereof with an aqueous acid capable of opening the oxazoline ring of said compound of the formula III or salt thereof to form a sidechain-bearing taxane of the following formula X or salt thereof:

where $R^1$, $R^3$, $R^4$ and T are as defined above, and the acid salt at the amine group in said formula X is formed by contact with said ring-opening acid; and (e) contacting said sidechain-bearing taxane of the formula X or salt thereof with a base to form a sidechain-bearing taxane of the following formula IV or salt thereof:

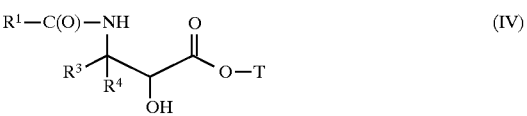

where $R^1$, $R^3$, $R^4$ and T are as defined above.

In addition, the present invention provides the individual methods of each of steps (a) through (e) which are novel methods, and the novel compounds of the formulae I, II, III, IV, IX and X and salts and hydrates thereof as described following. Also included are novel prodrugs of these compounds.

DETAILED DESCRIPTION OF THE INVENTION

The present invention is described further as follows.

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^5$)($R^6$)N—CO—where $R^5$ or $R^6$ are as defined above, except that at least one of $R^5$ or $R^6$ is not hydrogen), amino (—$NH_2$), heterocyclo, mono- or dialkylamino, or thiol (—SH).

The terms "lower alk" or "lower alkyl" as used herein, denote such optionally substituted groups as described above for alkyl having 1 to 4 carbon atoms in the normal chain.

The terms "alkoxy" or "alkylthio" denote an alkyl group as described above bonded through an oxygen linkage (—O—) or a sulfur linkage (—S—), respectively. The term "alkyloxycarbonyl", as used herein, denotes an alkoxy group bonded through a carbonyl group. The term "alkylcarbonyl", as used herein, denotes an alkyl group bonded through a carbonyl group. The term "alkylcarbonyloxy", as used herein, denotes an alkyl group bonded through a carbonyl group which is, in turn, bonded through an oxygen linkage. The terms "monoalkylamino" or "dialkylamino" denote an amino group substituted by one or two alkyl groups as described above, respectively.

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^5$)($R^6$)N—CO— where $R^5$ or $R^6$ are as defined above, except that at least one of $R^5$ or $R^6$ is not hydrogen), amino (—$NH_2$), heterocyclo, mono- or dialkylamino, or thiol (—SH).

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include ethynyl, propynyl, butynyl, pentynyl, hexynyl, heptynyl, octynyl, nonynyl, decynyl, and the like. Exemplary substituents may include one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^5$)($R^6$)N—CO— where $R^5$ or $R^6$ are as defined above, except that at least one of $R^5$ or $R^6$ is not hydrogen), amino (—$NH_2$), heterocyclo, mono- or dialkylamino, or thiol (—SH).

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above or groups described above as alkyl substituents.

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. Exemplary substituents include one or more alkyl groups as described above or one or more groups described above as alkyl substituents. Also included are smaller heterocyclos, such as, epoxides and aziridines.

The terms "halogen", "halo", or "hal", as used herein alone or as part of another group, denote chlorine, bromine, fluorine, and iodine.

The term "taxane moiety", as used herein, denotes moieties containing the core structure:

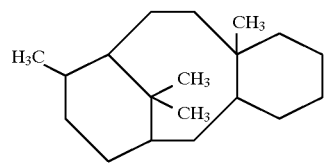

which core structure may be substituted and which may contain ethylenic unsaturation in the ring system thereof.

The term "taxane", as used herein, denotes compounds containing a taxane moiety as described above.

The term "hydroxy (or hydroxyl) protecting group", as used herein, denotes any group capable of protecting a free hydroxyl group which, subsequent to the reaction for which it is employed, may be removed without destroying the remainder of the molecule. Such groups, and the synthesis thereof, may be found in "Protective Groups in Organic Synthesis" by T. W. Greene, John Wiley and Sons, 1991, or Fieser & Fieser. Exemplary hydroxyl protecting groups include methoxymethyl, 1-ethoxyethyl, 1-methoxy-1-methylethyl, benzyloxymethyl, (β-trimethylsilylethoxy)

methyl, tetrahydropyranyl, 2,2,2-trichloroethoxycarbonyl, t-butyl(diphenyl)silyl, trialkylsilyl, trichloromethoxycarbonyl, and 2,2,2-trichloroethoxymethyl.

The term "salts" includes acidic and/or basic salts formed with inorganic and/or organic acids and bases. Exemplary acidic salts include salts formed with mineral acids such as HCl, $H_2SO_4$, or $HNO_3$, or carboxylic acids such as trifluoroacetic acid or acetic acid. Exemplary basic salts include salts formed with amines such as triethylamine, diisopropylethylamine, or pyridine or amino acids such as arginine, or guanidine. Salts of hydroxyl groups, such as metal (e.g., alkali or alkaline earth metal) alkoxides, are also contemplated as "salts" herein. Metal alkoxide salts may, for example, be formed by contacting a hydroxyl group with a metallating agent.

Reference to a compound employed in or prepared by the methods of the present invention includes salts and hydrates thereof, unless otherwise indicated.

Preparation of Oxazoline Compounds of the Formula I and Salts Thereof

The present invention provides novel methods for the preparation of oxazoline compounds of the formula I and salts thereof, in particular, the dehydration, displacement, and exchange methods described following.

The present invention also provides the novel oxazoline compounds of the formula I and salts thereof, including all stereoisomers thereof, either substantially free of other stereoisomers, or in admixture with other selected, or all other stereoisomers, with the provisos that, when $R^1$ is phenyl and one of $R^3$ or $R^4$ is hydrogen, (i) $R^2$ is not methoxy when the other of $R^3$ or $R^4$ is pentadecyl, benzyl, or methoxycarbonyl, or (ii) $R^2$ is not ethoxy when the other of $R^3$ or $R^4$ is ethoxycarbonyl; when $R^1$ is methyl and one of $R^3$ or $R^4$ is hydrogen, $R^2$ is not 8-phenylmenthyloxy when the other of $R^3$ or $R^4$ is 2-methylpropyl; and when $R^1$ is acetylmethyl and $R^3$ and $R^4$ are hydrogen, $R_2$ is not ethoxy or $NH_2$.

Oxazolines of the formula Ia and salts thereof described following are preferred, especially compounds of the formula Ia having those substituents set forth in the section below entitled "Preferred Compounds".

Dehydration Method

Oxazoline compounds of the formula I or salts thereof may be prepared by a dehydration method, comprising the step of contacting a compound of the following formula V or a salt thereof:

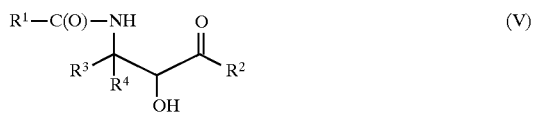

where $R^1$, $R^2$, $R^3$ and $R^4$ are as defined above, with an acid capable of effecting dehydration of the compound of formula V or salt thereof to form a compound of the formula I or salt thereof.

The starting compounds of the formula V and salts thereof may be prepared by procedures such as those described in U.S. Pat. No. 5,420,337; Ojima et al., *J. Org. Chem.*, 56, 1681–1683 (1991); Georg et al., *Tetrahedron Lett.*, 32, 3151–3154 (1991); Denis et al., *J. Org. Chem.*, 51, 46–50 (1986); Corey et al., *Tetrahedron Lett.*, 32, 2857–2860 (1991); Deng et al., *J. Org. Chem.*, 57, 4320–4323 (1992); Ojima et al., *Tetrahedron*, 48, 6985–7012 (1992); Commercon et al., *Tett. Lett.*, 33, 5185–5188 (1992); Denis et al., *J. Org. Chem.*, 56(24), 6939–6942 (1991) (for example, followed by esterification and treatment with acid); and Denis et al., *J. Org. Chem.*, 55, 1957–1959 (1990), all incorporated herein by reference.

Any acid capable of effecting dehydration may be employed in the dehydration method of the present invention. Exemplary acids include sulfonic acids such as pyridinium p-toluene sulfonic acid, p-toluene sulfonic acid, camphorsulfonic acid, and methane sulfonic acid, carboxylic acids such as trifluoroacetic acid or acetic acid, or mineral acids such as HCl, $H_2SO_4$ or $HNO_3$. Mole ratios of acid:compound of formula V are preferably from about 1:100 to about 1:1.

The reaction is preferably conducted at a temperature of from about 0° C. to about 200° C., and at a pressure of about 1 atm to about 5 atm. The reaction is preferably conducted under an atmosphere of inert gas such as argon.

Solvents are preferably employed which are inert, organic solvents such as toluene, tetrahydrofuran, acetonitrile, benzene or xylene. The amount of solvent employed preferably provides a loading of the starting compound of formula V of about 2.5% by weight, based on the combined weight of solvent and formula V compound.

The oxazoline ring of the compounds of the formula I is numbered herein as follows:

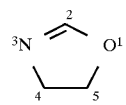

With respect to the 4- and 5-position carbon atoms, the oxazoline compounds of the formula I may exist as four stereoisomers Ia, Ib, Ic and Id as follows:

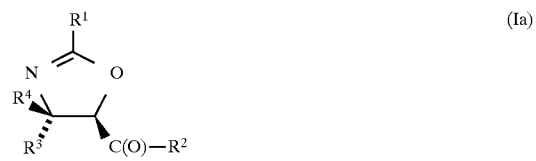

(Ia)

(Ib)

(Ic)

(Id)

The compounds of the formula V may also exist as four stereoisomers, with respect to the carbon atoms at the corresponding positions. These stereoisomers are the following compounds Va, Vb, Vc and Vd:

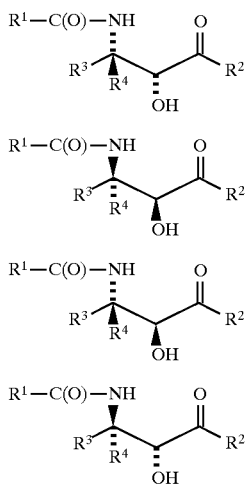

(Va)

(Vb)

(Vc)

(Vd)

A desired stereoisomer of the compound of the formula I may, for example, be prepared by the present dehydration method by employing the appropriate stereoisomer of the starting compound of the formula V. Thus, use of a compound Va will provide a compound Ia, use of a compound Vb will provide a compound Id, use of a compound Vc will provide a compound Ic, and use of a compound Vd will provide a compound Ib. It is preferred to employ a single stereoisomer of the starting compound V in the present dehydration method, although stereoisomeric mixtures may also be employed. Use of a compound Va to prepare a compound Ia, especially to prepare a compound Ia having those substituents set forth in the section below entitled "Preferred Compounds", is particularly preferred.

Displacement Method

Oxazoline compounds of the formula I or salts thereof may also be prepared by a displacement method, comprising the step of contacting a compound of the formula V or salt thereof, in the presence of a base, with an activating agent capable of activating the hydroxyl group of the compound of the formula V or salt thereof to allow intramolecular displacement and formation of a compound of the formula I or salt thereof, with the proviso that, when $R^1$ is phenyl, and one of $R^3$ or $R^4$ is hydrogen, (i) $R^2$ is not ethoxy when the other of $R^3$ or $R^4$ is ethoxycarbonyl, or (ii) $R^2$ is not methoxy when the other of $R^3$ or $R^4$ is benzyl.

Any compound capable of activating the hydroxyl group of the compound of the formula V and effecting intramolecular displacement may be employed as the activating agent in the displacement method of the present invention. Exemplary activating agents include sulfonyl halides such as alkyl sulfonyl halides (e.g., methyl sulfonyl chloride), or aryl sulfonyl halides (e.g., benzene sulfonyl chloride or p-toluenesulfonyl chloride), phosphorus oxychloride ($POCl_3$), phosphorus pentachloride ($PCl_5$), or thionyl chloride ($SOCl_2$). Mole ratios of activating agent: compound of formula V are preferably from about 1:1 to about 2:1.

Activation of the hydroxyl group of a compound of the formula V or salt thereof may produce a novel intermediate compound of the formula VI or salt thereof:

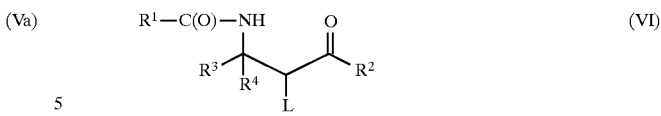

where $R^1$, $R^2$, $R^3$ and $R^4$ are as defined above, and L is a leaving group such as alkyl sulfonyloxy (e.g., methyl sulfonyloxy), aryl sulfonyloxy (e.g., benzene sulfonyloxy or p-toluenesulfonyloxy), chloro, or a phosphorus oxy group ($PO_2$— or PO—). The present invention provides the aforementioned novel compounds of the formula VI and salts thereof, including all stereoisomers thereof, either substantially free of other stereoisomers, or in admixture with other selected, or all other stereoisomers, with the proviso that, when $R^1$ is phenyl, $R^2$ is methoxy and one of $R^3$ or $R^4$ is hydrogen and the other benzyl, L is not chloro.

Bases which may be employed include organic bases such as amines (e.g., pyridine, triethylamine, diisopropylethylamine, lutidine, or 1,8-diazabicyclo[5.4.0]undec-7-ene), or lithium hexamethyl disilazide, or inorganic bases such as alkali metal carbonates (e.g., potassium carbonate). Mole ratios of base: compound of formula V are preferably greater than about 2:1.

The reaction is preferably conducted at a temperature of from about −20° C. to about 100° C., particularly 0° C., and at a pressure of about 1 atm. The reaction is preferably conducted under an atmosphere of inert gas such as argon.

Solvents are preferably employed which are inert organic solvents such as chloroform, methylene chloride, toluene, tetrahydrofuran, acetonitrile or, most preferably, which are basic organic solvents capable of functioning both as solvent and as base for the present method such as pyridine, triethylamine, or lutidine. The amount of solvent employed preferably provides a loading of the starting compound of the formula V of about 10% by weight, based on the combined weight of solvent and formula V compound.

A desired stereoisomer of the compound of the formula I may, for example, be prepared by the present displacement method by employing the appropriate stereoisomer of the starting compound of the formula V. Thus, use of a compound Va will provide a compound Ic, use of a compound Vb will provide a compound Ib, use of a compound Vc will provide a compound Ia, and use of a compound Vd will provide a compound Id. It is preferred to employ a single stereoisomer of the starting compound V in the present displacement method, although stereoisomeric mixtures may also be employed. Use of a compound Vc to form a compound Ia, especially to prepare a compound Ia having those substituents set forth in the section below entitled "Preferred Compounds", is particularly preferred.

Exchange Method

Oxazoline compounds of the formula I where $R^1$ is $R^1$ as defined following or salts thereof may also be prepared by an exchange method, comprising the step of contacting a compound of the following formula VII or salt thereof:

where $R^2$, $R^3$ and $R^4$ are as defined above, with a compound of the following formula VIII or salt thereof:

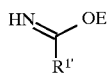 (VIII)

where $R^{1'}$ and E are independently alkyl, alkenyl, alkynyl, cycloalkyl, cycloalkenyl, aryl or heterocyclo, with the provisos that, when E is ethyl, one of $R^3$ or $R^4$ is hydrogen, and (i) $R^{1'}$ is phenyl, $R^2$ is not methoxy when the other of $R^3$ or $R^4$ is methoxycarbonyl, and $R^2$ is not ethoxy when the other of $R^3$ or $R^4$ is ethoxycarbonyl; and (ii) $R^{1'}$ is methyl, $R^2$ is not 8-phenylmenthyloxy when the other of $R^3$ or $R^4$ is 2-methylpropyl.

When both starting compounds VII and VIII are simultaneously employed as acid salts at the $NH_2$ and HN groups, respectively, an amine base, such as ammonia or an organic amine base, may be employed to form a free $NH_2$ and/or HN group, respectively, to allow the reaction to proceed efficiently. Any amine base capable of forming the free $NH_2$ and/or HN group(s) may be employed therein. Tertiary amine bases such as triethylamine, diisopropylethylamine, lutidine, pyridine or 1,8-diazabicyclo[5.4.0]undec-7-ene are preferred. Mole ratios of amine base: compound of formula VII are preferably from about 1:1 to about 10:1.

The starting compounds of the formula VII and salts thereof may be prepared by methods such as those described in U.S. Pat. application Ser. No. 07/975,453, filed Nov. 12, 1992 by Patel et al.; Commercon et al., *Tetrahedron Lett.*, 33 (36), 5185–5188 (1992); Corey et al., *Tetrahedron Lett.*, 32, 2857–2860 (1991); Ojima et al., *Tetrahedron*, 48, 6985–7012 (1992); and Ojima et al., *Tetrahedron Lett.*, 33, 5737–5740 (1992), all incorporated herein by reference. The starting compounds of the formula VII and salts thereof may be prepared by methods such as those described in Kimball et al., *Org. Synth. Coll.* Vol. II, p. 284 (1943). Use of acidic salts of compounds of the formula VIII, for example, salts formed with carboxylic, sulfonic or mineral acids, are preferably employed as starting materials, as such compounds are relatively stable and easily handled. The aforementioned salts may be neutralized upon contact with the base employed as discussed above. Mole ratios of compound of formula VIII: compound of formula VII are preferably from about 1:1 to about 2:1.

The reaction is preferably conducted at a temperature of from about 0° C. to about 100° C., and at a pressure of about 1 atm. The reaction is preferably conducted under an inert atmosphere, such as argon or nitrogen.

Solvents are preferably employed which are inert organic solvents such as toluene, tetrahydrofuran, dichloromethane, 1,2-dichloroethane, or chloroform. The amount of solvent employed preferably provides a loading of the starting compound of the formula VII of about 6% by weight, based on the combined weight of solvent and formula VII compound.

The compounds of the formula VII may, as with the compounds of the formula V, exist as four stereoisomers with respect to the carbon atoms at the corresponding positions. These stereoisomers are the following compounds VIIa, VIIb, VIIc and VIId:

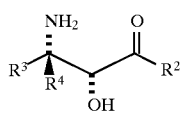 (VIIa)

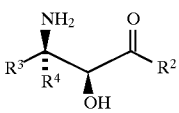 (VIIb)

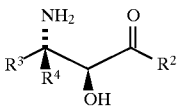 (VIIc)

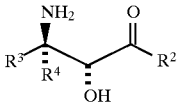 (VIId)

A desired stereoisomer of the compound of the formula I may, for example, be prepared by the present exchange method by employing the appropriate stereoisomer of the starting compound of the formula VII. Thus, use of a compound VIIa will provide a compound Ia, use of a compound VIIb will provide a compound Id, use of a compound VIIc will provide a compound Ic, and use of a compound VIId will provide a compound Ib. It is preferred to employ a single stereoisomer of the starting compound VII in the present exchange method, although stereoisomeric mixtures may also be employed. Use of a compound VIIa to prepare a compound Ia, especially to prepare a compound Ia having those substituents set forth in the section below entitled "Preferred Compounds", is particularly preferred.

Preparation of Oxazoline Compounds of the Formula II and Salts Thereof

Oxazoline compounds of the formula II and salts thereof may be prepared from oxazoline compounds of the formula I and salts thereof by converting the group —C(O)—$R^2$ to the group —C(O)—OH.

Any agent capable of the aforementioned conversion may be employed. For example, when $R^2$ is alkoxy such as methoxy or ethoxy, the compound of the formula I or salt thereof may be dealkylated to form a compound of the formula II by use of a suitable nucleophilic agent, such as the alkali or alkaline earth metal salts of methanethiol. Alternatively, hydrogenation may be employed, for example, to convert groups such as benzyloxycarbonyl to carboxyl, by use of a hydrogenating agent, for example, hydrogen and a hydrogenation catalyst such as palladium.

Preferably, conversion of the group —C(O)—$R^2$ to a carboxyl group is conducted by hydrolysis. Any compound capable of effecting hydrolysis may be employed as the hydrolysis agent therein. Exemplary hydrolysis agents include aqueous bases such as hydroxides (e.g., metal hydroxides such as barium hydroxide, or preferably, alkali metal hydroxides such as lithium, sodium or potassium hydroxide). Mole ratios of base: compound of formula I are preferably from about 1:1 to about 3:1. Mole ratios of water: compound of formula I are preferably from about 1:1 to about 100:1.

The reaction is preferably conducted at a temperature of from about −20° C. to about 100° C., and at a pressure of about 1 atm. Hydroxide saponification of compounds of the formula I or salts thereof where $R^2$ is —N($R^5$)($R^6$) is preferably conducted at the higher temperatures of the aforementioned temperature range, or at temperatures approaching or at the reflux temperature of the liquid medium employed. The reaction is preferably conducted under an atmosphere of nitrogen, argon or air.

Solvents may be selected from inorganic and organic liquids such as water, alcohols, toluene, tetrahydrofuran, dioxane, acetonitrile, or dimethylformamide, or mixtures thereof. A mixture of water and an organic liquid such as tetrahydrofuran is preferably employed as solvent. The amount of solvent employed preferably provides a loading of the starting compound of the formula I of about 7% by weight, based on the combined weight of solvent and formula I compound.

The present invention also provides the novel compounds of the formula II and salts thereof, including all stereoisomers thereof, either substantially free of other stereoisomers, or in admixture with other selected, or all other stereoisomers, with the proviso that, when $R_1$ is phenyl and one of $R^3$ or $R^4$ is hydrogen, the other of $R^3$ or $R^4$ is not COOH. As with the oxazolines of the formula I, the oxazolines of the formula II may exist as four stereoisomers with respect to the 4- and 5-position carbon atoms. These stereoisomers are the following compounds IIa, IIb, IIc and IId:

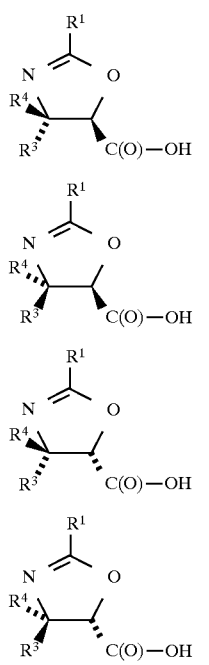

Oxazolines of the formula IIa and salts thereof are preferred, especially compounds of the formula IIa having those substituents set forth in the section below entitled "Preferred Compounds".

The stereoconfiguration of the starting compound of the formula I or salt thereof may be retained and/or inverted in the present method. Thus, for example, hydrolysis of a compound of the formula I having substituents which are in the cis position relative to each other at the 4- and 5-positions may be hydrolyzed to provide a compound of the formula II having the corresponding cis configuration, a compound of the formula II having the corresponding trans configuration where the 5-position carboxyl substituent is inverted relative to the starting compound, or a mixture of the aforementioned cis and trans compounds. Bases which, when employed for hydrolysis, deprotonate the carbon atom through which the group —C(O)—$R^2$ is bonded, and which subsequently reprotonate the aforementioned carbon from the opposite face of the ring system, result in inversion of the stereoconfiguration. Exemplary such bases include those described above or alkali metal carbonates such as potassium carbonate, amine bases, or metal, such as alkali or alkaline earth metal, alkoxides, the latter which may be formed prior to addition thereof or in situ (for example, by addition of a metallating agent such as n-butyllithium together with an alkanol such as ethanol).

Where the stereoconfiguration is inverted during the present method as described above, a compound of the formula I having an inverted stereoconfiguration relative to the starting compound of the formula I may be formed as an intermediate (i.e., epimerization). Thus, for example, where the starting compound of the formula I has substituents at the 4- and 5-positions which are in the cis position relative to each other, the corresponding trans compound of the formula I where the 5-position substituent —C(O)—$R^2$ is inverted relative to the starting compound may be formed as in intermediate during the hydrolysis reaction. The aforementioned inversion method is also contemplated within the scope of the present invention.

Coupling to Prepare Oxazoline Sidechain-bearing Taxanes of the Formula III and Salts Thereof A sidechain-bearing taxane of the formula III or a salt thereof may be prepared by a method comprising the step of contacting an oxazoline compound of the formula II or a salt thereof, with a taxane having a hydroxyl group directly bonded to C-13 thereof, or a salt thereof, in the presence of a coupling agent. It is preferred to employ oxazolines of the formula IIa or salts thereof in the present method, especially compounds of the formula IIa having those substituents set forth in the section below entitled "Preferred Compounds".

Taxanes are compounds containing the core structure:

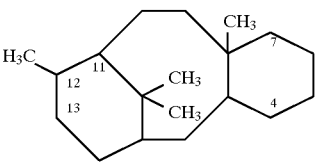

which core structure may be substituted and which may contain ethylenic unsaturation in the ring system thereof, as described above. Any taxane containing a hydroxyl group directly bonded to C-13 thereof, or salt thereof (such as a metal alkoxide salt at the C-13 hydroxyl group) may be employed in the present method. The taxane starting material employed in the method of the present invention may be a compound such as those described in European Patent Publication No. 400,971, incorporated herein by reference, which corresponds to U.S. Pat. No. 5,175,315, or may be a compound containing a taxane moiety described in, and prepared by procedures described in or analogous to those set forth in, U.S. Pat. No. 5,254,580 by Chen et al., or in U.S. Pat. No. 5,272,171 by Ueda et al., both incorporated herein by reference. Exemplary such taxanes include those of the following formula IX:

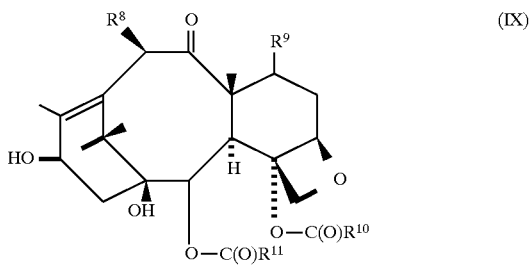

where $R^8$ is hydrogen, hydroxyl, $R^{14}$—O—, $R^{15}$—C(O)—O—, or $R^{15}$—O—C(O)—O—;

$R^9$ is hydrogen, hydroxyl, fluoro, $R^{14}$—O—, $R^{15}$—C(O)—O— or $R^{15}$—O—C(O)—O—;

$R^{10}$ and $R^{11}$ are independently hydrogen, alkyl, alkenyl, alkynyl, cycloalkyl, cycloalkenyl, R16—O—, aryl, or heterocyclo;

$R^{14}$ is a hydroxyl protecting group; and $R^{15}$ is hydrogen, alkyl, alkenyl, alkynyl, cycloalkyl, cycloalkenyl, aryl or heterocyclo, $R^{16}$ is alkyl or salts thereof.

All stereoconfigurations of the unspecified chiral centers of the compound of the formula IX are contemplated for use in the coupling method of the present invention. The use of a single stereoisomer is preferred, although mixtures thereof may be employed. 7-Trialkylsilyl baccatin III compounds are one of the compounds preferably employed as the starting material of formula IX, most preferably, 7-trimethylsilyl baccatin III or 7-triethylsilyl baccatin III.

Another series of compounds which are preferable starting materials of formula IX are compounds wherein $R^8$ is $OC(O)CH_3$; $R^9$ is hydroxyl or a hydroxyl protecting group e.g. O-trimethylsilyl or O-triethylsilyl; $R^{10}$ is as above except methyl and $R^{11}$ is aryl e.g. benzyl. The latter compounds are considered novel along with methods for their preparation which are set forth below. Especially preferred of the above compounds are those wherein $R^{10}$ is cycloalkyl or $OR^{16}$.

The above compounds are prepared by the following general reaction scheme catin III is soluble may be utilized, such as, THF, DMF, $MeCl_2$ and dioxane. The reaction is carried out in the presence of a tertiary amine base, such as, pyridine or imidazole. The reaction temperature can vary from –30° C. to room temperature with C-7 substitution occuring preferably at –30° C. to 0° C. and C-13 at 0° C. to room temperature. The protecting group reactant concentration is preferably in molar excess (1–10) to effect both C-7 and C-13 substitution.

Step G

The intermediate XI is thereafter protected at the C-1 hydroxy by reaction with a trimethylsilane or preferably a dimethylsilane e.g. chlorotrimethylsilane or preferably chlorodimethylsilane in, for example, DMF, THF, dioxane or various ethers. As in step F the reaction is preferably carried out in the presence of a tertiary amine base, such as imidazole or pyridine. The temperature can range from –30° C. to room temperature with about 0° C. as preferred.

Step H (A) Intermediate XII is thereafter reduced at C-4 to hydroxy by reaction with a suitable reducing agent such as Red-Al or lithium aluminum hydride. The reducing agent is usually present in molar excess (1–5 equivalents). The reaction solvent can be THF, dioxane or various suitable ethers and the reaction temperature can range from –30° C. to 0° C. with about 0° C. as preferred.

(B) Intermediate XIII of (A) wherein C-4 is hydroxy is converted to the appropriate C-4 substituent by reaction with the appropriate acyl chloride acid anhydride or mixed anhydride e.g. acryloyl chloride, benzoyl chloride, cycloalkylcarbonyl chloride, alkyl chloroformate, in the presence of an alkali metal (Li, Na or K) anion of a secondary amine base. The reaction solvents include THF, dioxane, etc. The tem-

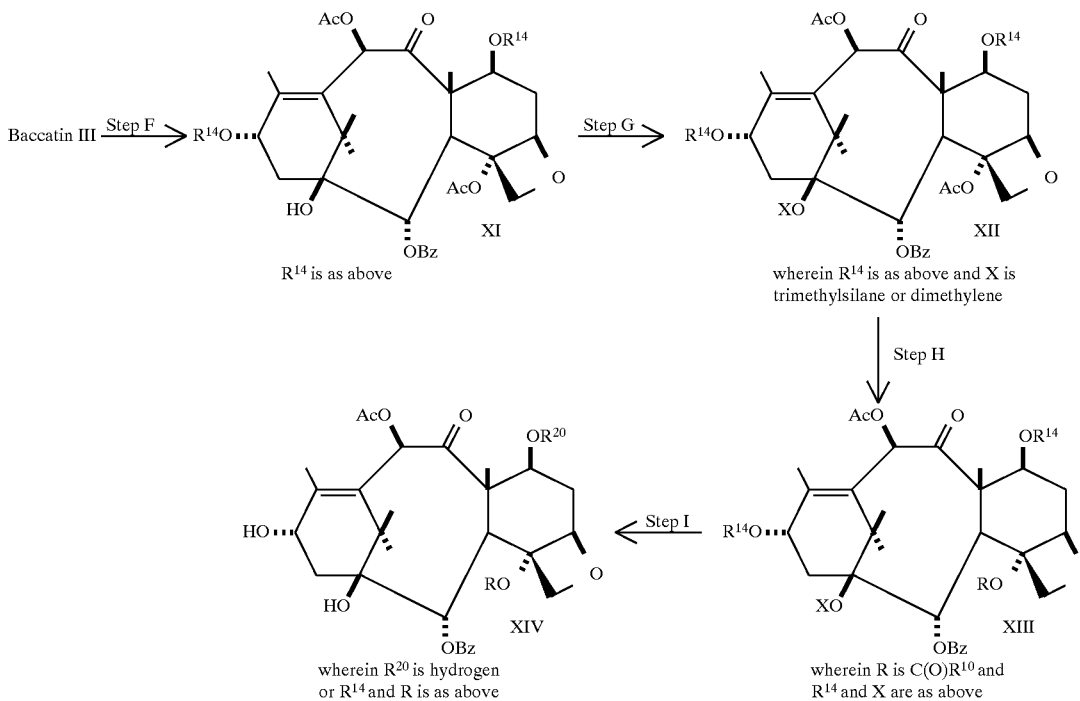

Step F

Baccatin III is protected at the C-7 and C-13 sites by reaction with a suitable agent, such as, a halotrialkylsilane e.g. trimethyl or triethyl, 2,2,2-trichloroethyl chloroformate or carbobenzyloxy. Any inert organic solvent wherein Bacperature range can be from –30° C. to room temperature with about 0° C. as preferred.

Step I (A) The intermediate XIII of step H (B) is thereafter deprotected by reaction with pyridinium fluoride (aqueous hydrogen fluoride in pyridine) in acetonitrile followed by tetrabutylammonium fluoride in THF or cesium fluoride in THF. Thereafter the mixture is diluted in an alcohol, washed with mild organic or inorganic acid and isolated.

(B) Thereafter the C-7 hydroxy protecting group may be introduced in XIV as in Step F following reaction parameters favoring C-7 substitution above.

Subsequently, the appropriate side chain may be introduced at C-13 following the novel process disclosed herein or alternatively via Holton methodology as disclosed in U.S. Pat. Nos. 5,227,400, 5,175,315 and 5,229,526 which are herein incorporated by reference.

As novel end products of the present invention therefore are compounds of the formula

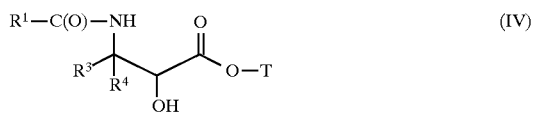

where $R^1$ is $R^5$, $R^7$—O—, $R^7$—S—, or $(R^5)(R^6)N$—;

$R^3$ and $R^4$ are independently $R^5$, $R^5$—O—C(O)—, or $(R^5)(R^6)N$—C(O)—;

$R^5$ and $R^6$ are independently hydrogen, alkyl, alkenyl, alkynyl, cycloalkyl, cycloalkenyl, aryl or heterocyclo; and $R^7$ is alkyl, alkenyl, alkynyl, cycloalkyl, cycloalkenyl, aryl or heterocyclo;

and T is

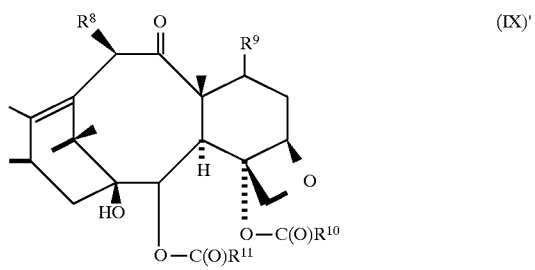

where $R^8$ is hydrogen, hydroxyl, $R^{14}$—O—, $R^{15}$—C—(O)—O—, or $R^{15}$—O—C(O)—O—;

$R^9$ is hydrogen, hydroxyl, fluoro, $R^{14}$—O—, $R^5$—C(O)—O— or $R^{15}$—O—C(O)—O—;

$R^{10}$ and $R^{11}$ are independently hydrogen, alkyl, alkenyl, alkynyl, cycloalkyl, cycloalkenyl, $R^{16}$—O—aryl, or heterocyclo;

$R^{14}$ is a hydroxyl protecting group; and $R^{15}$ is hydrogen, alkyl, alkenyl, alkynyl, cycloalkyl, cycloalkenyl, aryl or heterocyclo, $R^{16}$ is alkyl with the proviso that $R^{10}$ is not methyl or salts or hydrates thereof.

Preferred Compounds

Especially preferred among the novel compounds of formula IV are those compounds wherein $R^{10}$ is cycloalkyl or $OR^{16}$. Most preferred among the novel compound of formula IV are compounds wherein $R^{10}$ is cycloalkyl, $R^1$ is aryl, preferably phenyl, or alkoxy preferably t-butyloxy; $R^3$ is aryl, preferably phenyl, heterocyclo preferably 2- or 3-furanyl or thienyl, isobutenyl, 2-propenyl, isopropyl or $(CH_3)_2CH$—; $R^4$ is hydrogen; $R^8$ is preferably hydroxyl or alkylcarbonyloxy, e.g. acetyloxy; $R^9$ is hydroxy and $R^{11}$ is aryl, preferably phenyl.

Any compound capable of effecting esterification of the C-13 hydroxyl group, or salt thereof, of the starting taxane through the carboxyl group of the oxazoline of the formula II or salt thereof may be employed as the coupling agent of the present method. Exemplary coupling agents include those compounds forming an activated oxazoline ester (for example, 1-hydroxybenzotriazole or N-hydroxysuccinimide) or anhydride (for example, an acid chloride such as pivaloyl chloride or bis(2-oxo-3-oxazolidinyl)-phosphinic chloride) when contacted with the oxazoline of the formula II, particularly coupling agents comprising a compound such as a carbodiimide (e.g., dicyclohexylcarbodiimide (DCC), 1,3-diisopropylcarbodiimide (DIC), or 1-(3-dimethylaminopropyl)-3-ethyl-carbodiimide hydrochloride), bis(2-oxo-3-oxazolidinyl) phosphinic chloride), carbonyl diimidazole (CDI), pivaloyl chloride, or 2.4,6-trichlorobenzyl chloride; wherein the aforementioned compounds are preferably employed together with a compound such as 1-hydroxybenzotriazole (HOBt) or N-hydroxysuccinimide (HO-Su), or an amine such as triethylamine, pyridine or pyridine substituted at the 4-position with —$N(R^{16})(R^{17})$, where $R^{16}$ and $R^{17}$ are independently selected from alkyl, alkenyl, alkynyl, cycloalkyl, cycloalkenyl or heterocyclo (to form a compound such as 4-dimethylaminopyridine (DMAP)), or where $R^{16}$ and $R^{17}$, together with the nitrogen atom to which they are bonded, form a heterocyclo group (to form a compound such as 4-morpholinopyridine or 4-pyrrolidinopyridine). Mole ratios of coupling agent: starting taxane are preferably from about 1:1 to about 2:1. Mole ratios of oxazoline of the formula II: starting taxane are preferably from about 1:1 to about 2.1.

The reaction is preferably conducted at a temperature of from about 0° C. to about 140° C., and at a pressure of about 1 atm. The reaction is preferably conducted under an atmosphere of inert gas such as argon.

Solvents are preferably employed which are inert organic liquids such as toluene, acetonitrile, 1,2-dichloroethane, chloroform, tetrahydrofuran, pyridine, methylene chloride or dimethylformamide. The amount of solvent employed preferably provides a loading of the starting taxane of about 20% by weight, based on the combined weight of solvent and taxane compound.

The stereoconfiguration of the substituents at the 4- and 5-positions of the starting oxazoline may be retained and/or inverted in the coupled formula III product, for example, epimerization from cis to trans where the 5-position substituent has been inverted relative to the starting material is contemplated.

The present invention also provides the novel oxazoline sidechain-bearing taxanes of the formula III and salts thereof, including all stereoisomers thereof, either substantially free of other stereoisomers, or in admixture with other selected, or all other stereoisomers.

Ring Opening to Form Taxanes of the Formula X and Salts Thereof

A sidechain-bearing taxane of the formula X or a salt thereof may be prepared from an oxazoline sidechain-bearing taxane of the formula III or a salt thereof, by a method comprising the step of contacting a taxane of the formula III or salt thereof with an aqueous acid capable of opening the ring of the oxazoline group bonded through C-13 of the taxane moiety of said taxane compound to form said compound of the formula X or salt thereof.

Any aqueous acid capable of effecting the aforementioned ring opening may be employed in the method of the present invention. Exemplary ring opening acids include carboxylic acids, such as acetic acid or trifluoroacetic acid, or preferably, mineral acids such as hydrochloric acid, hydrofluoric acid or sulfuric acid, in water. Mole ratios of ring opening acid: compound of formula III are preferably from about 1:1 to about 10:1. Mole ratios of water: compound of formula III are preferably from about 1:1 to about 100:1.

The ring opening reaction is preferably conducted at a temperature of from about −20° C. to about 40° C., and at a pressure of about 1 atm. The reaction is preferably conducted under an atmosphere of nitrogen, argon or air.

Solvents are preferably employed which are inert organic liquids alone or in admixture with water such as tetrahydrofuran, alcohols (preferably, lower alkanols such as methanol), dioxane, toluene, acetonitrile, or mixtures thereof. The amount of solvent employed preferably provides a loading of the starting compound of the formula III of about 5% by weight, based on the combined weight of solvent and formula III compound.

A preferred embodiment of the present invention further comprises the step of deprotecting one or more groups, particularly to free hydroxyl groups, on the taxane moiety to prepare taxanes of the formula X. Deprotection may, for example, be conducted prior or subsequent to, or simultaneously with, the aforementioned ring opening method by use of a deprotection agent. Any compound capable of deprotection may be employed as the deprotection agent. For example, acids such as hydrofluoric acid or aqueous protic acids, or tetra-alkylammonium fluorides such as tetra-n-butylammonium fluoride, may be employed for removal of silyl protecting groups; benzyl protecting groups may be removed by hydrogenation, trichloroethoxycarbonyl protecting groups may be removed by contact with zinc; and acetal or ketal protecting groups may be removed by the use of protic acids or Lewis acids.

A preferred embodiment of the present invention comprises simultaneous ring opening and deprotection of one or more hydroxyl groups on the taxane ring structure, particularly at C-7. A particularly preferred embodiment comprises the step of simultaneous ring opening and deprotection by use of an acid (e.g., a mineral acid such as hydrochloric acid) capable of effecting both reactions. Thus, for example, use of an acid under reaction conditions described above for ring opening may allow simultaneous ring opening and deprotection of acid cleavable hydroxyl protecting groups at C-7 such as trialkylsilyl (e.g. trimethylsilyl or triethylsilyl).

The present invention also provides the novel intermediates of the formula X and salts thereof formed during ring opening and, optionally, deprotection, including all stereoisomers thereof, either substantially free of other stereoisomers, or in admixture with other selected, or all other stereoisomers.

Contact with Base to Form Taxanes of the Formula IV and Salts Thereof

Treatment of a compound of the formula X or salt thereof with a base provides a compound of the formula IV or salt thereof. Any base allowing migration of the acyl group —C(O)—R$^1$ to the amine group —NH$_2$, thereby effecting formation of a compound of the formula IV or salt thereof, may be employed in the method of the present invention. Exemplary bases include alkali metal bicarbonates such as sodium bicarbonate or potassium bicarbonate. Mole ratios of base: compound of formula X are preferably from about 1:1 to about 5:1.

The reaction is preferably conducted at a temperature of from about −20° C. to about 80° C. and at a pressure of 1 atm. The reaction is preferably conducted under an atmosphere of argon, nitrogen or air.

Solvents are preferably employed which are inert organic liquids alone or in admixture with water such as tetrahydrofuran, alcohols (preferably, lower alkanols such as methanol), toluene, acetonitrile, dioxane, or mixtures thereof. The amount of solvent employed preferably provides a loading of the compound of the formula X of from about 1 to about 5% by weight, based on the combined weight of solvent and formula X compound.

Deprotection of protected groups may be conducted simultaneously with, or subsequent to use of a base, although deprotection prior to contact with a base, especially simultaneously with ring opening, is preferably employed, as described above.

Separation

The products of the methods of the present invention may be isolated and purified, for example, by methods such as extraction, distillation, crystallization, and column chromatography.

Sidechain-bearing Taxane Products

The sidechain-bearing taxanes of the formula IV and salts thereof prepared by the methods of the present invention are themselves pharmacologically active, or are compounds which may be converted to pharmacologically active products. Pharmaco-logically active taxanes such as taxol may be used as antitumor agents to treat patients suffering from cancers such as breast, ovarian, colon or lung cancers, melanoma or leukemia. The utility of such sidechain-bearing taxanes has been described, for example, in European Patent Publication No. 400,971, U.S. Pat. No. 4,876, 399, U.S. Pat. No. 4,857,653, U.S. Pat. No. 4,814,470, U.S. Pat. No. 4,924,012, U.S. Pat. No. 4,924,011, U.S. Pat. No. 5,254,580, and U.S. Pat. No. 5,272,171, all incorporated herein by reference.

Taxotere, having the structure shown following, or especially taxol, having the structure shown above, are preferably ultimately prepared as the sidechain-bearing taxanes of the formula IV:

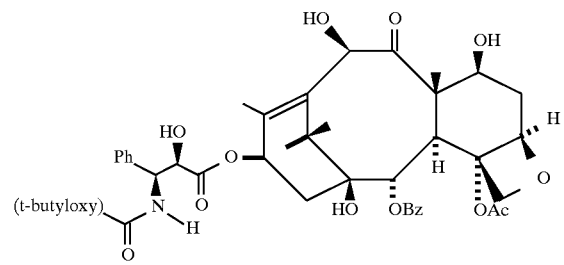

Solvates, such as hydrates, of reactants or products may be employed or prepared as appropriate in any of the methods of the present invention.

Also considered within the ambit of the present invention are the water soluble prodrug forms of the compounds of formula IV. Such prodrug forms of the compounds of formula IV are produced by introducing at C-7 or C-10 and/or at the 2'-position of the side chain a phosphonoxy group of the general formula —OCH$_2$(OCH$_2$)$_m$OP(O)(OH)$_2$ wherein m is 0 or an integer from 1 to 6 inclusive.

The novel prodrugs have the formula

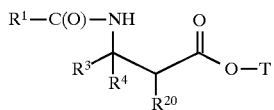

where
R$^1$ is R$^5$, R$^7$—O—, R$^7$—S—, or (R$^5$)(R$^6$)N—;
R$^3$ and R$^4$ are independently R$^5$, R$^5$—O—C(O)—, or (R$^5$)(R$^6$)N—C(O)—;
R$^5$ and R$^6$ are independently hydrogen, alkyl, alkenyl, alkynyl, cycloalkyl, cycloalkenyl, aryl or heterocyclo, and
R$^7$ is alkyl, alkenyl, alkynyl, cycloalkyl, cycloalkenyl, aryl or heterocyclo;
and T is

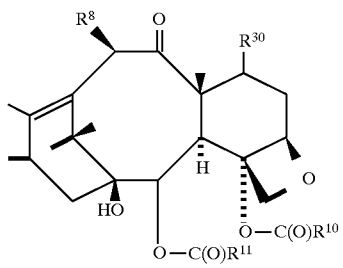

where
R$^8$ is hydrogen, hydroxyl, R$^{14}$—O—, R$^{15}$—C(O)—O—, R$^{15}$—O—C(O)—O—, or —OCH$_2$(OCH$_2$)$_m$OP(O)(OH)$_2$;
R$^{10}$ and R$^{11}$ are independently hydrogen, alkyl, alkenyl, alkynyl, cycloalkyl, cycloalkenyl, R$^{16}$—O—, aryl or heterocyclo;
R$^{20}$ is hydrogen, —OCH$_2$(OCH$_2$)$_m$OP(O)(OH)$_2$, —OC(O)R$^{21}$ or —OC(O)OR$^{21}$ wherein R$^{21}$ is C$_1$–C$_6$ alkyl optionally substituted with one to six halogen atoms, C$_3$–C$_6$ cycloalkyl, C$_2$–C$_6$ alkenyl or a radical of the formula

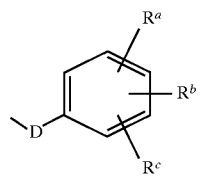

wherein D is a bond or C$_1$–C$_6$ alkyl and R$^a$, R$^b$ and R$^c$ are independently hydrogen, amino, C$_1$–C$_6$ mono- or di-alkylamino, halogen, C$_1$–C$_6$ alkyl or C$_1$–C$_6$ alkoxy;
R$^{14}$ is a hydroxy protecting group;
R$^{16}$ is alkyl;
R$^{30}$ is hydrogen, hydroxy, fluoro, —OCH$_2$(OCH$_2$)$_m$OP(O)(OH)$_2$ or —OC(O)OR$^{21}$ wherein R$^{21}$ is as above.
R$^{15}$ is hydrogen, alkyl, alkenyl, alkynyl, cycloalkyl, cycloalkenyl, aryl or heterocyclo;
m is 0 or an integer from 1 to 6 inclusive with the proviso that at least one of R$^8$, R$^{20}$ and R$^{30}$ is —OCH$_2$(OCH$_2$)$_m$OP(O)(OH)$_2$ and R$^{10}$ is not methyl and phosphonxy group base salts thereof.
Preferred compounds of formula IV' include those wherein R$^{10}$ is cycloalkyl or OME or OEt; R$^1$ is aryl, preferably phenyl or alkoxy preferably t-butyloxy; R$^3$ is aryl preferably phenyl or heterocyclo, preferably furyl or thienyl or alkenyl preferably propenyl or isobutenyl; R$^4$ is hydrogen; R$^8$ is hydroxy or alkylcarbonyloxy, preferably acetyloxy; R$^{11}$ is aryl preferably phenyl; R$^{20}$ is —OCH$_2$(OCH$_2$)$_m$OP(O)(OH)$_2$ or —OC(O)OR$^{21}$ wherein R$^{21}$ is ethyl or N-propyl; R$^{30}$ is —OCH$_2$(OCH$_2$)$_m$OP(O)(OH)$_2$ and m is 0 or 1.

The phosphonoxy group is normally introduced following synthesis of the end products of formula IV following procedures set forth in U.S. Ser. No. 08/1108,015 filed Aug. 17, 1993, now abandoned which is incorporated by reference herein.

In arriving at the novel prodrugs above, various novel intermediates are formed following the reaction conditions set forth generally in U.S. Ser. No. 08/1108,015. Compounds of formula IV are used as starting materials wherein non-desired hydroxy groups have been blocked. The appropriately protected compound of formula IV wherein reactive hydroxy groups are present either at the 2' or 7 or 10 positions or at multiple positions is first connected to a corresponding methylthiomethyl ether [—OCH$_2$(OCH$_2$)$_m$SCH$_3$]. Thereafter depending on the value of m, the ether may be connected to a protected phosphonooxymethyl ether by a variety of steps as set forth in the above U.S. Ser. No. The phosphono protecting group(s) and the hydroxy protecting groups may thereafter be removed by conventional techniques.

The free acid can then be converted to the desired base salt thereafter by conventional techniques involving contacting the free acid with a metal base or with an amine. Suitable metal bases include hydroxides, carbonates and bicarbonates of sodium, potassium, lithium, calcium, barium, magnesium, zinc, and aluminum; and suitable amines include triethylamine, ammonia, lysine, arginine, N-methylglucamine, ethanolamine, procaine, benzathine, dibenzylamine, tromethamine (TRIS), chloroprocaine, choline, diethanolamine, triethanolamine and the like. The base salts may be further purified by chromatography followed by lyophilization or crystallization.

The prodrugs may be administered either orally or parenterally following the teaching of the above patent application Ser. No. (08/1108,015). The compounds of Formula IV and IV' are novel antitumor agents showing in vitro cytotoxicity activity against human colon carcinoma cell lines HCT-116 and HCT-116/VM46 and M109 lung carcinoma.

The present invention is further described by the following examples which are illustrative only, and are in no way intended to limit the scope of the instant claims.

EXAMPLE 1

Preparation of (4S-trans)-4,5-Dihydro-2,4-diphenyl-5-oxazolecaboxylic acid, ethyl ester

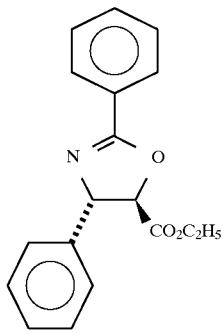

(2R,3S)-N-benzoyl-3-phenylisoserine ethyl ester (0.104 g, 0.332 mmoles) was added to an oven-dried 10 ml flask, purged with argon, and suspended in toluene (5.0 ml). Pyridinium p-toluene sulfonic acid (PPTS) (42 mg, 0.167 mmoles) was added. After stirring at room temperature for about 1 hour, the mixture was heated to reflux. A clear homogeneous solution was obtained upon heating. After about 1 hour of heating, the reaction mixture became cloudy. TLC after 16.5 hours of heating showed that the reaction was complete (1:1 ethyl acetate (EtOAc):hexane, PMA (phosphomolybdic acid)/ethanol, ultraviolet (U.V.)).

The reaction mixture was diluted with 10 ml of chloroform, washed with 5 ml of saturated aqueous NaHCO$_3$, dried over Na$_2$SO$_4$, filtered, and concentrated to give 97.8 mg of a yellowish oil (yield=100%). $^1$H NMR showed that the trans-oxazoline title product had been obtained with only minor (<<5%) impurities, none of which were the corresponding cis-oxazoline.

EXAMPLE 2

Preparation of (4S-trans)-4,5-Dihydro-2,4-dilphenyl-5-oxazolecarboxylic acid, ethyl ester

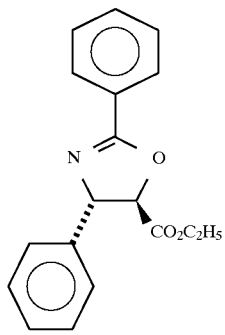

(2S,3S)-N-benzoyl-3-phenylisoserine ethyl ester (0.100 g, 0.319 mmoles) was added to a flame-dried, argon-purged, 5 ml flask, dissolved in pyridine (1.0 ml), and cooled to 0° C. Methyl sulfonyl chloride (38 mg, 0.335 mmoles) was added dropwise, and the yellowish solution was stirred at 0° C. for 1¾ hours, and then warmed to room temperature. Thin layer chromatography (TLC) after 1 ½ hours at room temperature showed the reaction to be complete (1:1 ethyl acetate:hexane, PMA/ethanol, U.V.).

The heterogeneous mixture was diluted with 5 ml ethyl acetate and washed with ⅓ saturated aqueous CuSO$_4$ (10 ml). The aqueous fraction was extracted with 2×5 ml ethyl acetate. The combined organic fractions were washed with 5 ml saturated aqueous NaCl, dried over Na$_2$SO$_4$, filtered, and concentrated to yield 0.12 g of a yellowish oil.

The title product was purified by silica gel chromatography (column: 20 mm d×50 mm l) with 1:1 ethyl acetate-:hexane to give 92.6 mg of a yellowish oil (yield=98.3%). $^1$H NMR and mass spec. showed that the trans-oxazoline title product was obtained. Specific rotations: (c=0.1, CHCl$_3$), $[\alpha]_D$=+15.6°, $[\alpha]_{578}$=+16.3°, $[\alpha]_{546}$=+18.7°, $[\alpha]_{436}$=+33.1°.

The starting compound (2S,3S)-N-benzoyl-3-phenylisoserine ethyl ester was prepared in a separate experiment as follows:

In a 500 ml flask containing a solution of (4S-cis)-4,5-dihydro-2,4-diphenyl-5-oxazolecarboxylic acid, ethyl ester (0.79 g, 2.67 mmol) in methanol (MeOH) (57 ml) at 0° C. was added 1N HCl (57 ml) with stirring over a 10 minute period. A precipitate was formed during the HCl addition which dissolved during the addition of tetrahydrofuran (THF). THF (57 ml) was then added to clear the solution, and the resulting mixture was stirred at 0° C. for 2 hours and 15 minutes. The pH of the solution was adjusted to 9.0 with saturated NaHCO$_3$ (120 ml) and then the mixture was allowed to stir at room temperature for 18 hours. (The reaction was monitored by TLC (silica gel) using 4:6 EtOAc:Hexane as eluent, R$_f$ for the starting material=0.71, R$_f$ for the product=0.42, UV visualization).

The reaction was diluted with EtOAc (200 ml) and the aqueous layer was separated and extracted with EtOAc (100 ml ×1). The combined EtOAc solution was then washed with brine (150 ml ×1), dried over Na$_2$SO$_4$, filtered and concentrated to give crude (2S,3S)-N-benzoyl-3-phenylisoserine ethyl ester as a solid (0.810 g). It was dissolved in hot MeOH (15 ml) and set aside at room temperature for 30 minutes and then at 4° C. for 1 hour. The solid was filtered, washed with cold MeOH (2 ml) and dried in vacuo to give 0.43 g of (2S,3S)-N-benzoyl-3-phenylisoserine ethyl ester as the first crop. A second crop (0.24 g) was also obtained as above to give a total of 0.67 g (80%) of (2S,3S)-N-benzoyl-3-phenylisoserine ethyl ester. (white solid: mp=160°–161° C., $[\alpha]_D$=–40.3° (c 1, CHCl$_3$).

| Elemental Analysis $C_{18}H_{19}NO_4 \cdot 0.03H_2O$ | | |
|---|---|---|
| | Calc. | Found |
| C | 68.86 | 68.99 |
| H | 6.12 | 6.07 |
| N | 4.46 | 4.60 |
| H$_2$O | 0.20 | 0.20 |

EXAMPLE 3

Preparation of (4S-trans)- and (4S-cis)-4,5-Dihydro-2,4-diphenyl-5-oxazolecarboxylic acid, ethyl esters

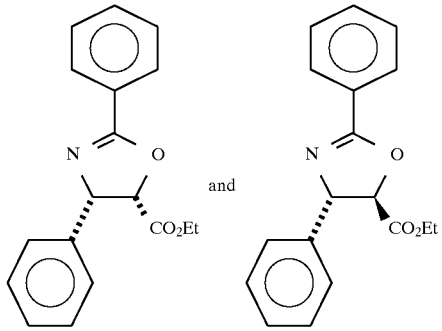

(2S,3S)-N-benzoyl-3-phenylisoserine ethyl ester (66.8 mg, 0.213 mmoles) was added to an oven-dried 10 ml flask, purged with argon, and suspended in toluene (4.0 ml). Pyridinium p-toluene sulfonic acid (49 mg, 0.195 mmoles) was added. The flask was equipped with a Dean-Stark trap (filled with 4 angstrom molecular sieves). The reaction was heated to reflux (most of the solids dissolved upon heating). TLC at 5 hours showed that the reaction was nearly complete (1:1 EtOAc:hexanes, PMA/EtOH, U.V.).

The reflux was allowed to continue overnight. After 22 hours of heating, the reaction was cooled to room temperature. Some oily substance dropped out of solution. This oil solidified upon further cooling to room temperature. The solid did not appreciably dissolve upon the addition of ~5 ml EtOAc. ~3 ml CHCl₃ were added to dissolve all solid material. TLC showed no starting material.

The solution was then washed with 5 ml saturated aqueous NaHCO₃, dried over Na₂SO₄, filtered, and concentrated to yield 64.3 mg of a partially crystallized yellow oil. $^1$H and $^{13}$C NMR showed cis-oxazoline title product: trans-oxazoline title product: impurity in a ~5:trace:1 ratio. The trans-oxazoline title product was attributed to a trace amount of (2R,3S)-N-benzoyl-3-phenylisoserine ethyl ester present in the starting material. The product was chromatographed on silica get with 1:1 EtOAc/Hexane 2:1 EtOAc/Hexane, ($R_f$=0.57 (1:1 EtOAc:hexanes) to give 49.3 mg of an oily yellowish solid, yield=78.4%; $^1$H NMR showed the cis and trans oxazoline title products in about a 10:1 ratio (cis:trans).

EXAMPLE 4

Preparation of (AS-trans)-4, 5-Dihydro-2.4-diphenyl-5-oxazolecarboxylic acid, methyl ester (a) Benzenecarboximidic acid, ethyl ester, hydrochloride

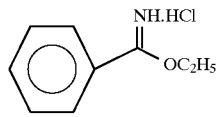

Benzonitrile (30.3 g, 294 mmoles) and ethanol (14.2 g, 308 mmoles) were added to a flame-dried, argon purged 100 ml flask and cooled to 0° C. HCl was bubbled through the stirring solution for 20 minutes, by which time the tare showed that 17.5 g HCl had been added. HCl addition was ceased and the clear solution was stirred at 0° C. A precipitate began to form after about 1 hour.

After stirring at 0° C. for about 2½ hours, the heterogeneous mixture was transferred to a 4° C. cold room. After 3½ days at 4° C, the solid mass was crushed and triturated with 150 ml of cold 4° C. diethyl ether. The mixture was allowed to stand at 4° C. for 6 hours. The mixture was vacuum-filtered and quickly washed with 2×100 ml cold diethyl ether and dried under high vacuum (0.5 mm Hg for 17 hours) to give 51.6 g (94.5%) of a white free flowing powder of the title product.

(b) (4S-trans)-4,5-Dihydro-2,4-diphenyl-5-oxazolecarboxylic acid, methyl ester

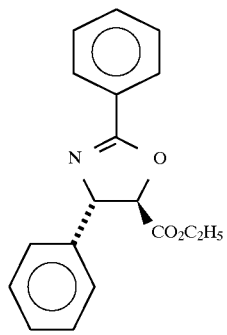

(2R,3S)-3-Phenylisoserine methyl ester hydrochloride salt (5.76 g, 24.9 mmoles) was dissolved in 1,2-dichloroethane (75 ml). Triethylamine (2.77 g, 27.3 mmoles) was added and the resulting mixture was stirred for 15 minutes before the addition of the benzimidate prepared in step (a) above (4.62 g, 24.9 mmoles) in one portion. The mixture was stirred for 10 minutes, then heated to reflux. TLC after 4 ½ hours of reflux showed the reaction to be complete. (1:1 ethyl acetate/hexane, PMA/ethanol, U.V.)

The reaction mixture was diluted with 150 ml dichloromethane and 150 ml 10% K₂CO₃ and shaken. The layers were separated, and the aqueous fraction extracted with 3×50 ml CH₂Cl₂. The combined organic fractions were washed with 50 ml saturated aqueous NaCl, dried over Na₂SO₄, filtered and concentrated to give a yellow oil which was purified on a silica gel column (dry volume~750 ml; packed column: 100 mm d×110 mm l) with 1:2 ethyl acetate/hexane to give 6.05 g of the title product as a very slightly colored oil which solidified upon standing at room temperature. Yield=86.4%.

EXAMPLE 5

Preparation of (4S-cis)-4,5-Dihydro-2,4-diphenyl-5-oxazolecarboxylic acid, ethyl ester

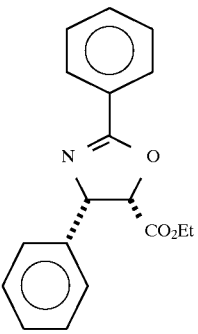

In a 100 ml flask containing a solution of (2R,3S)-N-benzoyl-3-phenylisoserine ethyl ester (2.00 g, 6.38 mmol) in pyridine (20 ml) at 0° C. was added methanesulfonyl chloride (0.52 ml, 6.70 mmol) dropwise over a 2 minute period. The solution was stirred at 0° to 4° C. for 90 minutes and then at 65°–70° C. for 18 hours. (The reaction was monitored by TLC using 1:2 EtOAc:Toluene as eluent, $R_f$ for the starting material=0.42, $R_f$ for the mesylate=0.48 and $R_f$ for the cis-oxazoline title product=0.78, UV visualization.)

The reaction was cooled down to room temperature and diluted with EtOAc (80 ml) and ⅓ saturated CuSO₄ solution (80 ml) (⅓ saturated CuSO₄ solution was prepared by diluting saturated CUSO₄ solution to ⅓ its original concentration). The aqueous layer was separated and extracted with EtOAc (40 ml×1). The combined EtOAc solution was then washed with brine (80 ml×1), dried over Na₂SO₄, filtered, concentrated and azeotroped with heptane (20 ml ×2) to give crude cis oxazoline title product as a solid (1.88 g). It was dissolved in hot EtOAc (8 ml) and then hexane (4 ml) was added. The crystallizing mixture was set aside at room temperature for 20 minutes and then at 4° C. for 30 minutes. The solid was filtered, washed with cold 10% EtOAc in hexane and air dried to give 1.34 g (71.3%) of the cis-oxazoline title product having a melting point of 135° C. $[a]_D$=–9.25 (c=1.0, CHCl₃).

EXAMPLE 6

Preparation of (4S-trans)-4,5-Dihydro-2,4-diphenyl-5-oxazolecarboxylic acid

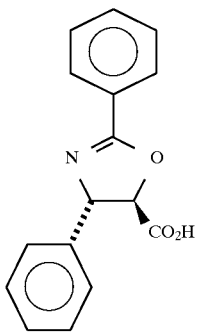

(4S-trans)-4,5-Dihydro-2,4-diphenyl-5-oxazolecarboxylic acid, ethyl ester (92 mg, 0.311 mmoles) was transferred to a 1 dram vial and dissolved in tetrahydrofuran (THF) (0.8 ml). LiOH (aq., 1 N, 0.343 mmoles) was added dropwise and the resulting biphasic mixture was stirred vigorously at room temperature. Within 5 minutes, a homogeneous solution was obtained. TLC after 45 minutes showed no starting material (1:1 ethyl acetate (EtOAc)/Hexane, PMA/ethanol (EtOH), U.V).

The solution was cooled to 0° C. and further diluted with 2.0 ml THF. The reaction was quenched with 0.34 ml of 1N HCl (1.1 eq). After warming to room temperature, the solution was diluted with 5 ml EtOAc and 5 ml $H_2O$ and shaken. The layers were separated. The aqueous fraction was extracted with 3×5 ml EtOAc. (After extractions, aqueous fraction pH ~6). The combined organic fractions were dried over $Na_2SO_4$, filtered and concentrated to give 72.1 mg of a white solid. Yield=87%. $^1H$ and $^{13}C$ NMRs, and Mass. Spec. showed the title product having a melting point of 201°–203° C. $[a]_D$=+25.6°, $[a]_{578}$ =+26.9°, $[a]_{546}$ =+30.7° $[a]_{436}$=+53.8° (c=1.0 $CHCl_3$: $CH_3OH$ (1:1)).

EXAMPLE 7

Preparation of (4S-trans)-4,5-Dihydro-2,4-diphenyl-5-oxazolecarboxylic acid

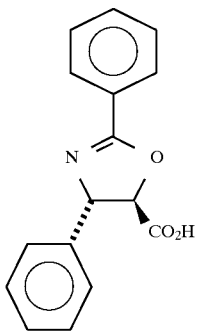

(4S-trans)-4,5-Dihydro-2,4-diphenyl-5-oxazolecarboxylic acid, methyl ester (0.509 g, 1.81 mmoles) was added to a 10 ml flask and dissolved in tetrahydrofuran (THF) (4.7 ml). Lithium hydroxide (1N in $H_2O$, 2.0 ml, 1.99 mmoles) was added dropwise. The biphasic mixture was stirred vigorously. Within 2 minutes after completion of the lithium hydroxide addition, a clear solution was obtained. TLC after 15 minutes showed that the reaction was complete (1:1 ethyl acetate:hexane, PMA/ethanol).

The reaction mixture was further diluted with 10 ml THF and the resulting cloudy solution cooled to 0° C. The reaction was quenched by dropwise addition of 2.0 ml of 1N aqueous HCl. The solution was further diluted with 20 ml ethyl acetate and 15 ml water and shaken. The layers were separated, and the aqueous fraction extracted with 3×10 ml ethyl acetate (pH of the aqueous layer after extractions was approximately 6). The combined organic fractions were dried over $Na_2SO_4$ filtered, and concentrated. The concentrate obtained was soluble in a mixture of benzene and methanol, and less soluble in methanol, $CHCl_3$, ethyl acetate or a mixture of these. The concentrate was dried on high vacuum overnight to yield 0.448 g of the title product as a white solid. (Yield=93%). M.P.=201–203°. $[a]D$=+25.6, $[a]_{578}$=+26.9°, $[a]_{546}$=+30.7, $[a]_{436}$=+53.8°, (c=1.0, $CHCl_3$: $CH_3OH$ (1:1)).

EXAMPLE 8

Preparation of (4S-trans)-4,5-Dihydro-2,4-diphenyl-5-oxazolecarboxylic acid

Ethanol (0.1 ml) was mixed with tetrahydrofuran (1.0 ml), and the mixture cooled to −78° C. n-Butyllithium (n-BuLi) (2.12M, 0.050 ml) was added dropwise, and the mixture warmed to 0C. Solid (4S-cis)-4,5-dihydro-2,4-diphenyl-5-oxazolecarboxylic acid, ethyl ester having the structure;

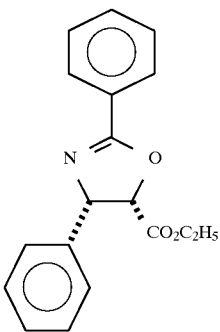

(20 mg, 0.0678 mmol) was added and the reaction was stirred for 1 hour (a small amount of water was present). A mixture of cis oxazoline ethyl ester starting material and the corresponding trans oxazoline ethyl ester (5-position inversion) were observed by TLC (very little hydrolysis was noted at this point). The reaction mixture was stirred for another hour and then left with an ice bath overnight (0° C. to room temperature). After 18 hours TLC showed mostly the trans acid title product and a trace of the cis ester starting material (solvent systems hexane:EtOAc 2:1 (trace of cis ester) and EtOAc:acetone:$H_2O$:MeOH 7:1:1:1 (title product)).

The reaction was quenched with phosphate (pH=4.3) buffer, and extracted with ethyl acetate (5×10 ml). The organic layer was dried and solvent removed to give ~17 mg (93%) of the title product. (NMR showed the trans acid title product). M.P.=135° C. $[a]_D$+−92.5°, (c=1.0, $CHCl_3$).

EXAMPLE 9

Preparation of (4S-trans)- and (4S-cis)-4,5-Dihydro-2,4-diphenyl-5-oxazolecarboxylic acids

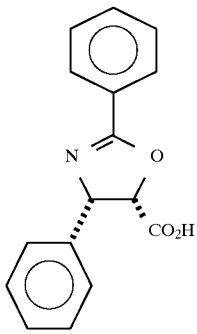

and

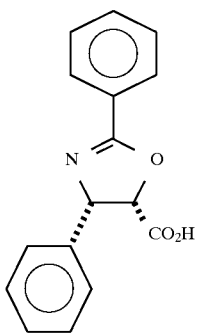

(4S-cis)-4,5-dihydro-2,4-diphenyl-5-oxazolecarboxylic acid, ethyl ester (202 mg, 0.6890 mmoles) was dissolved in tetrahydrofuran (1.5 ml) and lithium hydroxide (1 N aq., 0.718 ml) was added dropwise. A heterogeneous solution was observed. The reaction mixture was stirred overnight at room temperature, upon which time the solution was clear. (TLC (ethyl acetate: hexane, 1:1) showed a small amount of starting material. TLC (ethyl acetate:methanol:water:acetone 7:1:1:1) showed the cis and trans oxazoline title products). 1 N HCl (0.718 ml) was added, followed by saturated NaCl (approximately 10 ml) and ethyl acetate (approximately 10 ml). The water layer was washed with ethyl acetate 5 times (approximately 10 ml) and the H$_2$O layer which had a pH of ~5.5 was further acidified to 3.4 pH and extracted with approximately 10 ml EtOAc. The combined organic layers were dried over MgSO$_4$, and filtered. The ethyl acetate was evaporated under reduced pressure to yield 183 mg (100%) of a mixture of cis and trans title products (3:1, cis:trans by $^1$H NMR).

EXAMPLE 10

Preparation of 7-Triethylsilyl 13-[[(4S-trans)-4,5-dihydro-2,4-diphenyl-5-oxazolyl]-carbonyl]baccatin III (a) 7-Triethylsilyl baccatin III (i) [2aR-(2aα,4β,4aβ,6β9α,11β,12α, 12aα,12bα)]-Benzoic acid, 12b-acetyloxy-2a,3,4,4a,5,6,9,10,11,12,12a.12b-dodecahydro-6,9,11-tri-hydroxy-4a 8,13,13-tetramethyl-5-oxo-4-[(triethylsilyl)oxy]-7, 11-methano-1H-cyclo-deca[3,4]benz[1,2-b]oxet-12-yl ester

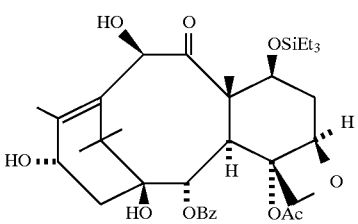

10-Desacetylbaccatin III (27.4 g, 50.3 mmol, containing H$_2$O: 1.57%, CH$_3$OH: 1.6%, ethyl acetate: 0.09%, and hexane: 0.03%), and 4-dimethylaminopyridine (2.62 g, 21.4 mmol, wt. % H$_2$O (Karl Fisher ("K.F.")=0.09) were added to a flame-dried, argon-purged 1L 3-necked flask (equipped with a mechanical stirrer and a digital thermometer) and were dissolved in dry dimethylformamide (122 ml, wt. % H$_2$O (K.F.)=<0.01). Methylene chloride (256 ml, wt. % H$_2$O (K.F.)=<0.01) was added (the temperature of the reaction solution rose from 23° C. to 25° C. during the addition of the methylene chloride) and the resulting homogeneous solution was cooled to -50° C.

Triethylamine (16 ml, 120 mmol, wt. % H$_2$O (K.F.)=0.08) was added dropwise over 3 minutes and the resulting solution was stirred at -50° C. for 5 minutes before the dropwise addition of neat triethylsilyl chloride (18.6 ml, 111 mmol). The addition of triethylsilyl chloride was conducted over a period of 10 minutes during which the temperature of the reaction did not rise above -50° C. The reaction became very cloudy during the addition of triethylsilyl chloride.

The resulting mixture was stirred at about -50° C. for 1 hour and was then allowed to stand (without stirring) in a -48° C. freezer for 22 hours. (A separate experiment showed that stirring the reaction at -48° C. for 8 hours resulted in ~60% conversion). The mixture was then removed from the freezer and warmed to about -10° C. TLC analysis of the mixture (solvent: ethyl acetate, stain: phosphomolybdic acid/ethanol) revealed the absence of starting material and showed a single spot for the product (R$_f$ =0.60). The cold mixture was combined with EtOAc (1L) and washed with H$_2$O (890 ml).

The resulting aqueous layer was separated and extracted with EtOAc (250 ml). The combined organic layers were washed with 5.7% aqueous NaH$_2$PO$_4$ (2×250 ml, measured pH of 5.7% aqueous NaH$_2$PO$_4$ =4.30±0.05, measured pH of the combined NaH$_2$PO$_4$ washings=5.75±0.05), half-saturated aqueous NaCl (250 ml), saturated aqueous NaCl (250 ml), dried over Na$_2$SO$_4$, filtered and concentrated on a rotovap. (All concentrations on the rotovap of this Example were conducted with a water bath temperature of 35° C.)

The resulting semi-solid was further dried by exposure to high vacuum (~1 mm Hg for 20 minutes) to give 41.5 g of a white solid. The crude product was then dissolved in CH$_2$Cl$_2$ (400 ml) (heating in a 35° C. water bath was employed to dissolve the solid), and the volume of the resulting solution was reduced to ~150 ml on a rotovap. Crystallization started immediately and the mixture was allowed to stand at room temperature for 1 hour. Hexanes (100 ml) were added and the mixture was gently swirled. The mixture was allowed to stand in a 4° C. cold room for 16.5 hours. The solid was filtered, washed with 1:9 CH$_2$Cl$_2$/hexanes (3×250 ml) on a suction filter, and dried under high vacuum (~0.2 mm Hg for 42 hours) to give 26.1 g (79%) of the title product as a white powder. The mother liquor was concentrated on a rotovap, and the residue was crystallized from CH$_2$Cl$_2$ to give 4.5 g (14%) of the title product as white crystals. Recrystallization was conducted in the same manner as with the first crop of product: the solid was dissolved in CH$_2$Cl$_2$ (100 ml) without heating, and the volume of the resulting solution was reduced to ~7 ml on a rotovap. Crystallization began within 5 minutes. The mixture was allowed to stand at room temperature for 1 hour, then in a 4° C. cold room for 42 hours. The crystals were filtered, washed with 1:9 CH$_2$Cl$_2$/hexanes (3×50 ml) on a suction filter, and dried under high vacuum (~0.2 mm Hg for 18 hours). The $^1$H NMR of this crop was identical to the $^1$H NMR of the first crop of product. The combined yield for the two crops was 93% (uncorrected).

| | Elemental Analysis (%) $C_{35}H_{50}O_{10}Si$ | |
|---|---|---|
| | Calcd. | Found |
| C | 63.80 | 63.43 |
| H | 7.65 | 7.66 |
| KF(H$_2$O) | 0.00 | 0.00 | m.p.: 239°–242° C. (decomp.); $[\alpha]^{22}_D$: −53.6° (c 1.0, CHCl$_3$); TLC:R$_f$=0.60 (silica gel, EtOAc) Visualized by phosphomolybdic acid/ethanol.
(ii) [(2aR-(2aα,4β,4aβ,6β9α, 11β, 12α, 12aα, 12bα)]-6,12b-Bis(acetyloxy)-12-(benzoyloxy)-2a-3,4,4a,5,6,9,10,11,12,12a,12b-dodecahydro-9,11-dihydroxy-4a,8,13,13-tetramethyl-4-[(triethylsilyl)oxy]-7,11-methano-1 H-cyclodeca[3.4]benz[1,2-b]-oxet-5-one (7-triethylsilyl baccatin III

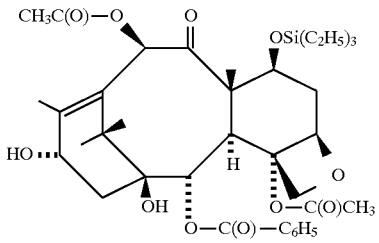

The title product from step (i) above (21.4 g, 32.4 mmol) was added to a flame-dried, argon purged 1 L 3-necked flask (equipped with a mechanical stirrer and a digital thermometer) and dissolved in THF (350 ml, freshly distilled from sodium/benzophenone). The resulting solution was cooled to −70° C. A solution of n-butyllithium (n-BuLi) (14.6 ml of a 2.56M solution in hexanes, 37.3 mmol, titrated in triplicate with diphenylacetic acid in THF at 0° C.) was added dropwise over a period of 23 minutes. The temperature of the reaction did not rise above −68° C. during the addition. Solids were formed upon the addition of n-BuLi and did not appear to dissolve at −70° C. The resulting mixture was stirred at −70° C. for 20 minutes and was then warmed to −48° C. A clear homogeneous solution was obtained upon warming to −48° C.

After stirring at −48° C. for ½ hour, acetic anhydride (4.6 ml, 49 mmol, distilled (137°–138° C., 1 atm) under an atmosphere of argon before use) was added dropwise over 7 minutes. The temperature of the reaction did not rise above −45° C. during the addition. The resulting solution was stirred at −48° C. for 20 minutes and then at 0° C. for 1 hour. The solution was diluted with ethyl acetate (350 ml), washed with saturated aqueous NH$_4$Cl (250 ml), and the layers were separated. The aqueous layer was extracted with ethyl acetate (200 ml). The combined organic layers were washed with saturated aqueous NaCl, dried over Na$_2$SO$_4$, filtered and concentrated on a rotovap. (All concentrations on the rotovap in this Example were conducted with a water bath temperature of 35° C.) Exposure of the semi-solid to high vacuum (~1.5 mm Hg for ½ hour) gave 24.7 g of a white solid.

The crude product was dissolved in CH$_2$Cl$_2$ (300 ml) and the volume of the resulting solution was reduced to ~70 ml on a rotovap. Crystallization began within one minute. The mixture was allowed to stand at room temperature for 45 minutes and then in a 4° C. cold room for 18 hours. The crystals were filtered, washed with 1:9 CH$_2$Cl$_2$/hexanes (3×100 ml) on a suction filter, and dried under high vacuum (~0.2 mm Hg for 19 hours) to give 20.9 g (92.0%) of the title product as fine white needles. The mother liquor was concentrated on a rotovap, and the residue was crystallized from CH$_2$Cl$_2$/hexanes to give 0.82 g (3.6%) of the title product as small white crystals.

Crystallization of the mother liquor was conducted as follows: The residue was dissolved in CH$_2$Cl$_2$ (10 ml) and the volume of the resulting solution was reduced to ~5 ml on the rotovap. After standing at room temperature for ½ hour, no crystals had formed. Hexanes (5 ml) were added in 1 ml portions and the solution was swirled. A few crystals were present by this time. The mixture was allowed to stand at room temperature for ½ hour (more crystals formed) and then in a 4° C. cold room for 18 hours. The crystals were filtered, washed with 1:9 CH$_2$Cl$_2$/hexanes on a suction filter, and dried under high vacuum (~0.15 mm Hg for 21 hours). The combined yield for the two crops was 95.6%. m.p.= 218°–219° C. (decomp.); $[\alpha]^{22}_D$+−78.4° (c 1.0, CHCl$_3$); TLC:R$_f$=0.37 (silica gel, 1:9 acetone: CH$_2$Cl$_2$, visualized by phosphomolybdic acid/ethanol).
(b) 7-Triethylsilyl 1 3-[[(4S-trans)-4,5-dihydro-2,4-diphenyl-5-oxazolyl]-carbonyl]baccatin III

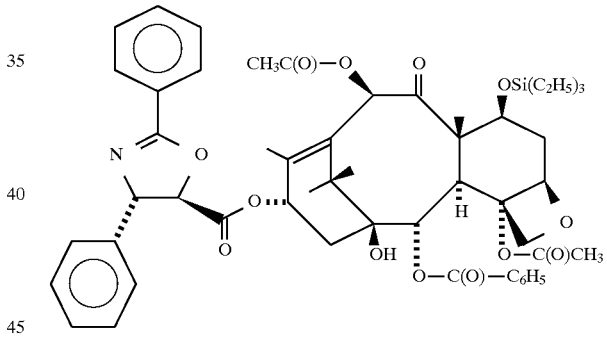

7-Triethylsilyl baccatin III prepared in step (a) above (0.209 g, 0.298 mmoles), the oxazoline prepared as the title product of Example 6 (80.2 mg, 0.300 mmoles), dicyclohexylcarbodiimide (DCC) (84 mg, 0.407 mmoles), and 4-dimethylaminopyridine (DMAP) (25 mg, 0.205 mmoles) were added to a 1 dram vial (oven-dried), purged with argon, and suspended in toluene (1.0 ml). After stirring for 1 hour at room temperature, some of the solid had dissolved and the mixture was a yellowish color. The heterogeneous mixture was heated to 85° C. TLC at 2 ½ hours showed the presence of starting material (1:1 ethyl acetate:hexane, PMA/ethanol, U.V.). Heating at 85° C. was continued. TLC at 5 hours looked essentially the same. The reaction was allowed to stir at room temperature overnight. After 14 hours at room temperature, TLC remained the same. The heterogeneous mixture was diluted with 1.0 ml ethyl acetate (some precipitate was noted) and the mixture was filtered through a pad of Celite. The Celite was rinsed with 3×1 ml ethyl acetate, and the filtrate was concentrated to give 0.349 g of a yellowish solid. $^1$H NMR showed that the title product and 7-triethylsilyl baccatin III were present in an approximately 8:1 ratio, respectively; some 1,3-dicyclohexylurea (DCU), and a trace of either the starting oxazoline or an impurity were also noted.

The mixture was partially separated on silica gel (column: 20 mm diameter ×90 mm length) with 1:2 ethyl acetate/hexane to 1:1 ethyl acetate/hexane. During chromatography, TLC analysis revealed a small spot with a slightly lower $R_f$ than the coupled title product. The mixed fractions of this impurity and the coupled product were combined. First spot: coupled title product (0.267 g of an off-white solid, yield= 94%.) ($^1$H NMR showed an approximately 18:1 ratio of the desired coupled product and the aforementioned impurity); first spot and aforementioned mixed fractions: 11.5 mg of an oil ($^1$H NMR showed an approximately 2:1 ratio of the desired coupled product and a different impurity). M.P.= 139°–142° C. $[a]_D$+−49.5°, $[\alpha]_{578}$ =−52.6°, $[\alpha]_{546}$ +−63.5°, $[\alpha]_{436}$=−157.0°, (c=1.0, CHCl$_3$),

EXAMPLE 11

Preparation of 7-Triethylsilyl 1 3-[[(4S-trans)-4,5-dihydro-2, 4-diphenyl-5-oxazolyl]-carbonyl]baccatin III

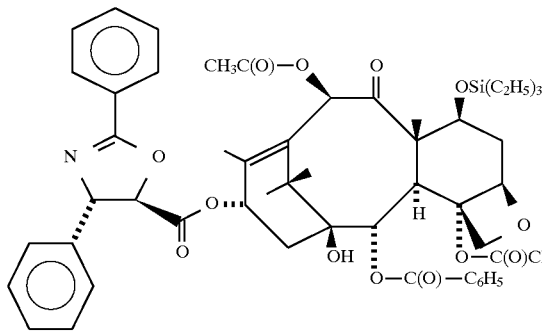

(4S-trans)-4,5-Dihydro-2,4-diphenyl-5-oxazolecarboxylic acid (96.0 mg, 0.359 mmoles), 7-triethylsilyl baccatin III (0.252 g, 0.359 mmoles), and 4-dimethylaminopyridine (DMAP)(30 mg, 0.246 mmoles) were added to a flame-dried 1 dram vial, purged with argon and suspended in toluene (1.2 ml). Diisopropylcarbodiimide (DIC)(63 mg, 0.503 mmoles) was immediately added, and the slightly yellowish heterogeneous mixture was stirred at room temperature. As time progressed, a very cloudy yellow solution resulted. At this point, the vial was seated and immersed in an 80° C. oil bath. After 3 hours at ~80° C., a darker orangish solution was obtained. The reaction mixture was directly concentrated. $^1$H NMR showed ~6:1 ratio of the desired coupled product and 7-triethylsilyl baccatin III. The product was partially purified by silica gel chromatography with 1:3 EtOAc/Hexane to give 0.300 g of an off-white solid. TLC showed isolated product and diisopropyl urea by-product.

$^1$H NMR showed only the desired coupled product and an impurity in ~25:1 ratio, and diisopropyl urea by-product. The ratio of desired coupled product to the diisopropyl urea by-product was ~12:1.

From these results, the yield of the desired coupled product was ~85%. M.P.=139°–142° C. $[\alpha]_D$+−49.5°, $[\alpha]_{578}$=−52.6°, $[\alpha]_{546}$=−63.5°, $[\alpha]_{436}$=−157.0°, (c=1.0, CHCl$_3$).

EXAMPLE 12

Preparation of 7-Triethylsilyl 13-[[(4S-trans)-4,5-dihydro-2,5-diphenyl-5-oxazolyl ]-carbonyl]baccatin III 7-Triethylsilyl baccatin III (abbreviated as "A" in this Example) and (4S-trans)-4,5-dihydro- 2,4-diphenyl-5-oxazolecarboxylic acid (abbreviated as "B" in this Example) were contacted under the conditions set forth in the following Table 1 to prepare the title compound. M.P.=139°–142° C. $[\alpha]_D$=−49.5°, $[\alpha]_{578}$=−52.6°, $[\alpha]_{546}$=−63.5°, $[\alpha]_{436}$=−157.0°, (c=1.0, CHCl$_3$).

TABLE 1

| Example No. | B (eq.)* | Reagents (eq.)* | Solvent | Concentration B (M) | Time (hrs) | Temp. (°C.) |
|---|---|---|---|---|---|---|
| 12a | 1.2 | DCC (1.4) DMAP (0.7) | PhCH$_3$ | 0.29 | 1 2.5 | 23 85 |
| 12b | 1.0 | DCC (1.4) DMAP (0.7) | PhCH$_3$ | 0.30 | 5.5 | 85 |
| 12c | 1.0 | R$_2$POCl (1.04) DMAP (1.01) NEt$_3$ (1.04) | 1,2-DCE | 0.28 | 6 15 | 23 55 |
| 12d | 1.0 | R$_2$POCl (1.01) NEt$_3$ (2.0) | 1,2-DCE | 0.23 | 5 16 44 | 23 65 75 |
| 12e | 1.0 | CDl (1.2) DMAP (1.0) | THF | 0.39 | 21 | 70 |
| 12f | 1.0 | ArCOCl (1.5) DMAP (2.0) NEt$_3$ (1.5) | CH$_2$Cl$_2$ | 0.23 | 23 | 23 |
| 12g | 1.0 | ArCOCl (1.5) DMAP (2.0) NEt$_3$ (1.5) | PhCH$_3$ | 0.29 | 5.5 | 23 |
| 12h | 1.0 | ArCOCl (1.05) DMAP (2.0) NEt$_3$ (1.0) | CH$_2$Cl$_2$ | 0.30 | 3.5 19 1 20 | −78 −60 0 23 |
| 12i | 1.0 | t-BuCOCl (1.1) DMAP (2.0) NEt$_3$ (1.2) | 1,2-DCE | 0.28 | 4.5 15 | 23 60 |
| 12j | 2.1 | t-BuCOCl(2.1) DMAP (4.2) NEt$_3$ (2.3) | 1,2-DCE | 0.23 | 21 | 23 |
| 12k | 1.0 | t-BuCOCl (1.0) DMAP (0.07) NEt$_3$ (2.0) | CH$_2$Cl$_2$ | 0.24 | 19 | 23 |
| 12l | 1.0 | t-BuCOCl(1.0) DMAP (0.05) | Pyridine | 0.23 | 4.5 16 23 | 23 55 23 |

* eq. = equivalents, based on 7-triethyl-silylbaccatin III (amounts of 7-triethylsilyl baccatin III were the following for the above Examples: 12a = 0.061 g; 12b = 0.533 g; 12c = 0.200 g; 12d = 0.161 g; 12e = 0.057 g; 12f = 0.200 g; 12g = 0.203 g; 12h = 0.208 g; 12i = 0.196 g; 12j = 0.165 g; 12k = 0.165 g; 12l = 0.164 g)

Key to Table 1

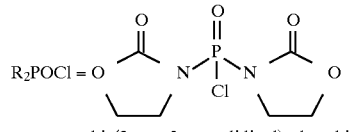

R$_2$POCl = O = bis(2-oxo-3-oxazolidinyl)-phosphinic chloride

DCC = dicyclohexylcarbodiimide
DMAP = 4-dimethylaminopyridine
DIC = diisopropylcarbodiimide
ArCOCl = 2,4,6-trichlorobenzoyl chloride =

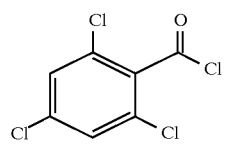

CDl = carbonyl diimidazole
t-BuCOCl = pivaloyl chloride
1,2-DCE = 1,2-dichloroethane
NEt$_3$ = triethylamine
THF = tetrahydrofuran
PhCH$_3$ = toluene

Example 12a

All reagents were mixed together before addition of the solvent. 108% (90 mg) of the title product was isolated by chromatography (containing about 10% of an impurity). Starting compound A was not visible by NMR. (Concentration of B in this Example was 0.29M. A separate experiment wherein DCC (2.0 eq), DMAP (3.0 eq.), DMAP.HCl (2.0 eq.) in CHCl₃ and 1.0 eq. of B was employed demonstrated that a molar concentration of 0.07M B did not allow the reaction to proceed rapidly enough to observe the formation of the title product by NMR in 27 hours.)

Example 12b

All reagents were mixed together before addition of the solvent. The title product was obtained in about a 9:1 ratio to the starting compound A (by NMR). 87% (0.63 g) of the title product was isolated by chromatography.

Example 12c

All reagents were mixed together before addition of the solvent. The title product was obtained in about a 1:1 ratio to the starting compound A (by NMR). No further reaction progress was noted after 1 hour.

Example 12d

Activated oxazoline B was allowed to form for 1 hour (by addition of R₂POCl to starting compound B) before addition of starting compound A. The title product was obtained in about a 1:6 ratio to the starting compound A (by NMR). Little reaction progress was noted after 5 hours.

Example 12e

CDI and the starting compound B were contacted for 1 hour before addition of the starting compound A. DMAP was added at t=4 hours. About a 1:1:1 ratio of the title compound to the starting material A and an impurity was obtained (by NMR). It was noted that no reaction occurred before addition of the DMAP, and that excessive heating caused some decomposition.

Example 12f

ArCOCl was added last. About a 1:1 ratio of the title product to the starting compound A was obtained (by NMR). No further reaction progress was noted after 1.5 hours.

Example 12g

ARCOCl was added last. About a 1:1 ratio of the title product to the starting compound A was obtained (by NMR). No further reaction progress was noted after 1 hour.

Example 12h ArCOCl was added last. About a 1:1 ratio of the title product to the starting compound A was obtained (by NMR). No further reaction progress was noted after 3.5 hours.

Example 12i

A mixed anhydride was preformed for 1 hour (by addition of t-BuCOCl to starting compound B) before addition of the starting compound A. About a 1:2 ratio of the title product to the starting compound A was obtained (by NMR). No further reaction progress was noted after 2 hours.

Example 12j

A mixed anhydride was preformed for 1 hour (by addition of t-BuCOCl to starting compound B) before addition of the starting compound A. About a 3:1 ratio of the title product to the starting compound A was obtained (by NMR). No further reaction progress was noted after 1 hour.

Example 12k

A mixed anhydride was preformed for 1 hour (by addition of t-BuCOCl to starting compound B) before the addition of the starting compound A. DMAP was added 1 hour after the starting compound A. About a 1:4 ratio of the title compound to the starting compound A was obtained (by NMR). No reaction was observed without DMAP; no further reaction progress was noted after 2 hours after DMAP addition.

Example 12l

A mixed anhydride was preformed for 1 hour (by addition of t-BuCOCl to starting compound B) before addition of the starting compound A. DMAP was added after 16 hours at 55° C. About a 1:6 ratio of the title product to the starting compound A was obtained (by NMR). No or very little reaction was observed before addition of the DMAP.

EXAMPLE 13

Preparation of 7-Triethylsilyl 13-[[(4S-trans)-4,5-dihydro-2,4-diphenyl-5-oxazolyl]-carbonyl]baccatin III (4S-trans)-4,5-Dihydro-2,4-diphenyl-5-oxazolecarboxylic acid (65.0 mg, 0.243 mmoles), 7-triethylsilyl baccatin III (0.142 g, 0.203 mmoles), DCC (75 mg, 256 mmoles), and pyrrolidinopyridine (38 mg, 256 mmoles) were added to a flame-dried 1 dram vial, purged with argon and partially dissolved in toluene (1.0 ml). The resulting yellowish heterogeneous mixture was stirred at room temperature. TLC at 3 hours showed the presence of the title product (1:1 EtOAc:hexanes, PMA/EtOH, U.V.) (TLC at 7 and 23 hours after stirring at room temperature showed no further change.)

The reaction mixture was diluted with ethyl acetate (1 ml), filtered through a pad of celite and concentrated to give 0.275 g of an oily yellowish solid. ¹H NMR showed the desired coupled title product and 7-triethylsilyl baccatin III in ~8:1 ratio. The N-acyl urea by-product of the coupling agent was also present in about the same amount as 7-triethylsilyl baccatin III.

The solid was chromatographed on silica gel with 1:2 EtOAc/hexane to give 0.176 g of an off-white solid. Yield ~91%. ¹H NMR showed only the desired coupled product and the N-acyl urea in ~11:1 ratio.

EXAMPLE 14

Preparation of 7-Triethylsilyl 13-[[(4S-trans)-4,5-dihydro-2,4-diphenyl-5-oxazolyl]-carbonyl]baccatin III (4S-trans)-4,5-Dihydro-2,4-diphenyl-5-oxazolecarboxylic acid (66.7 mg, 0.250 mmoles), 7-triethylsilyl baccatin III (0.146 g, 0.208 mmoles), DCC (79 mg, 0.383 mmoles), and 4-morpholino pyridine (41 mg, 0.250 mmoles) were added to a flame-dried 1 dram vial, purged with argon, and partially dissolved in toluene (1 ml). The resulting yellow heterogeneous mixture was stirred at room temperature. TLC at 3 hours showed the presence of the title product (1:1 EtOAc:hexane, PMA/EtOH, U.V.). (TLC at 7 and 23 hours after stirring at room temperature showed no further change.)

The reaction mixture was diluted with ethyl acetate (1 ml), filtered through a pad of Celite, and concentrated to give 0.280 g of a yellowish solid. $^1$H NMR showed the desired coupled title product and no 7-triethylsilyl baccatin III (although a trace was visible by TLC). The N-acyl urea by-product from the coupling agent was present in a ratio to title product of ~1:9.

The solid was chromatographed on silica gel with 1:2 EtOAc:hexanes to give 0.196 g of a white solid. $^1$H NMR showed only the coupled title product and the N-acyl urea in about a 15:1 ratio. Yield greater than 90%. M.P.=139°–142° C. $[\alpha]hd D=-49.5°$, $[\alpha]_{578}=-52.6°$, $[\alpha]_{546}=-63.5°$, $[\alpha]_{436}=-157.0°(c=1.0, CHCl_3)$.

EXAMPLE 15

Preparation of 7-Triethylsilyl 1 3-[[(4S-trans)-4,5-dihydro-2,4-diphenyl-5-oxazolyl ]-carbonyl] baccatin III and 7-Triethylsilyl 13-[[(4S-cis)-4,5-dihydro-2,4-diphenyl-5-oxazolyl]- carbonyl] baccatin III

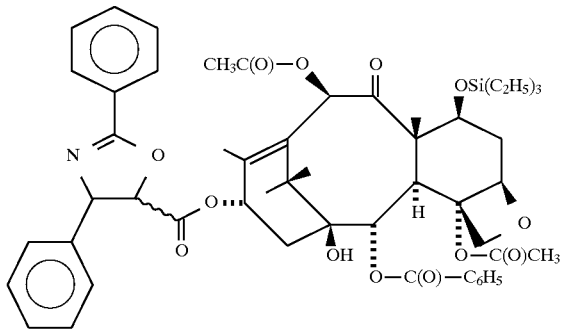

A mixture of the cis and trans oxazoline title products of Example 9 in a 3:1 ratio of cis: trans (100 mg), 7-triethylsilyl baccatin III (219 mg, 0.3121 mmol), DCC (97 mg) and DMAP (23 mg) in toluene (0.9 ml) was prepared. After one hour of heating at 80° C. there was a considerable amount of 7-triethylsilyl baccatin III unreacted. Another charge of DMAP (97 mg) and DCC (23 mg) was added, and the mixture heated at 80° C. overnight. Small amounts of starting material were observed by TLC (hexane:EtOAc 2:1).

The reaction mixture obtained was diluted with methylene chloride (20 ml), saturated sodium bicarbonate (10 ml, aq.) was added and the water layer was extracted with methylene chloride (2×10 ml), and the combined organic layers dried over anhydrous MgSO$_4$. Upon concentration in vacuo, the product was purified on HPLC (hexane:ethyl acetate 4:1) to give a mixture of the title products containing dicyclohexy-lurea (DCU). The product had a weight of 260 mg after resuspension in ethyl acetate and removal of some DCU by filtration. Another HPLC purification gave 117 mg of the pure trans title product (40%) and 45 mg of a mixture (~2:1 trans title product: cis title product (15%)). The mixture was purified by preparative TLC (hexanes: ethyl acetate, 1:1) to give 11 mg of the cis title product.

EXAMPLE 16

Preparation of Taxol

The coupled title product obtained in Example 10 above (0.102 g, 0.107 mmoles) was weighed into a 10 ml flask and dissolved in tetra-hydrofuran (1.2 ml). Methanol was then added (1.2 ml) and the homogeneous solution cooled to 0° C. HCl (aq., 1 N, 0.59 ml, 0.59 mmoles) was added dropwise and the clear homogeneous solution was stirred at 0° C. After 3 hours at 0° C., TLC (1:1 ethyl acetate:hexane, PMA/ethanol, U.V.) indicated starting material remained, and the clear homogenous solution was transferred to a 4° C. cold room. After 18 hours at 4° C., TLC analysis showed the reaction to be essentially complete (1:1 ethyl acetate:hexane, PMA/ethanol, U.V.). The following compound was obtained:

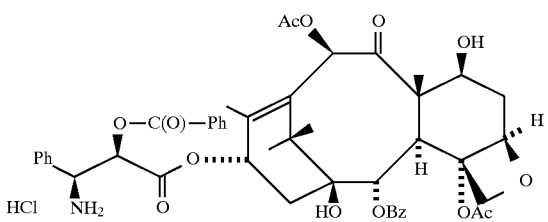

The clear homogeneous solution was warmed to room temperature. 3.5 ml saturated aqueous NaHCO$_3$ was added (bubbling was noted) to yield a heterogeneous mixture. Addition of 5 ml tetrahydrofuran and 2 ml water did not significantly enhance the solubility. The heterogeneous mixture was stirred vigorously at room temperature. After stirring at room temperature for 1 hour, a heterogeneous mixture was still present. The mixture was further diluted with 7 ml water and 4 ml tetrahydrofuran. The resulting clear homogeneous solution was stirred at room temperature. TLC at 2½ hours after NaHCO$_3$ addition showed only the presence of taxol (2:1 ethyl acetate/hexane, PMA/ethanol, U.V.). The reaction mixture was diluted with 25 ml ethyl acetate and 25 ml water and shaken. The layers were separated, and the aqueous fraction extracted with 3×25 ml ethyl acetate. The combined organic fractions were dried over Na$_2$SO$_4$, filtered and concentrated to give 104 mg of a slightly off-white glassy solid. $^1$H NMR showed taxol. The solid obtained was purified by chromatography on silica gel (column: 20 mm diameter ×70 mm length) with 2:1 ethyl acetate/hexane to 4:1 ethyl acetate/hexane to give 79.0 mg of the title product as a white solid. Yield=86.4%.

EXAMPLE 17

Preparation of 7.13-BisTES Baccatin

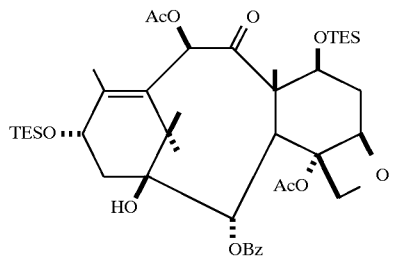

Baccatin III (3.102 g, 5.290 mmol) was dissolved in dry DMF (21 mL). To this solution at 0° C. was added imidazole (1.80 g, 26.5 mmol), followed by TESCl (4.45 mL. 26.5 mmol). The reaction was stirred at room temperature overnight and diluted with EtOAc (350 mL), and washed with water (4×20 mL) and brine. The organic layer was dried and concentrated in vacuo, the residue was chromatographed (20% ethyl acetate in hexanes) to afford 4.00 g (89.1%) of the desired product.

EXAMPLE 18

Preparation of 1-DMS-7,13-TES Baccatin

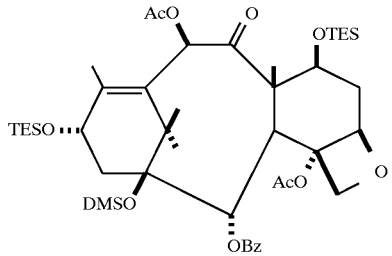

7,13-TES baccatin (2.877 g, 3.534 mmol) was dissolved in dry DMF (17.7 mL). To this solution at 0° C. was added imidazole (720.9 mg, 10.60 mmol), followed by dimethylchlorosilane 91.18 mL, 10.60 mmol). The reaction was stirred at that temperature for 45 minutes, and then diluted with EtOAc (300 mL) and washed with water (4×20 mL). The organic phase was dried and concentrated in vacuo. The residue was chromatographed (10% ethyl acetate in hexanes) to afford 2.632 g (85.4%) of the desired product.

EXAMPLE 19

Preparation of 4-Hydroxy-7,13-BisTES-1-DMS Baccatin

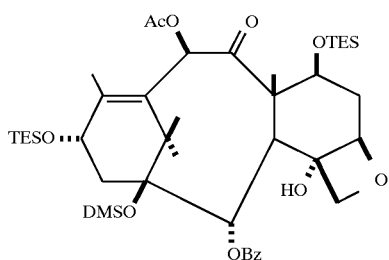

The silylated baccatin derivative of Example 18 (815 mg, 0.935 mmol) was dissolved in THF (15.6 mL). To this solution at 0° C. was added Red-Al (0.910 mL, 60% wt, 4.675 mmol). After 40 minutes, the reaction was quenched with saturated sodium tartrate solution (7 mL). After 5 minutes, the reaction mixture was diluted with EtOAc (250 mL).The organic phase was washed with water and brine and dried. The organic layer was then concentrated in vacuo, the residue was chromatographed (10–20% ethyl acetate in hexanes) to afford 590 mg (76.0%) of the desired C4-hydroxyl baccatin analog.

EXAMPLE 20

Preparation of C4-Cyclopropyl ester -7,13-BisTES-1-DMS baccatin

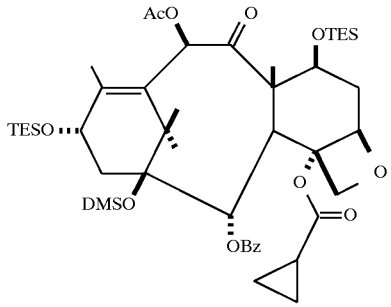

The C4-hydroxyl baccatin derivative of Example 19 (196 mg, 0.236 mmol) was dissolved in dry THF (4.7 mL). This solution at 0° C. was treated with LHMDS (0.283 mL, 1M, 0.283 mmol), after 30 minutes at that temperature, cyclopropanecarbonyl chloride (0.032 mL, 0.354 mmol) was added. The reaction was stirred at 0° C. for 1 hour and then quenched with saturated $NH_4Cl$ (3 mL). The reaction mixture was extracted with EtOAc (1 00 mL), and washed with water and brine. The organic layer was dried and concentrated in vacuo. The resulting residue was chromatographed (10% ethyl acetate in hexanes) to afford 137 mg (65%) of the desired product.

EXAMPLE 21

Preparation of C4-Cyclopropane ester baccatin

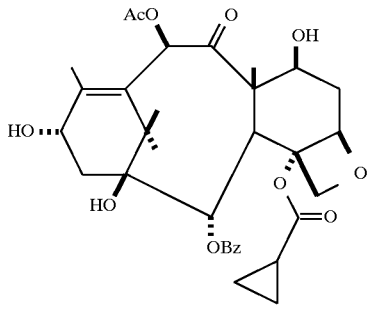

7,13-TES-1-DMS-4-cyclopropane baccatin of Example 20 (673 mg, 0.749 mmol) was dissolved in dry acetonitrile (6 mL) and THF (2 mL). To this solution at 0° C. was added pyridine (2.25 mL), followed by 48% HF solution (6.74 mL). After 30 minutes at 0° C., TBAF (2.25 mL, 1M, 2.25 mmol) was added. Additional dose of TBAF was added until starting material was consumed as judged by TLC. The reaction mixture was concentrated to a syrup, and then diluted with EtOAc (350 mL) and washed with 1N HCl, NaHCO3 saturated solution, brine and concentrated in vacuo. The residue was chromatographed (60% ethyl acetate in hexanes) to afford 366 mg (80%) of the desired product.

EXAMPLE 22

Preparation of 7-TES-4-Cyclopropane Baccatin

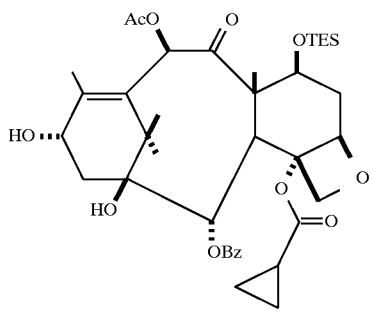

4-cyclopropane baccatin of Example 21 (46.6 mg, 0.076 mmol) was dissolved in dry DMF (1 mL). To this solution at 0° C. was added imidazole (20.7 mg, 0.305 mmol), followed by TESCl (0.0512 mL, 0.305 mmol). The reaction was stirred at 0° C. for 30 minutes and diluted with EtOAc (50 mL). The reaction mixture was washed with water and brine and dried then concentrated in vacuo. The residue was chromatographed (30–50% ethyl acetate in hexanes) to afford 36 mg (65.1%) of the desired product.

EXAMPLE 23

Preparation of 2',7-BisTES-4-Cyclopropane Paclitaxel

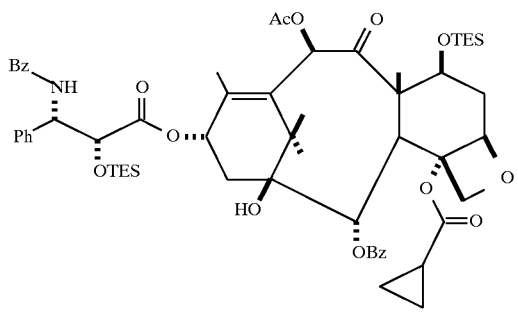

A THF (1 mL) solution of the compound of Example 22 (30.0 mg, 0.0413 mmol) was cooled to −40° C. and treated with LHMDS (0.062 mL, 0.062 mmol). After 5 minutes, a THF solution (0.5 mL) of β-lactam* (23.6 mg, 0.062 mmol) was added. The reaction was stirred at 0° C. for 1 hour, and then quenched with saturated NH$_4$Cl solution (1 mL). The reaction mixture was extracted with EtOAc (40 mL) and washed with water and brine. The organic phase was dried and concentrated in vacuo, the residue was chromatographed (20–30–60% ethyl acetate in hexanes) to afford 24.5 mg (53.6%) of the desired product together with 5.1 mg (17%) of the starting material.

*Methods for preparing this beta-lactam are found in U.S. Pat. No. 5,175,315

EXAMPLE 24

Preparation of 4-Cyclopropane ester of paclitaxel

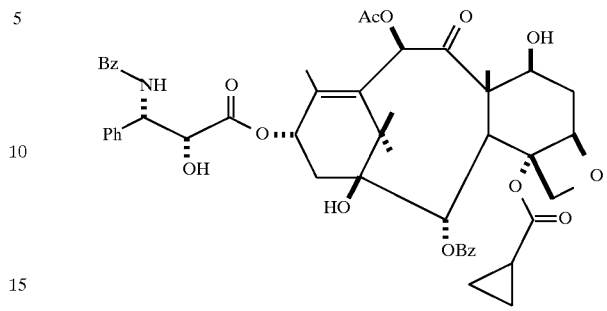

An acetonitrile solution (0.5 mL) of the product of Example 23 (22.0 mg, 0.020 mmol) was treated at 0° C. with pyridine (0.060 mL), followed by 48% HF solution (0.180 mL). The reaction mixture was kept at 5° C. overnight and then diluted with EtOAc (30 mL), and washed with water and brine. The organic layer was dried and concentrated in vacuo. The residue was chromatographed (60% ethyl acetate in hexanes) to afford 10.0 mg (57.2%) of the desired product.

$^1$H NMR (300 MHz, CDCl$_3$): δ 8.10–8.06 (m, 2H), 7.76–7.26 (m, 13H), 7.04 (d, J=9.1 Hz, 1H), 6.27 (s, 1H), 6.14 (m, 1H), 5.82 (d, J=9.1 Hz, 1), 5.65 (d, J=6.9 Hz, 1H), 4.85 (m, 2H), 4.39 (m, 1H), 4.19 (AB q, J=8.4 Hz, 2H), 3.80 (d, J=6.9 Hz, 1H), 3.59 (d, J=4.8 Hz, 1H), 2.60–1.13 (m, 24H, incl. singlets at 2.23, 1.77, 1.66, 1.23, 1.14, 3H each).

HRMS calcd. for C$_{49}$H$_{54}$NO$_{14}$ (MH$^+$): 880.3544, found: 880.3523.

EXAMPLE 25

Preparation of 7,13-TES-1-DMS-4-Cyclobutyl ester baccatin

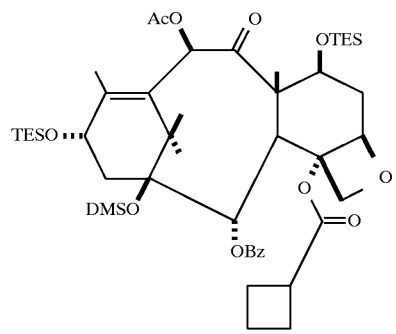

A THF solution (2.6 mL) of the product of Example 19 (113.6 mg, 0.137 mmol) was treated at 0° C. with LHMDS (0.178 mL, 1M, 0.178 mmol). After 30 minutes at 0° C., cyclobutylcarbonyl chloride (24.4 mg, 0.206 mmol) was added. The reaction was stirred at 0° C. for 1 hour and quenched with NH$_4$Cl saturated solution (2 mL). The reaction mixture was extracted with EtOAc (75 mL), washed with water and brine. The organic layer was dried and concentrated in vacuo. The residue was chromatographed (10% ethyl acetate in hexanes) to afford 80 mg (64.1%) of the desired product.

EXAMPLE 26

Preparation of 4-Cyclobutyl baccatin

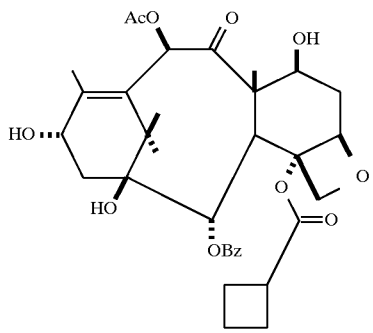

To an acetonitrile solution (3 mL) of the compound of Example 25 at 0° C. was added dry pyridine (0.61 mL), followed by 48% HF (1.83 mL). After 1 hour at 0° C., TBAF (0.61 mL, 1M, 0.61 mmol) was added. Additional TBAF was added until all of the starting material was consumed. The solvent was then partially removed, and the residue was diluted with EtOAc (150 mL), and washed with 1N HCl and $NaHCO_3$ saturated solution. The organic layer was then dried and concentrated in vacuo.

The residue was chromatographed (60% ethyl acetate in hexanes to afford 95.6 mg (75%) of the desired product.

EXAMPLE 27

Preparation of 7-TES-4-Cyclobutyl ester baccatin

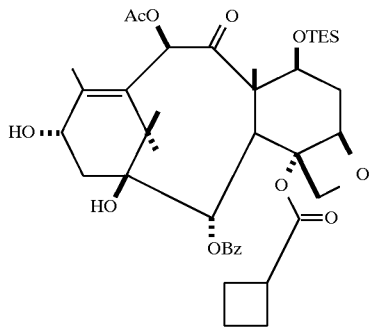

4-cyclobutyl baccatin of Example 26 (85 mg, 0.136 mmol) was dissolved in dry DMF (1.4 mL). To this solution at 0° C. was added imidazole (36.9 mg, 0.543 mmol) and TESCl (91.2 uL, 0.543 mmol). The reaction mixture was diluted with EtOAc (75 mL) and washed with water and brine. The organic layer was dried and concentrated in vacuo. The residue was chromatographed (40% ethyl acetate in hexanes to afford 74 mg (73.6%) of the desired product.

EXAMPLE 28

Preparation of 2',7-TES-4-Cyclobutyl Paclitaxel

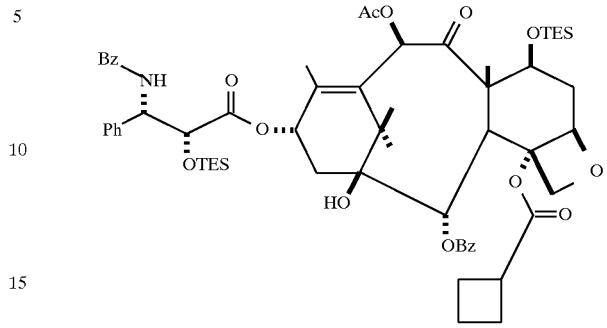

7-TES-4-cyclobutyl baccatin of Example 27 (41 mg, 0.055 mmol) was dissolved in THF (1 mL). This solution was cooled to −40° C. and treated with LHMDS (0.083 mL, 1M, 0.083 mmol), followed by a THF solution (0.5 mL) of β-lactam of Example 23 (31.7 mg, 0.083 mmol). The reaction was kept at 0° C. for 1 hour and quenched with $NH_4Cl$ (2 mL). The reaction mixture was extracted with EtOAc (50 mL), and washed with water and brine. The organic layer was then dried and concentrated in vacuo, the residue was chromatographed (20–30% ethyl acetate in hexanes) to afford 56 mg (90.2%) of the desired product.

EXAMPLE 29

Preparation of 4-Cyclobutyl Paclitaxel

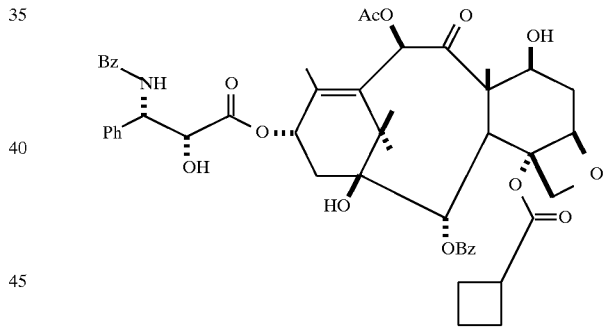

2',7-TES-4-cyclobutyl taxol of Example 28 (47 mg, 0.042 mmol) was dissolved in acetonitrile (1 mL), to this solution at 0° C. was added pyridine (0.125 mL), followed by 48% HF (0.375 mL). The reaction was kept at 5° C. overnight. The reaction was then diluted with EtOAc (50 mL), washed with 1N HCl, $NaHCO_3$ saturated solution and brine. The organic layer was dried and concentrated in vacuo. The residue was chromatographed (60% ethyl acetate in hexanes) to afford 31.8 mg (84.9%) of the desired product.

$^1$H NMR (300 MHz, $CDCl_3$): δ 8.15–8.12 (m, 2H), 7.73–7.26 (m, 13H), 6.96 (d, J=9.0 Hz, 1H), 6.26 (s, 1H), 6.17 (m, 1H), 5.80 (d, J=9.0 Hz, 1H), 5.66 (d, J=7.1 Hz, 1H), 4.83 (m, 2H), 4.41 (m, 1H), 4.26 (AB q, J=8.4 Hz, 2H), 3.78 (d, J=7.0 Hz, 1H), 3.57 (d, J=5.2 Hz, 1H), 3.42 (m, 1H), 2.61–1.14 (m, 25H, incl. singlets at 2.23, 1.76, 1.68, 1.23, 1.14, 3H each).

HRMS calcd. for $C_{50}H_{56}NO_{14}$ ($MH^+$). 894.3701, found: 894.3669.

EXAMPLE 30

Preparation of 7,13-TES- 1-DMS-4-Cyclopentyl ester of baccatin

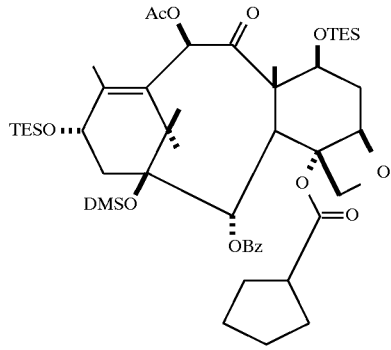

A THF solution (3.5 mL) of the compound of Example 19 (147 mg, 0.177 mmol) was treated at 0° C. with LHMDS (0.230 mL, 1M, 0.230 mmol). After 30 minutes, cyclopentylcarbonyl chloride (32.3 uL, 0.266 mmol) was added. The reaction was stirred for 1 hour at that temperature, and then quenched with $NH_4Cl$ saturated solution. The reaction mixture was extracted and washed and dried, and concentrated in vacuo. The residue was chromatographed (10% ethyl acetate in hexanes) to afford 90 mg (55%) of the desired product.

EXAMPLE 31

Preparation of 4-Cyclopentyl baccatin

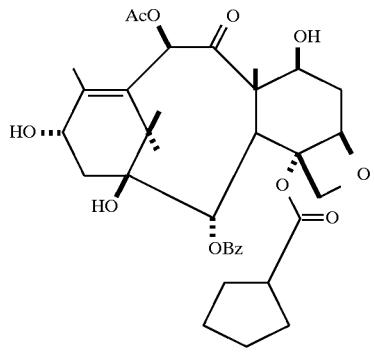

An acetonitrile solution (1.6 mL) of the product of Example 30 (75 mg, 0.081 mmol) was treated at 0° C. with pyridine (0.24 mL), followed by 48% HF (0.72 mL). The reaction was stirred at 0° C. for 1 hour, and then TBAF (0.405 mL, 1M, 0.405 mmol) was added. Another five eqivalent of reagent was added after 1 hr. The reaction mixture was diluted with EtOAc (100 mL), and washed with 1N HCl and $NaHCO_3$ saturated solution and brine. The organic layer was dried and concentrated in vacuo. The residue was chromatographed (50% ethyl acetate in hexanes) to afford 44 mg (85%) of the desired product.

EXAMPLE 32

Preparation of 7-TES-4-Cyclopentyl ester baccatin

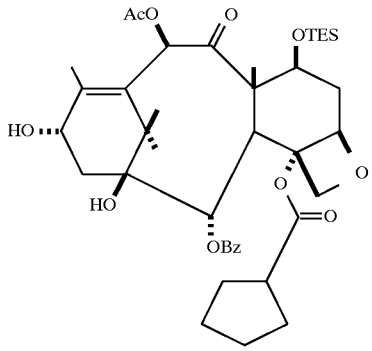

4-cyclopentyl baccatin (35 mg, 0.055 mmol) was dissolved in dry DMF (1 mL). To this solution at 0° C. was added imidazole (14.9 mg, 0.219 mmol), followed by TESCl (36.8 uL, 0.219 mmol). The reaction mixture was stirred at 0° C. for 30 minutes, and diluted with EtOAc (50 mL). The organic layer was washed and dried and concentrated in vacuo. The residue was chromatographed (40% ethyl acetate in hexanes) to afford 31 mg (75%) of the desired product.

EXAMPLE 33

Preparation of 2',7-TES-4-Cyclopentyl ester baccatin

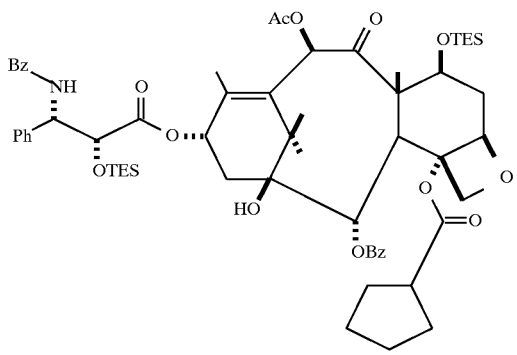

A THF solution (0.6 mL) of the product of Example 32 (24.5 mg, 0.0324 mmol) was treated at −40° C. with LHMDS (0.049 mL, 1M, 0.049 mmol), followed by a THF solution (0.3 mL) of β-lactam of Example 23 (18.6 mg, 0.049 mmol). The reaction was stirred at 0° C. for 1 hour, and then quenched with $NH_4Cl$ saturated solution. The reaction mixture was extracted with EtOAc (35 mL), and washed, dried and concentrated in vacuo The residue was chromatographed (20–30–50% ethyl acetate in hexanes) to afford 15.5 mg (42%) of the desired product together with 7.8 mg (31.8%) of the unreacted starting material.

EXAMPLE 34

Preparation of 4-Cyclopentyl ester paclitaxel

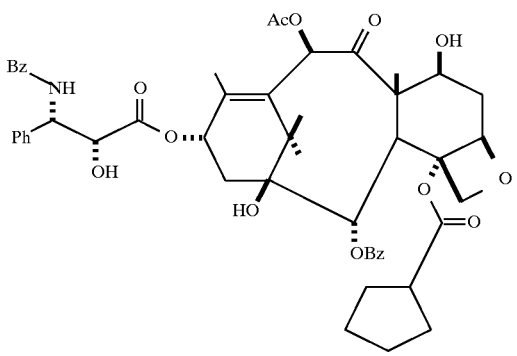

A acetonitrile solution (0.3 mL) of the product of Example 33 (13 mg, 0.0115 mmol) was treated at 0° C. with pyridine (0.035 mL), followed by 48% HF (0.103 mL). The reaction was kept at 5° C. overnight. The reaction mixture was then diluted with EtOAc (30 mL), and washed with 1N HCl, NaHCO$_3$ and brine. The organic layer was dried and concentrated in vacuo. The residue was chromatographed (50% ethyl acetate in hexanes) to afford 7.3 mg (70.3%) of the desired product. $^1$H NMR (300 MHz, CDCl$_3$): δ 8.17–8.14 (m, 2H), 7.74–7.26 (m, 13H), 6.90 (d, J=8.9 Hz, 1H), 6.27 (s, 1H), 6.20 (m, 1H), 5.75 (d, J=8.9 Hz, 1H), 5.69 (d, J=7.0 Hz, 1 H), 4.79 (m, 2H), 4.44 (m, 1H), 4.24 (AB q, J=8.4 Hz, 2H), 3.81 (d, J=7.0 Hz, 1H), 3.46 (d, J=4.7 Hz, 1H), 3.06 (m, 1H), 2.56–1.15 (m, 27H, incl. singlets at 2.24, 1.82, 1.68, 1.33, 1.15, 3H each). HRMS calcd. for C$_{51}$H$_{57}$NO$_{14}$Na (MNa$^+$): 930.3677, found: 930.3714.

EXAMPLE 35

Preparation of 2',7-silylated-4-Cyclopropane taxane with furyl side chain

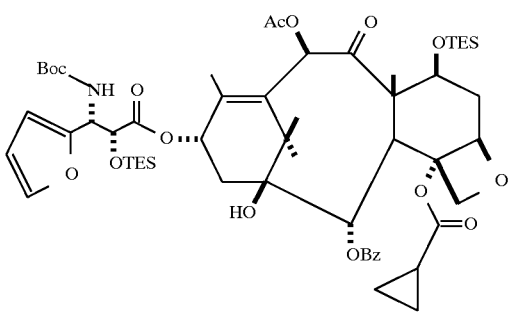

A THF solution (2 mL) of the product of Example 22 (75.8 mg, 0.104 mmol) was treated at −40° C. with LHMDS (0.136 mL, 1M, 0.136 mmol) and β-lactam* (57.3 mg, 0.156 mmol). The reaction was stirred at 0° C. for 1 hour, and then quenched with NH$_4$Cl saturated solution (1 mL). The reaction mixture was extracted with EtOAc, washed and dried and concentrated in vacuo. The residue was chromatographed (20% ethyl acetate in hexanes) to afford 113 mg (100%) of the desired product.

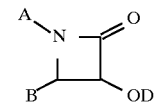

A = Benzoyloxycarbonyl
B = 2-Furyl
D = Silyl Protecting Group

Methods for preparing the beta-lactam above are disclosed in U.S. Pat. No. 5,227,400.

EXAMPLE 36

Preparation of 4-Cyclopropyl ester taxane with furyl side chain

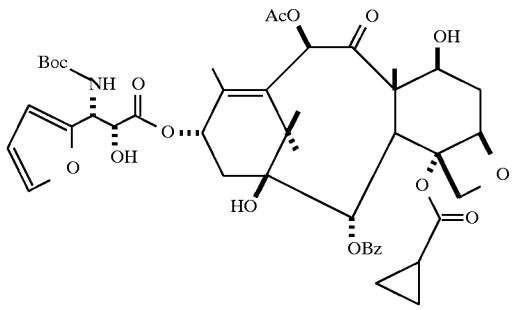

A acetonitrile solution of the product of Example 35 (2 mL) was treated at 0° C. with pyridine (0.27 mL), followed by 48% HF (0.81 mL). The reaction was kept at 5° C. for 3 hours, diluted with EtOAc (75 mL), washed with 1N HCl, NaHCO$_3$ saturated solution, brine and dried and concentrated in vacuo. The residue was chromatographed (50–60% ethyl acetate in hexanes) to afford 68 mg (88.2%) of the desired product.

$^1$H NMR (300 MHz, CDCl$_3$): δ 8.09–8.06 (m, 2H), 7.62–7.37 (m, 3H), 7.26 (s, 1H), 6.37–6.30 (m, 3H), 6.19 (m, 1H), 5.65 (d, J=7.0 Hz, 1H), 5.37 (d, J=9.9 Hz,1H), 5.23 (d, J=9.9 Hz, 1H), 4.82 (d, J=8.3 Hz, 1H), 4.76 (d, J=4.1 Hz, 1H), 4.42 (m, 1H), 4.18 (AB q, J=8.4 Hz, 2H), 3.85 (d, J=6.9 Hz, 1H), 3.37 (d, J=5.4 Hz, 1H), 2.55–1.01 (m, 33H, incl. singlets at 2.23, 1.90, 1.66, 1.26, 1.14, 3H each, 1.33, 9H).

HRMS calcd. for C$_{45}$H$_{56}$NO$_{16}$(MH$^+$) 866.3599, found 866.3569.

EXAMPLE 37

Preparation of 2',7-silylated-4-Cyclobutyl ester taxane with furyl side chain

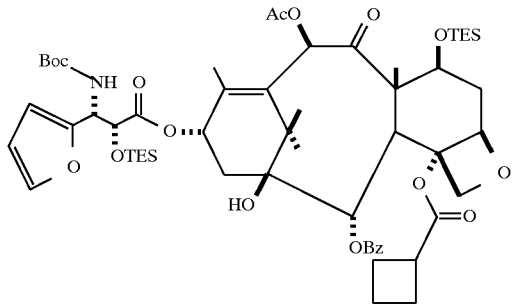

A THF solution (0.8 mL) of the product of Example 22 was treated at −40° C. with LHMDS (0.050 mL, 1M, 0.050 mmol). After 2 minutes, β-lactam of Example 35 (18.2 mg, 0.050 mmol) was added. The reaction mixture was stirred at 0° C. for 1 hour, and quenched with NH$_4$Cl saturated solution. The reaction mixture was extracted and washed, dried and concentrated in vacuo. The residue was chromatographed (20% ethyl acetate in hexanes) to afford 33.0 mg (89.4%) of the desired product.

EXAMPLE 38

Preparation of 4-Cyclobutyl ester taxane with furyl side chain

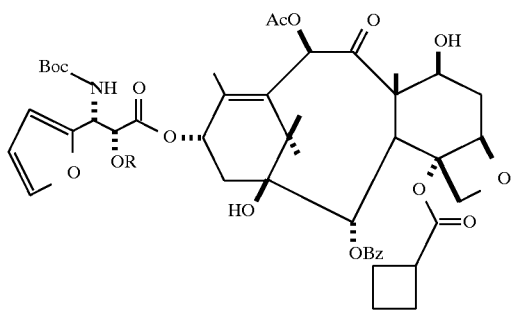

An acetonitrile solution (1 mL) of the product of Example 37 (30.0 mg, 0.027 mmol) was treated at 0° C. with pyridine (0.081 mL), followed by 48% HF (0.243 mL). The reaction was kept at 5° C. overnight, and diluted with EtOAc (50 mL), washed with 1N HCl, NaHCO$_3$ saturated solution, and brine. The organic layer was then dried and concentrated in vacuo.

The residue was chromatographed (60% ethyl acetate in hexanes) to afford 22 mg (92.4%) of the desired product.

$^1$H NMR (300 HMz, CDCl$_3$): δ 8.13–8.10 (m, 2H), 7.62–7.45 (m, 3H), 6.42–6.38 (m, 2H), 6.30 (s, 1H), 6.19 (m, 1H), 5.65 (d, J=7.1 Hz, 1H), 5.34 (d, J=9.6 Hz, 1H), 5.18 (d, J=9.8 Hz, 1H), 4.90 (d, J=7.7 Hz, 1H), 4.73 (dd, J=2.0 Hz, J'=5.7 Hz, 1H), 4.45 (m, 1H), 4.25 (AB q, J=8.4 Hz, 2H), 3.80 (d, J=7.0 Hz, 1H), 3.50 (m, 1H), 3.27 (d, J=5.8 Hz, 1H), 2.61–1.15 (m, 34H, incl. singlets at 2.24, 1.86, 1.68, 1.26, 1.15, 3H each, 1.33, 9H).

EXAMPLE 39

Preparation of 7,13-TES-1-DMS-4-Butyrate baccatin

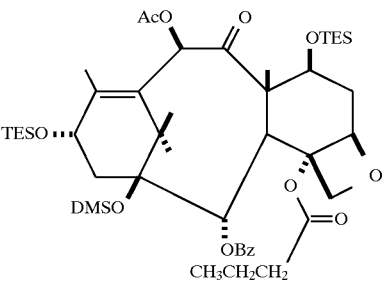

The C4-hydroxyl baccatin derivative of Example 19 (181 mg, 0.218 mmol) was dissolved in dry THF (4.4 mL). This solution at 0° C. was treated with LHMDS (0.262 mL, 1M, 0.262 mmol), after 30 minutes at that temperature, butyryl chloride (0.034 mL, 0.33 mmol) was added. The reaction was stirred at 0° C. for 1 hour and then quenched with saturated NH$_4$Cl (3 mL). The reaction mixture was extracted with EtOAc (100 mL), and washed with water and brine. The organic layer was dried and concentrated in vacuo. The resulting residue was chromatographed (10% ethyl acetate in hexanes) to afford 138 mg (70.3%) of the desired product.

EXAMPLE 40

Preparation of C4-Butyryl ester baccatin

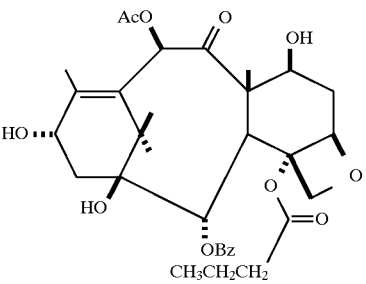

7,13-TES-1-DMS-4-butyrate baccatin of Example 39 (527 mg, 0.586 mmol) was dissolved in dry acetonitrile (19.5 mL). To this solution at 0° C. was added pyridine (1.95 mL), followed by 48% HF solution (5.86 mL). After 30 minutes at 0° C., the reaction mixture was kept at 5° C. overnight. Then diluted with EtOAc (400 mL) and washed with 1N Hcl, NaHCO3 saturated solution, brine and concentrated in vacuo. The residue was chromatographed (60% ethyl acetate in hexanes) to afford 286 mg (80%) of the desired product.

EXAMPLE 41

Preparation of 7-TES-4-Butyrate baccatin

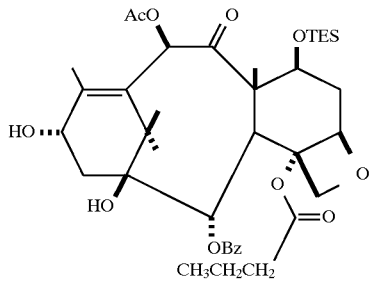

4-butyrate baccatin of Example 40 (286 mg, 0.466 mmol) was dissolved in dry DMF (2.3 mL). To this solution at 0° C. was added imidazole (127 mg, 1.86 mmol), followed by TESCl (0313 mL, 1.86 mmol). The reaction was stirred at 0° C. for 30 minutes and then diluted with EtOAc (100 mL). The reaction mixture was washed with water and brine and dried then concentrated in vacuo. The residue was chromatographed (30–50% ethyl acetate in hexanes) to afford 283.3 mg (83.5%) of the desired product.

EXAMPLE 42

Preparation of 2',7-BisTES-C4-Butyrate Paclitaxel

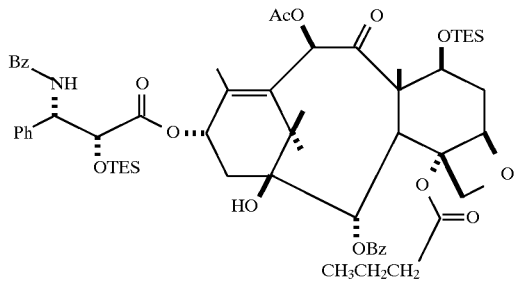

A THF (8.3 mL) solution of the product of Example 41 (300.6 mg, 0.413 mmol) was cooled to −40° C. and treated with LHMDS (0.619 mL, 0.619 mmol). After 5 minutes, a THF (4.1 mL) of β-lactam of Example 23 (236 mg, 0.619 mmol) was added. The reaction was stirred at 0° C. for 1 hour, and then quenched with saturated $NH_4Cl$ solution (3 mL). The reaction mixture was extracted with EtOAc (150 mL) and washed with water and brine. The organic phase was dried and concentrated in vacuo, the residue was chromatographed (20–30–60% ethyl acetate in hexanes) to afford 377 mg (82.3%) of the desired product.

EXAMPLE 43

Preparation of C-4-Butyrate Paclitaxel

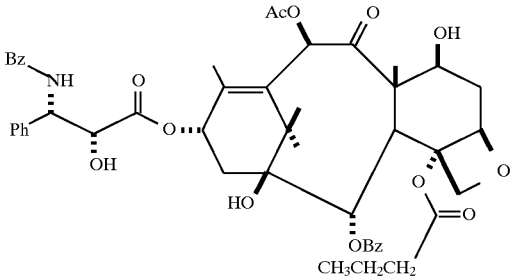

An acetonitrile solution (15.3 mL) of the product of Example 42 (366 mg, 0.334 mmol) was treated at 0° C. with pyridine (0.926 mL), followed by 48% HF solution (2.78 mL). The reaction mixture was kept at 5° C. overnight and then diluted with EtOAc (200 mL), and washed with water and brine. The organic layer was dried and concentrated in vacuo. The residue was chromatographed (60% ethyl acetate in hexanes) to afford 274 mg (94.5%) of the desired product.

$^1$H NMR (300 MHz, $CDCl_3$): δ 8.12–8.09 (m, 2H), 7.71–7.32 (m, 13H), 7.00 (d, J=8.9 Hz, 1H), 6.25 (s, 1H), 6.16 (m, 1H), 5.73 (d, J=8.8 Hz, 1H), 5.64 (d, J=7.0 Hz, 1H), 4.85 (d, KJ=9.4 Hz, 1H), 4.76 (m, 1H), 4.38 (m, 1 H), 4.20 (AB q, J=8.4 Hz, 2H), 3.77 (d, J=6.9 Hz, 1 H), 3.70 (d, J=4.3 Hz, 1H), 2.66–0.85 (m, 26H, incl. singlets at 2.20, 1.76, 1.65, 1.21, 1.11, 3H each, triplet at 0.88, 3H).

EXAMPLE 44

Preparation of 7,13-TES-1-DMS-4-ethyl carbonate baccatin

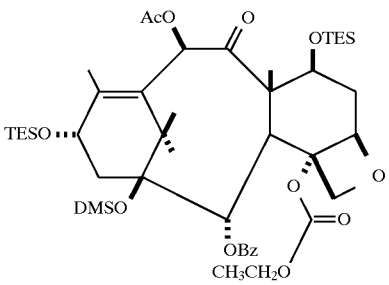

A THF solution (5 mL) of the product of Example 19 (205 mg, 0.247 mmol) was treated at 0° C. with LHMDS (0.296 mL, 1M, 0.296 mmol). After 30 minutes at 0° C., ethyl chloroformate (0.0354 ml, 0.370 mmol) was added. The reaction was stirred at 0° C. for 1 hour and quenched with $NH_4Cl$ saturated solution (3 mL). The reaction mixture was extracted with EtOAc (100 mL), washed with water and brine. The organic layer was dried and concentrated in vacuo. The residue was chromatographed (10% ethyl acetate in hexanes) to afford 155 mg (69.6%) of the desired product.

EXAMPLE 45

Preparation of C-4 ethyl carbonate baccatin

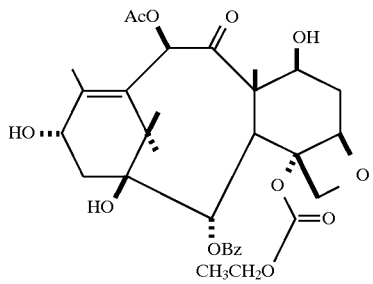

To a acetonitrile solution (5.6 mL) of the product of Example 44 (152 mg, 0.169 mmol) at 0° C. was added dry pyridine (0.56 mL), followed by 48% HF (1.69 mL). After 30 minutes at 0° C., the reaction mixture was kept at 5° C. overnight. Then the residue was diluted with EtOAc (150 mL), and washed with 1N HCl and NaHCO₃ saturated solution. The organic layer was then dried and concentrated in vacuo. The residue was chromatographed (60% ethyl acetate in hexanes to afford 99 mg (95.4%) of the desired product.

EXAMPLE 46

Preparation of 7-TES-C-4 ethyl carbonate baccatin

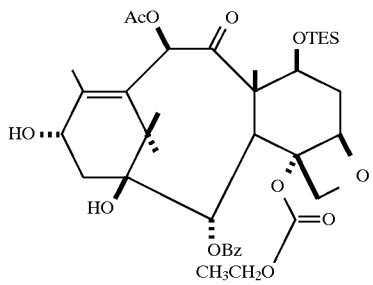

4-ethyl carbonate baccatin of Example 45 (95 mg, 0.154 mmol) was dissolved in dry DMF (0.771 mL). To this solution at 0° C. was added imidazole (42 mg, 0.617 mmol) and TESCl (104 uL, 0.617 mmol). The reaction mixture was diluted with EtOAc (100 mL) and washed with water and brine. The organic layer was dried and concentrated in vacuo. The residue was chromatographed (40% ethyl acetate in hexanes to afford 95 mg (84.4%) of the desired product.

EXAMPLE 47

Preparation of 2',7-TES-C-4 ethyl carbonate paclitaxel

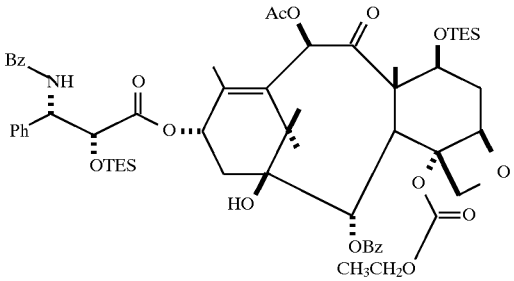

7-TES-4-ethyl carbonate baccatin of Example 46 (93.4 mg, 0.128 mmol) was dissolved in THF (2.6 mL). This solution was cooled to −40° C. and treated with LHMDS (0.192 mL, 1M, 0.192 mmol), followed by a THF solution (1.3 mL) of 0-lactam of Example 23 (73.1 mg, 0192 mmol). The reaction was kept at 0° C. for 1 hour and quenched with NH₄Cl (3 mL). The reaction mixture was extracted with EtOAc (100 mL), and washed with water and brine. The organic layer was then dried and concentrated in vacuo, the residue was chromatographed (20–30% ethyl acetate in hexanes) to afford 118 mg (83.0%) of the desired product.

EXAMPLE 48

Preparation of C-4 ethyl carbonate paclitaxel

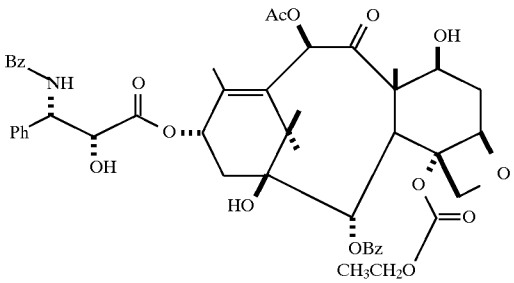

2',7-TES-4-ethyl carbonate taxol of Example 47 (114 mg, 0.103 mmol) was dissolved in acetonitrile (5.1 mL), to this solution at 0° C. was added pyridine (0.285 mL), followed by 48% HF (0.855 mL). The reaction was kept at 5° C. overnight. The reaction was then diluted with EtOAc (100 mL), washed with 1N HCl, NaHCO₃ saturated solution and brine. The organic layer was dried and concentrated in vacuo. The residue was chromatographed (60% ethyl acetate in hexanes) to afford 75 mg (82.8%) of the desired product.

$^1$H NMR (300 MHz, CDCl₃): δ 8.09–8.06 (m, 2H), 7.75–7.24 (m, 13H), 7.14 (d, J=9.0 Hz, 1H), 6.24 (s, 1H), 6.10 (m, 1H), 5.79 (d, J=7.1 Hz, 1H), 5.66 (d, J=6.9 Hz, 1H), 4.95 (d, J=8.2 Hz, 1H), 4.75 (m, 1H), 4.41–4.16 (m, 5H), 3.89 (d, J=4.3 Hz, 1H), 3.81 (d, J=6.9 Hz, 1H), 2.56–1.11 (m, 23H, incl. singlets at 2.21, 1.75, 1.65, 1.18, 1.11, 3H each, triplet at 1.22, 3H).

EXAMPLE 49

Preparation of 2',7-silylated-C-4-butyrate taxane with furyl side chain

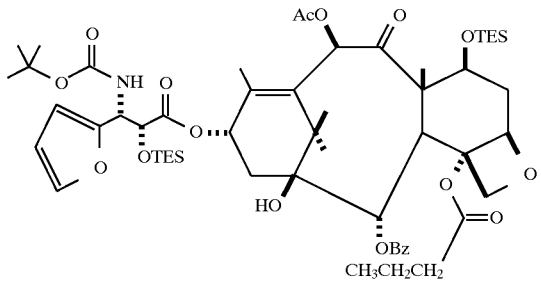

A THF solution (7.3 mL) of 7-silyl 4-butyrate baccatin of Example 41 (266 mg, 0.365 mmol) was treated at −40° C. with LHMDS (0.548 mL, 1M, 0.548 mmol). After 2 minutes, a THF solution (3.6 ml) of β-lactam of Example 35 (201 mg, 0.548 mmol) was added. The reaction mixture was stirred at 0° C. for 1 hour, and quenched with NH$_4$Cl saturated solution. The reaction mixture was extracted and washed, dried and concentrated in vacuo. The residue was chromatographed (20% ethyl acetate in hexanes) to afford 399.0 mg (99%) of the desired product.

EXAMPLE 50

Preparation of C-4 Butyrate taxane with furyl side chain

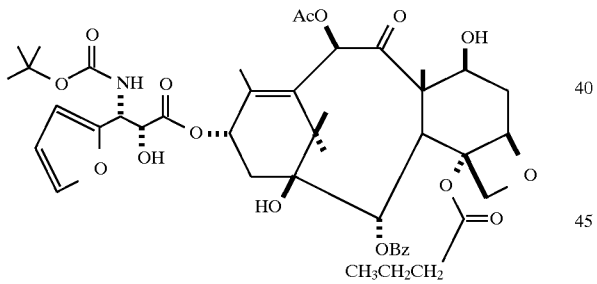

An acetonitrile solution (18.2 mL) of the product of Example 49 (399.0 mg, 0.364 mmol) was treated at 0° C. with pyridine (1.01 mL), followed by 48% HF (3.03 mL). The reaction was kept at 5° C. overnight, and diluted with EtOAc (200 mL), washed with 1N HCl, NaHCO$_3$ saturated solution, and brine. The organic layer was then dried and concentrated in vacuo. The residue was chromatographed (60% ethyl acetate in hexanes) to afford 305 mg (96.5%) of the desired product.

$^1$H NMR (300 MHz, CDCl$_3$): δ 8.05–8.02 (m, 2H), 7.56–7.35 (m, 4H), 6.33–6.26 (m, 3H), 6.15 (m, 1H), 5.59 (d, J=7.0 Hz, 1H), 5.40 (d, J=9.7 Hz, 1H), 5.26 (d, J=9.7 Hz, 1H), 4.85 (d, J=9.5 Hz, 1H), 4.66 (m, 1H), 4.39 (m, 1H 4.17 (AB q, J=8.4 Hz, 2H), 3.76 (d, J=6.9 Hz, 1H), 3.64 (J=6.0 Hz, 1H), 2.65–0.91 (m, 35H, incl. singlets at 2.18, 1.82, 1.62, 1.21, 1.09, 3H each, 1.28, 9H, triplet at 0.94, 3H).

EXAMPLE 51

Preparation of 7,13-BisTES-1-DMS-C-4 methyl carbonate baccatin

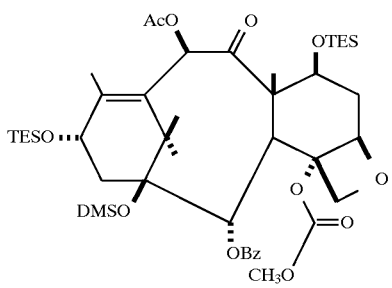

The compound of Example 19 (118 mg, 0.150 mmol) was dissolved in THF (3 mL). To this solution at 0° C. was added LHMDS (0.180 mL, 1M, 0.180 mmol). After 30 minutes, methyl chloroformate (0.174 mL, 0.225 mmol) was added. After another 30 minutes, the reaction was quenched with NH$_4$Cl. The reaction mixture was extracted with EtOAc (100 mL). The organic layer was washed with water (10 mL×2) and brine (10 mL). The organic phase was then dried and concentrated in vacuo. The residue was chromatographed (5–10% EtOAc/Hexanes) to afford 104 mg (82.1 %) of the desired product.

EXAMPLE 52

Preparation of C-4Methyl carbonate baccatin

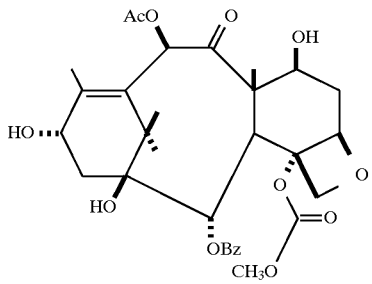

The compound of Example 51 (89.0 mg, 0.105 mmol) was dissolved in CH3CN (3.5 mL). To this solution at 0° C. was added pyridine (0.30 mL), followed by 48% HF (1.05 mL). The reaction was stirred at 0° C. for 6 hours, then diluted with EtOAc (100 mL). The reaction mixture was washed with 1N HCl (10 mL), NaHCO3 saturated solution (10 mL×3). The organic phase was dried and concentrated in vacuo. The residue was chromatographed (50% EtOAc/ Hexanes) to afford 70 mg (100%) of the desired product.

EXAMPLE 53

Preparation of 7-TES-C-4 methyl carbonate baccatin

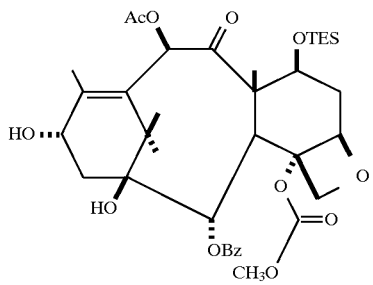

The compound of Example 52 (115.5 mg, 0.192 mmol) was dissolved in DMF (0.960 mL). To this solution at 0° C. was added imidazole (52.2 mg, 0.767 mmol), followed by TESCl (0.128 mL, 0.767 mmol). After 30 minutes, the reaction mixture was diluted with EtOAc (100 mL). The organic layer was washed with water (10 mL×2) and brine (10 mL). The organic phase was then dried and concentrated in vacuo. The residue was chromatographed (40% EtOAc/Hexanes) to afford 133 mg (96.8%) of the desired product.

EXAMPLE 54

Preparation of 2',7-silylated-C-4-methyl carbonate taxane with furyl side chain

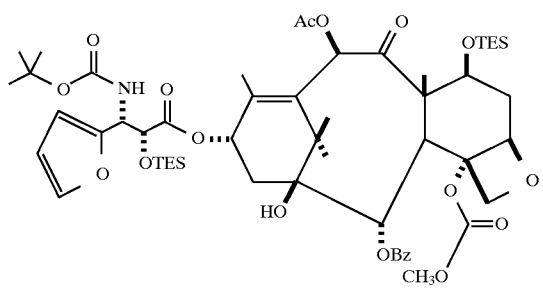

A THF solution (6.4 mL) of 7-silyl 4-methyl carbonate baccatin of Example 53 (227.8 mg, 0.318 mmol) was treated at −40° C. with LHMDS (0.350 mL, 1M, 0.350 mmol). After 2 minutes, a THF solution (3.6 ml) of β-lactam of Example 35 (140 mg, 0.382 mmol) was added. The reaction mixture was stirred at 0° C. for 1hour, and quenched with $NH_4Cl$ saturated solution. The reaction mixture was extracted and washed, dried and concentrated in vacuo. The residue was chromatographed (20% ethyl acetate in hexanes) to afford 332.0 mg (96.3%) of the desired product.

EXAMPLE 55

Preparation of C-4-Methyl carbonate taxane with fury side chain

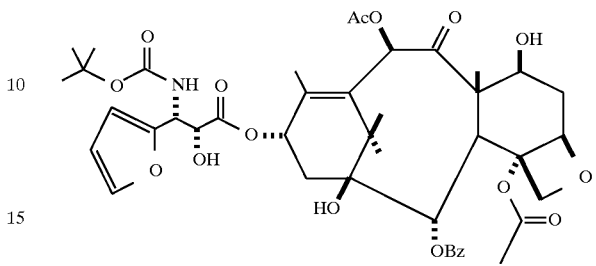

An acetonitrile solution (15.3 mL) of Example 54 (332.0 mg, 0.307 mmol) was treated at 0° C. with pyridine (1.7 mL), followed by 48% HF (5.1 mL). The reaction was kept at 5° C. overnight, and diluted with EtOAc (200 mL), washed with 1N HCl, $NaHCO_3$ saturated solution, and brine. The organic layer was then dried and concentrated in vacuo. The residue was chromatographed (60% ethyl acetate in hexanes) to afford 260 mg (99.0%) of the desired product.

$^1$H NMR (300 MHz, $CDCl_3$): δ 8.05–8.02 (m, 2H), 7.53–7.37 (m, 4H), 6.29–6.15 (m, 4H), 5.62 (d, J=6.9 Hz, 1H), 5.40 (d, J=9.6 Hz, 1H), 5.30 (d, J=9.6 Hz, 1H), 4.91 (d, J=9.3 Hz, 1H), 4.68 (m, 1H), 4.34 (m, 1H), 4.16 (AB q, J=8.5 Hz, 2H), 3.88 (s, 3H), 3.80 (d, J=8.9 Hz, 1H), 3.69 (d, J=5.5 Hz, 1H), 2.63–1.08 (m, 28H, incl. singlets at 2.18, 1.85, 1.60, 1.20, 1.08, 3H each, 1.26, 9H).

EXAMPLE 56

Preparation of 2',7-silylated-C-4 methyl carbonate paclitaxel

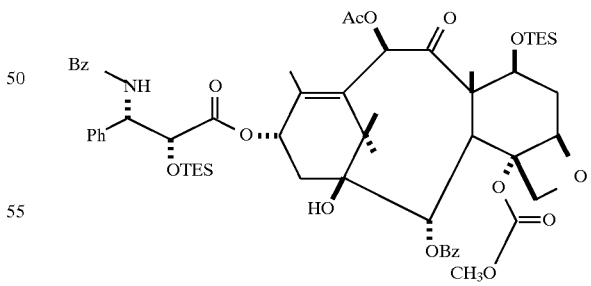

Compound of Example 53 (113.3 mg, 0.158 mmol) was dissolved in THF (3.16 mL). To this solution at −40° C. was added LHMDS (0.237 mL, 1M, 0.237 mmol), followed by β-lactam of Example 23 (90.43 mg, 0.237 mmol). Follow the same procedure as above, 159 mg (91.6%) of the desired product was obtained.

EXAMPLE 57

Preparation of C-4Methyl carbonate paclitaxel

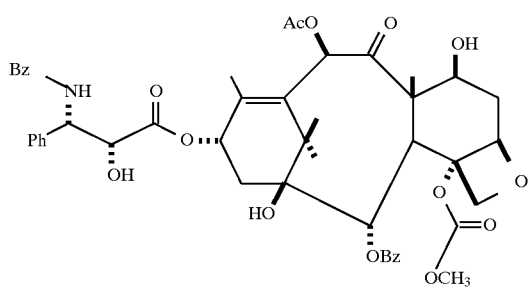

The compound of Example 56 (149 mg, 0.136 mmol) was dissolved in CH3CN (6.8 mL). To this solution at 0° C. was added pyridine (0.377 mL), followed by 48% HF (1.132 mL). Follow the same procedure as above, 103.4 mg (87.6%) of the desired product was obtained.

EXAMPLE 58

Preparation of C-4 Cyclopropyl ester–7-TES- 13-oxayol-baccatin

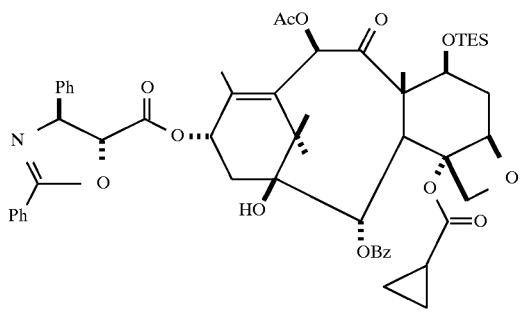

To a suspension of the product of Example 22 (72 mg, 0.099 mmol) and the product of Example 6 (29.4 mg, 0.110 mmol) in toluene (2 mL) at room temperature was added DMAP (13,4 mg, 0.110). After 10 minutes, DCC(22.6 mg, 0.110) was added. The reaction mixture was stirred at room temperature for 2 hours. The reaction mixture was then filtered through Celite, rinsed with EtOAc. The organic layer was concentrated in vacuo. The residue was chromatographed (30% EtOAc/Hexanes) to afford desired product (99 mg) in 100% yield.

$^1$H NMR (CDCl$_3$): δ 8.27–8.24 (m, 2H), 8.03–7.26 (m, 13H), 6.42 (s, 1H), 6.08 (m, 1H), 5.67 (d, J=7.0 Hz, 1H), 5.60 (d, J=6.0 Hz, 1H), 4.92 (d, J=6.1 Hz, 1H), 4.87 (d, J=8.3Hz, 1H), 4.50 (dd, J=6.6 Hz, J' =10.3 Hz, 1H), 4.16 (AB q, J=8.3 Hz, 2H), 3.85 (d, J=6.9 Hz, 1H), 2.56–0.52 (m, 39H, incl. singlets at 2.15, 2.02, 1.68, 1.20, 1.18, 3H each, triplet at 0.92, 9H).

HRMS calcd. for $C_{55}H_{66}NO_{13}Si$ (MH$^+$): 976.4303, found: 976.4271.

EXAMPLE 59

Preparation of C-4 Cyclopropyl ester of paclitaxel

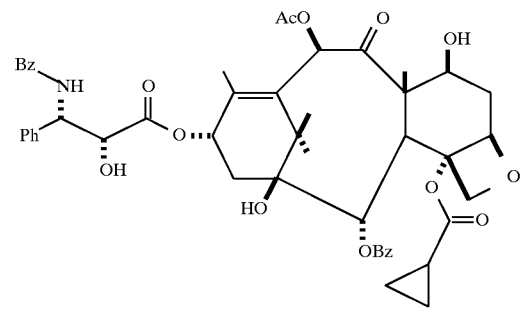

To a solution of the product of Example 58 (83.4 mg, 0.084 mmol) in THF (0.8 mL) and methanol (0.8 mL) at 0° C. was added 1N HCl (0.42 mL). The reaction was kept at 4° C. for 14 hours. The reaction mixture was warmed to room temperature and NaHCO$_3$ saturated solution (2.1 mL) was added. The reaction was stirred at room temperature for 3 hours and then poured into H$_2$O, the reaction mixture was extracted with EtOAc (4×20 mL). The combined organic layer was dried and concentrated in vacuo. The residue was chromatographed (60% EtOAc/hexanes) to afford desired product (45 mg) in 60% yield.

EXAMPLE 60

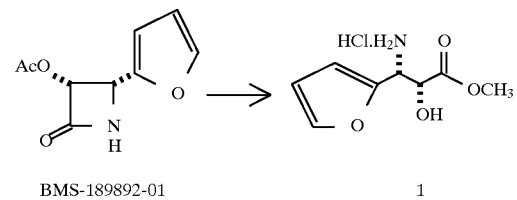

BMS-189892-01                                          1

In an oven-dried, argon purged 25 ml flask, BMS-189892-01 (485 mg, 3.0 mmol) (Note 1) was dissolved in dry methanol (5.0 ml). To this flask was added trimethylsilyl chloride (326 mg, 3.0 mmol) dropwise via a syringe at 0° C. The reaction mixture was stirred at 0° C. for 5 minutes and then the ice-water bath was removed. The reaction mixture was further stirred for 14 hours at room temperature. The reaction mixture was concentrated in vacuo and dried under high vacuum to yield 1 quantitatively (691 mg, 100%) as a white foam.

1. Chem Abs.: 34408-064-33.

EXAMPLE 61

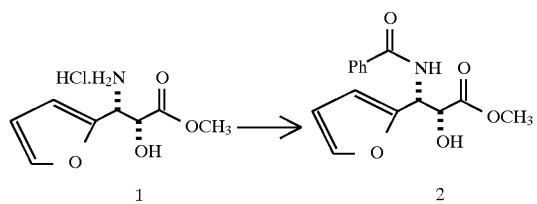

1                                                      2

In a 25 ml flask 1(691 mg, 3.0 mmol) from above was dissolved in sat. NaHCO₃ (10 ml). To this solution was added benzoyl chloroformate (512 mg, 3.0 mmol) at room temperature. The reaction mixture was stirred for 14 hours at room temperature during which time a white precipitate formed. The white precipitate was filtered off and washed with water (2×5 ml) and hexane 2×5 ml). The solid was dried under high vacuum to give 2 as an off white solid (745 mg, 86%).

EXAMPLE 62

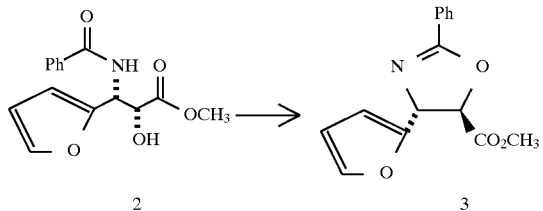

In an oven-dried, argon purged 25 ml flask equipped with a Dean-Stark trap, 2 (745 mg, 2.58 mmol) was dissolved in toluene (12 ml) and DMF (2.5 ml). PPTS (502 mg, 2.0 mmol) was added to this solution. The reaction mixture was heated to reflux with stirring for 28 hours. The mixture was diluted with ethyl acetated (50 ml) and was washed with H₂O (20 ml). The aqueous layer was extracted with ethyl acetate (50 ml). The combined organic fractions were dried over MgSO4, filtered, and concentrated in vacuo to give crude 3 product (630 mg, 77%) as a dark oil. Crude 3 was purified by column chromatography (silica gel, 2×12 cm, 10% ethyl acetate/hexane as eluant) to give 3 as a thick colorless oil (540 mg, 66%).

EXAMPLE 63

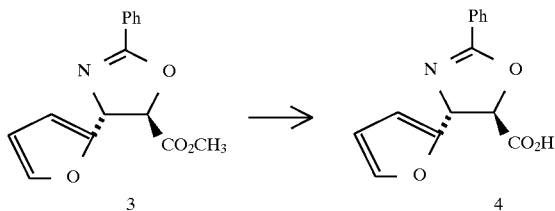

In a 25 ml flask, 3 (540 mg, 2.1 mmol) was dissolved in THF (6 ml) and H₂O (3 ml). To this solution was added solid LiOH (82 mg, 2.0 mmol) in one portion at room temperature. The resulting mixture was stirred for 0.5 hour at room temperature. The reaction was quenched by adding HCl (2.4 ml of a 1.0N solution) dropwise at room temperature. Next, the mixture was poured into H₂O (10 ml), extracted with CH₂Cl₂ (4×15 ml), dried over MgSO₄, filtered and concentrated in vacuo to give crude 4 (420 mg, 82%) as a yellow oil which was used directly in the next step without further purification.

EXAMPLE 64

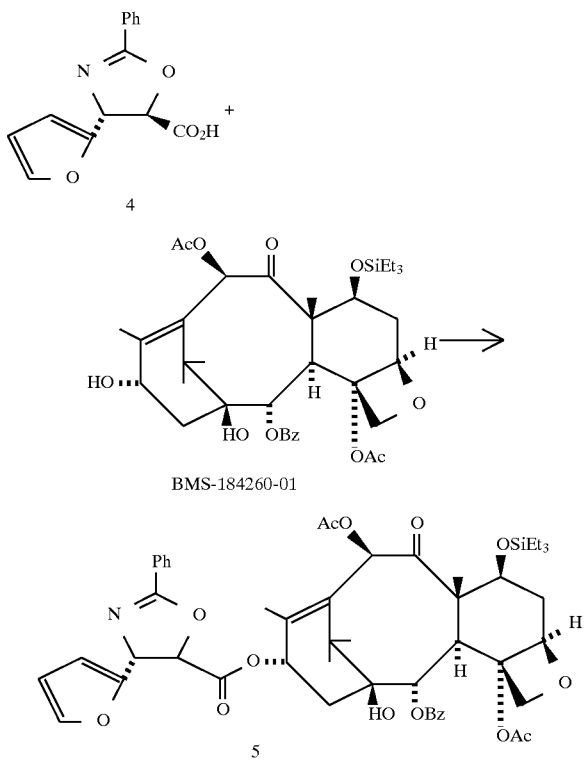

In an oven-dried, argon purged 25 ml flask, 4 (140 mg, 0.54 mmol), BMS-184260-01 (346 mg, 0.495 mmol) and N,N-dimethyl-aminopyridine (66 mg, 0.54 mmol) were suspended in toluene (10 ml) at room temperature. After stirring the suspension for 20 minutes, 1,3-dicyclohexylcarbodiimide (DCC) (111 mg, 0.54 mmol) was added in one portion and the mixture was stirred at room temperature for 2 hours. Next, N,N-dimethylaminopyridine (66 mg, 0.54 mmol) and 1,3-dicyclohexylcarbodiimide (DCC) (111 mg, 0.54 mmol) were added to the reaction mixture. The reaction mixture was stirred for 14 hours. The mixture was poured into sat. NH₄Cl (20 ml) and extracted with ethyl acetate (100 ml). The organic extract was filtered through Celite, and the Celite pad was then rinsed with ethyl acetate (4×50 ml). The combined organic layers were dried over MgSO₄, filtered and concentrated in vacuo to give crude 5 (582 mg, 125%). The crude product was purified by column chromatography (silica gel, 2×12 cm, 5% ethyl acetate/hexane as eluant) to give 5 (413 mg, 89%) as a colorless oil.

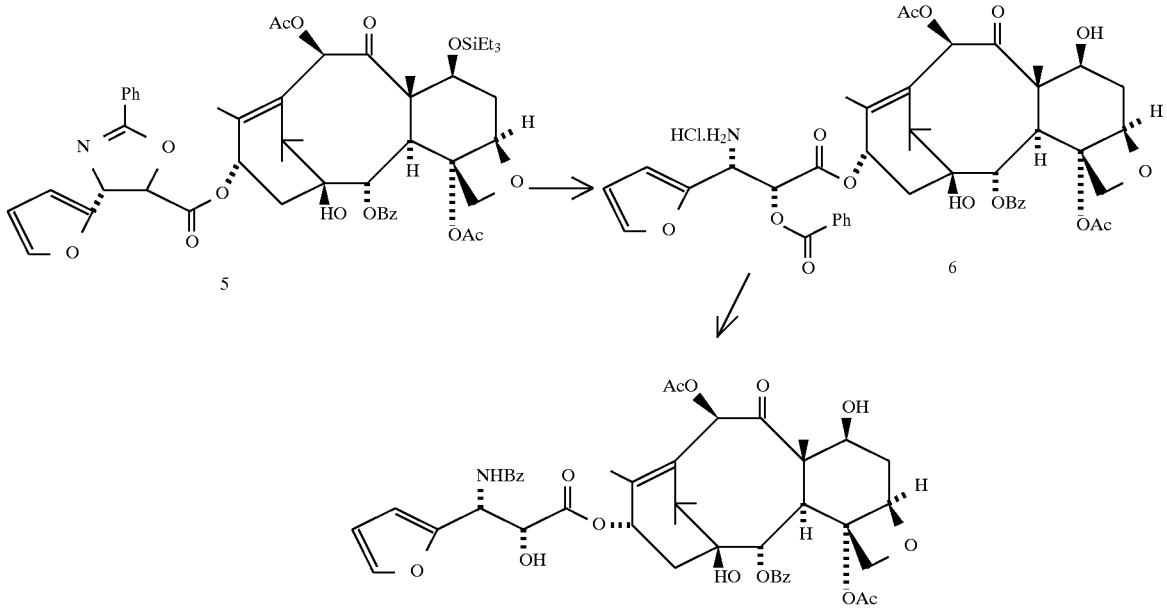

EXAMPLE 65

In an oven-dried, argon purged 25 ml flask, 5 (92 mg, 0.094 mmol) was dissolved in THF (2.0 ml) and methanol (2.0 ml). To this flask was added aqueous HCl (0.5 ml of a 2.0N solution) at 0° C. The solution was then placed in a 6° C. cold bath for 14 hours. The reaction mixture was warmed to room temperature and to this flask was added saturated NaHCO$_3$ (5.0 ml). The reaction mixture was stirred for 3 hours at room temperature. The mixture was poured into H$_2$O (10 ml) and extracted with CH$_2$Cl$_2$ (4×20 ml). The combined organic fractions were dried over MgSO$_4$, filtered, and concentrated in vacuo to give crude product (70 mg) as a white solid. To a hot solution of the crude product dissolved in CH$_3$OH (3.0 ml), H$_2$O (~1.0 ml) was added till the solution became cloudy. The solution was cooled in a refrigerator over night. The white solid was filtered off using a medium fitted glass filter and dried under high vacuum to give end product (51 mg, 64%) as a white solid.

EXAMPLE 66

Preparation of C-4 Cyclopropyl ester-7-TES baccatin with a C-1 3(Oxayolyl-furyl)side chain

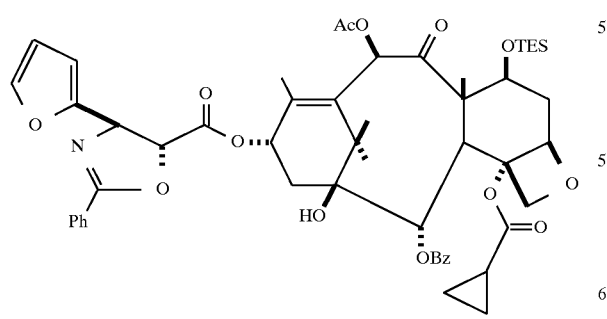

To a toluene (2.5 mL) suspension of the product of Example 22 (92.3 mg, 0.127 mmol) and the product of Example 63 (36.0 mg, 0.140 mmol) at room temperature was added DMAP (17.1 mg, 0.140 mmol). After 10 minutes, DCC (28.8 mg, 0.140 mmol) was also added. After 2 hours at room temperature, second dose of reagents were added. The reaction was stirred overnight at room temperature. Then this reaction mixture was filtered and rinsed with EtOAc. The organic layer was concentrated in vacuo. The residue was chromatographed (30% EtOAc/Hexanes) to afford desired product (125 mg) in 100% yield.

$^1$H NMR (CDCl$_3$): δ8.20–7.80 (m, 4H), 7.62–7.39 (m, 7H), 6.38 (m, 3H), 6.08 (m, 1H), 5.67 (m, 2H), 5.20 (d, J=5.9 Hz, 1H), 5.20 (d, J=5.9 Hz,1H), 4.88 (d, J=9.2 Hz, 1H), 4.49 (dd, J=6.6 Hz, J' =10.2 Hz, 1H), 4.16 (AB q, J=8.4 Hz, 2H), 3.86 (d, J=6.8 Hz, 1H), 2.54–0.52 (m, 39H, incl. singlets at 2.14, 2.03, 1.67, 1.21, 1.15, 3H each, triplet at 0.91, 9H).

HRMS calcd. for C$_{53}$H$_{64}$NO$_{14}$Si (MH$^+$): 966.4096, found: 966.4134.

EXAMPLE 67

Preparation of C-4 Cyclopropyl ester taxane with a furyl side chain

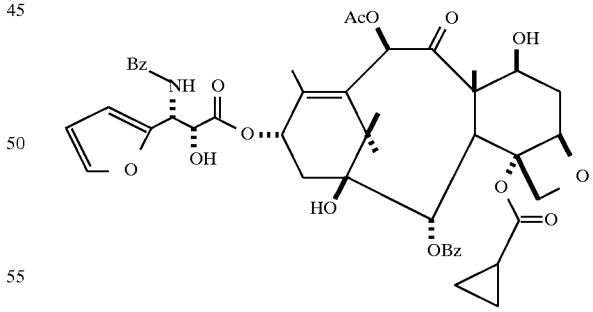

The compound of Example 66 (69 mg, 0.0715 mmol) was dissolved in THF (1.4 mL) and MeOH (1.4 mL). This solution was then treated at 0° C. with 1N HCl (0.716 mL). After 17 hours at 4° C., the reaction mixture was warmed to room temperature and treated with NaHCO$_3$ saturated solution (6.5 mL). After 6 hours at room temperature, the reaction mixture was extracted with EtOAc (4×20 mL). The combined organic layer was conc. in vacuo. The residue was chromatographed (60% EtOAc/Hexanes) to afford desired product (37.4 mg) in 60% yield.

¹H NMR (CDCl₃): δ8.12–8.09 (m, 2H), 7.74–7.26 (m, 7H), 6.85 (d, J=9.3 Hz, 1H), 6.39 (s, 2H), 6.30 (s, 1H), 6.20 (m, 1H), 5.93 (d, J=9.3 Hz, 1H), 5.67 (d, J=7.0 Hz, 1H), 4.88 (s, 1H), 4.82 (d, J=7.7 Hz, 1H), 4.42 (m, 1H 4.20 (AB q, J=8.5 Hz, 2H), 3.85 (d, J=6.8 Hz, 1H), 2.54–0.88 (m, 24H, incl. singlets at 2.23, 1.88. 1.67, 1.24, 1.14, 3H each).

HRMS calcd. for C₄₇H₅₂NO₁₅ (MH⁺): 870.3337, found: 870.3307.

EXAMPLE 68

Preparation of C-4 Cyclopropyl ester-2' ethyl carbonate

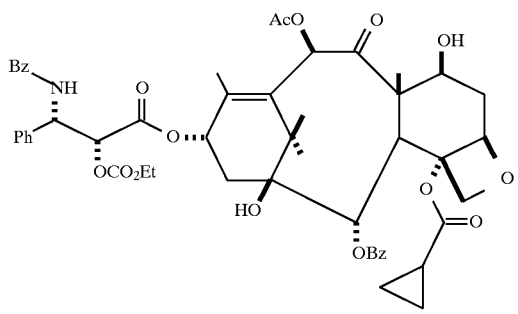

A dichloromethane solution (22.8 mL) of the product of Example 24 (1.333 g, 1.52 mmol) at 0° C. was added EtPr₂N (1.586 mL, 9.10 mmol), followed by EtOCOCl (0.87 mL, 9.10 mmol). The reaction was stirred at 0° C. for 6 hours. Then the reaction mixture was diluted with EtOAc (200 mL), washed with water (20 mL×3) and brine. The organic layer was dried and concentrated in vacuo. The residue was chromatographed (50% EtOAc/Hexanes) to afford desired product (1.281 g) in 88.8% yield together with 86 mg of the starting material (6.5%).

¹H NMR (CDCl₃): δ8.12–8.10 (m, 2H), 7.76–7.26 (m, 13H), 6.90 (d, J=9.4 Hz, 1H), 6.27 (m, 2H), 6.01 (dd, J=2.1 Hz, J' =9.3 Hz, 1H), 5.68 (d, J=7.0 Hz,m 1H), 5.55 (d, J=2.4 Hz, 1H), 4.83 (d, J=8.2 Hz, 1H), 4.44 (m, 1H), 4.23 (m, 4H), 3.83 (d, J=7.0 Hz, 1H), 2.53–0.87 (m, 27H, incl. singlets at 2.22, 1.95, 1.87, 1.67, 1.26, 3H each, triplet at 1.32, 3H).

HRMS calcd. for C₅₂H₅₈NO₁₆ (MH⁺): 952.3756, found: 952.3726.

EXAMPLE 69

Preparation of C-4 Cyclopropane-2'-ethyl carbonate-7 substituted precursor

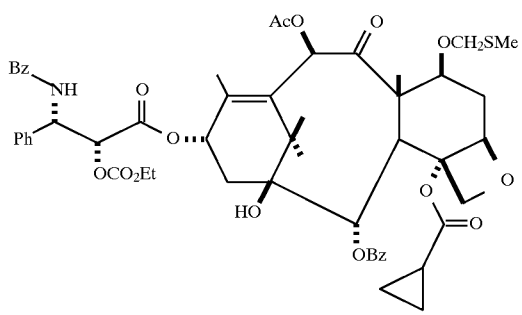

The 2' Ethyl carbonate of Example 68 (53 mg, 0.056 mmol) was dissolved in DMSO (0.5 mL), AC₂O (0.5 mL) was then added. The reaction was stirred at room temperature for 14 hours. The reaction mixture was diluted with EtOAc (50 mL), washed with water (5 mL×3), NaHCO3 saturated solution and brine. The organic layer was then dried and concentrated in vacuo. The residue was chromatographed (40% EtOAc/Hexanes) to afford 56.3 mg of the desired product in 100% yield.

¹H NMR (CDCl₃): δ8.10–8.07 (m, 2H), 7.76–7.26 (m, 13H), 6.90 (d, J=9.4 Hz, 1H), 6.56 (s, 1H), 6.23 (m, 1H), 6.03 (d, J=9.5 Hz, 1H), 5.70 (d, J=6.9 Hz, 1H), 5.58 (d, J=2.1 Hz, 1H), 4.84 (d, J=8.9 Hz, 1H), 4.66 (s, 2H), 4.21 (m, 5H), 3.91 (d, J=6.8 Hz. 1H), 2.80–0.87 (m, 30H, incl. singlets at 2.17, 2.12, 2.11, 1.75, 1.22, 1.20, 3H each, triplet at 1.32, 3H).

EXAMPLE 70

Preparation of C-4 Cyclopropane-2'-ethyl carbonate-7-phosphate precursor

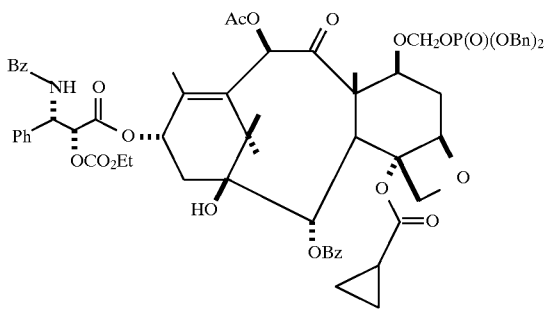

To a dichloromethane solution (25.7 mL) of the product of Example 69 (1.30 g, 1.286 mmol) was added 4A sieves (1.30 g), followed by a THF solution (25.7 mL) of NIS (434 mg, 1.929 mmol) and dibenzyl phosphate (537 mg, 1.929 mmol). The reaction mixture was stirred at room temperature, for 5 hours. Then the reaction mixture was filtered through Celite and rinsed with EtOAc. The solvent was removed, and the residue was dissolved in EtOAc (200 mL), washed with 1% NaHSO₃, brine, and dried over MgSO₄. The organic phase was concentrated in vacuo. The residue was chromatographed (50% EtOAc/Hexanes) to afford 1.278 g of product in 80. 1% yield.

¹H NMR (CDCl₃): δ8.10–8.07 (m, 2H), 7.76–7.26 (m, 23H), 6.90 (d, J=9.4 Hz, 1H), 6.35 (s, 1H), 6.23 (m, 1H), 6.02 (d, J=9.5 Hz, 1H), 5.68 (d, J=6.8 Hz, 1H), 5.56 (s, 1H), 5.40 (m, 1H), 5.04 (m, 4H), 4.75 (d, J=9.0 Hz, 1H), 4.20 (m, 5H), 3.89 (d, J=6.8 Hz, 1H), 2.78–0.86 (m, 27H, incl. singlets at 2.18, 1.99, 1.67, 1.18, 1.05, 3H each, triplet at 1.31, 3H).

EXAMPLE 71

Preparation of C-4 Cyclopropane-2'-ethyl carbonate-7-phosphate

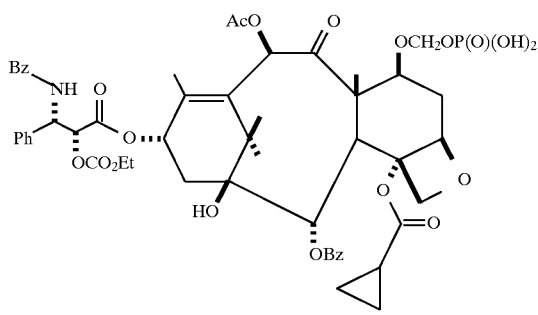

Compound of Example 70 (1.278 g, 1.03 mmol) was dissolved in dry EtOAc (41.2 mL). To this solution was added catalyst Pd/C (438 mg, 10%, 0.412 mmol). The reaction mixture was hydrogenated under 50 Psi for 12 hours. The reaction mixture was then filtered and concentrated in vacuo to give 1.08 g of crude product in 100% yield.

The crude product was carried on for next step without further characterization.

EXAMPLE 72

Preparation of C-4 Cyclopropane-2'-ethyl carbonate-7-phosphate triethanolamine salt

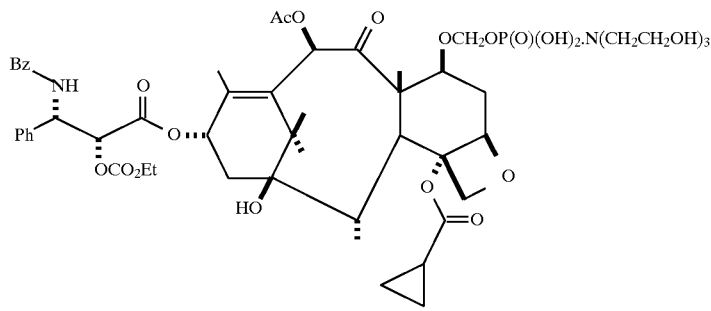

To a EtOAc solution (6.8 mL) of the product of Example 71 (1.08 g, 1.02 mmol) was added a 0.100M solution of triethanolamine (6.8 mL, 0.15M) in EtOAc. The resulting mixture was placed in −20° C. overnight. The mixture was then filtered, the solid was washed with cooled 10% EtOAc/Hexane and dried under vacuum for 12 hours to afford the desired prodrug (1.00 g) in 81.2% yield. The purity of the end product was determined (by HPLC) to be >97% pure.

$^1$H NMR (CD$_3$OD): δ8.10–8.07 (m, 2H), 7.80–7.26 (m, 14H), 6.38 (s, 1H), 6.07 (m, 1H), 5.89 (d, J=5.2 Hz, 1H), 5.63 (d, J=7.0 Hz, 1H), 5.55 (d, J=5.2 Hz, 1H), 5.22 (m, 1H), 4.87 (m, 2H), 4.23 (m, 5H), 3.88 (d, J=7.0 Hz, 1H), 3.80 (m, 6H), 3.30 (m, 1H), 3.18 (m, 6H), 2.97–0.86 (m, 26H, incl. singlets at 2.15, 1.94, 1.69, 1.57, 1.13, 3H each, triplet at 1.30, 3H).

HRMS calcd. for C$_{53}$H$_{61}$NO$_{20}$P (MH$^+$, M=acid): 1062.3525, found: 1062.3550.

EXAMPLE 73

Preparation of 7-TES-13-TMS Baccatin

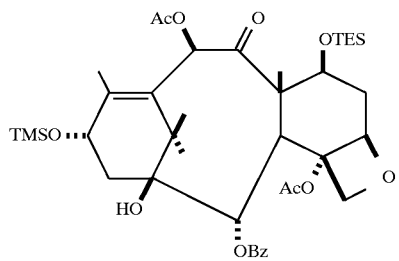

7-TES baccatin of Example 10 (1.895 g, 2.707 mmol) was dissolved in dry DMF (10.8 mL). To this solution at 0° C. was added imidazole (736.4 mg, 10.83 mmol), followed by TMSCl (1.37 mL, 10.83 mmol). The reaction was stirred at 0° C. for 1.5 hours. The reaction mixture was then diluted with EtOAc (400 mL), and washed with water (20 mL×3), brine (15 mL). The organic layer was then dried and concentrated in vacuo. The residue was chromatographed (20% EtOAc/Hexanes) to afford 1.881 g (90%) of desired product.

EXAMPLE 74

Preparation of 7-TES-13-TMS-1-DMS Baccatin

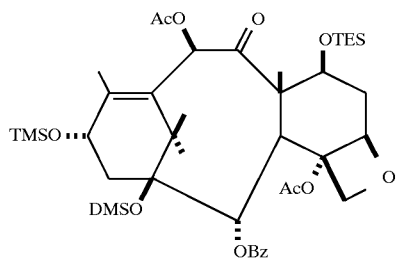

7-TES-13-TMS baccatin of Example 73 (305 mg, 0.430 mmol) was dissolved in dry DMF (2 mL). To this solution at 0° C. was added imidazole (87.6 mg, 1.289 mmol), followed by chlorodimethylsilane (122 mg, 1.289 mmol). After 1 hour, the reaction mixture was diluted with EtOAc (150 mL), washed with water (10 mL×3) and brine (10 mL). The resulting organic layer was dried and concentrated in vacuo. The residue was chromatographed (10% EtOAc/Hexanes) to afford 305 mg (92.4%) of the desired product.

EXAMPLE 75

Preparation of 7-TES-13-TMS-1-DMS-C-4 Hydroxy Baccatin

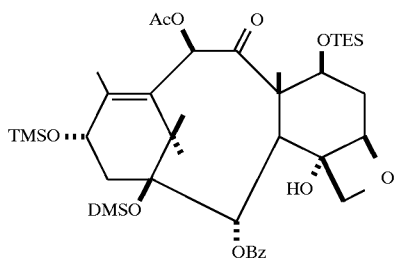

1-DMS-7-TES-13-TMS baccatin of Example 74 was dissolved in dry THF (8 mL). To this solution at 0° C. was added Red-Al (0.314 mL, 60%, 1.61 mmol). The mixture was stirred at 0° C. for 40 minutes, the reaction was then quenched with saturated solution of sodium tartrate (1 mL) for 2 minutes. The reaction mixture was extracted with EtOAc (150 mL), washed with water (15 mL×2) and brine (15 mL). The organic layer was dried and concentrated in vacuo. The residue was chromatographed (10–20% EtOAc/Hexanes) to afford 143.8 mg (45.3%) of desired product.

NMR (300 MHz, CDCl$_3$): d 8.10–8.06 (m, 2H), 7.55–7.39 (m, 3H), 6.39 (s, 1H), 5.59 (d, J=5.5 Hz, 1H), 4.68 (dd, J1=3.9 Hz, J2=9.6 Hz, 1H), 4.61 (m, 1H), 4.53 (m, 1H), 4.21 (AB q, J=7.8 Hz, 2H), 4.03 (dd, J1=6.1 Hz, J2=11.6 Hz, 1H), 3.74 (s, 1H), 3.48 (d, J=5.7 Hz, 1H), 2.74–0.48 (m, 34H, incl. singlets at 2.15, 2.06, 1.54, 1.16, 0.92, 3H each), 0.28 (s, 9H), –0.015 & –0.32 (doublets, 3H each)

EXAMPLE 76

Preparation of 7-TES-13-TMS-1-DMS-C-4-[OC(O)CH=CH$_2$] Baccatin

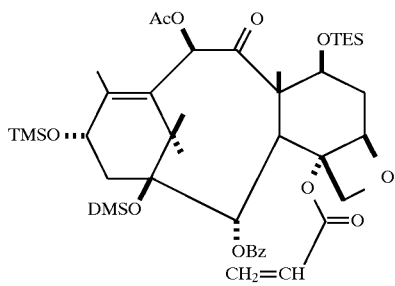

The compound of Example 75 (99 mg, 0.125 mmol) was dissolved in dry THF (2.5 mL). To this solution at 0° C. was added LHMDS (0.150 mL, 1M, 0.150 mmol). After 30 minutes, acryloyl chloride (0.0153 mL, 0.188 mmol) was added. After another 30 minutes, the reaction was quenched with NH4Cl saturated solution. The reaction mixture was extracted with EtOAc (100 mL), and washed with water (10 mL×2) and brine (10 mL). The organic phase was dried and concentrated in vacuo. The residue was chromatographed (5–10% EtOAc/Hexanes) to afford 57.5 mg (54.6%) of desired product.

EXAMPLE 77

Preparation of C-4[OC(O)CH=CH$_2$] Baccatin

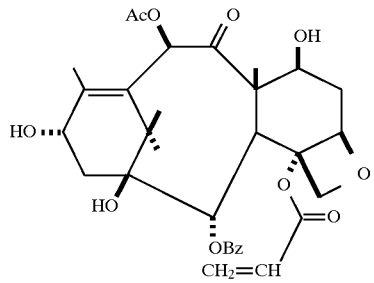

The compound of Example 76 (105 mg, 0.125 mmol) was dissolved in CH3CN (2.5 mL). To this solution at 0° C. was added pyridine (0.374 mL), followed by 48% HF (1.12 mL). The reaction was kept at 4° C. overnight. The reaction was then diluted with EtOAc (75 mL). The organic layer was washed with 1N HCl (5 mL), NaHCO3 saturated solution (5 mL×3) and brine. The organic phase was then dried and concentrated in vacuo. The residue was chromatographed (60% EtOAc/Hexanes) to afford 60.6 mg (81.3%) of desired product.

EXAMPLE 78

Preparation of 7-TES-C-4[OC(O)CH=CH$_2$] Baccatin

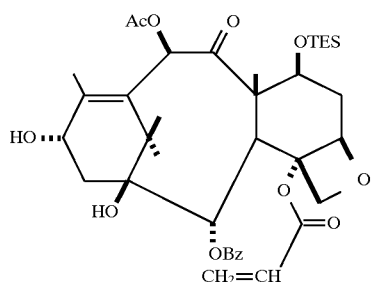

The triol of Example 77 (60.0 mg, 0.100 mmol) was dissolved in dry DMF (0.66 mL). To this solution at 0° C. was added imidazole (27.2 mg, 0.400 mmol), followed by TESCl (0.0672 mL, 0.400 mmol). After 30 minutes, the reaction was diluted with EtOAc (75 mL), washed with water (5 mL×3) and brine. The organic layer was then dried and concentrated in vacuo. The residue was chromatographed (40% EtOAc/Hexanes) to afford 56.0 mg (78.4%) of desired product.

EXAMPLE 79

Preparation of 2',7-Bis TES-4-[OC(O)CH=CH$_2$] Paclitaxel

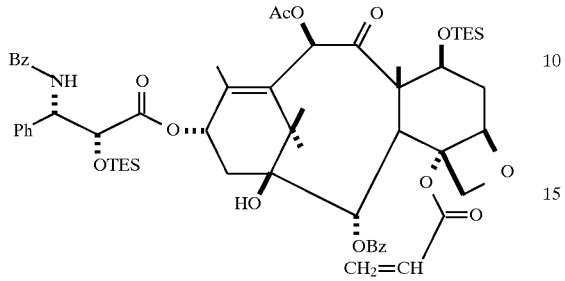

The baccatin of Example 78 (50 mg, 0.0702 mmol) was dissolved in THF (1.4 mL). To this solution at −40° C. was added LHMDS (0.0843 mL, 1M, 0.0843 mmol), followed immediately by a THF (0.7 mL) solution of β-lactam of Example 23 (40.1 mg, 0.105 mmol). After 2 minutes at −40° C., the reaction was stirred at 0° C. for 1 hour. The reaction was then quenched with NH4Cl saturated solution. The reaction mixture was extracted with EtOAc, and washed water. The organic layer was dried and concentrated in vacuo. The residue was chromatographed (20–30% EtOAc/Hexanes) to afford 66 mg (86%) of the desired product.

EXAMPLE 80

Preparation of C-4[OC(O)CH=CH$_2$] Paclitaxel

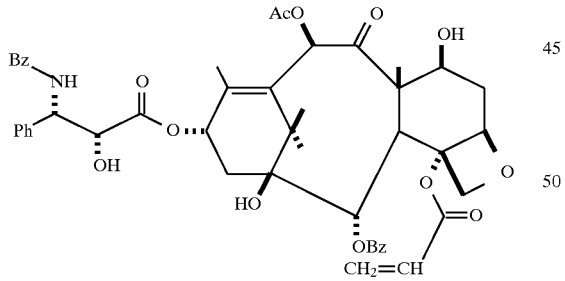

The compound of Example 79 (46mg, 0.0421 mmol) was dissolved in CH3CN (0.85 mL). To this solution at 0° C. was added pyridine (0.125 mL), followed by 48% HF (0.375 mL). The reaction was kept at 4° C. overnight. The reaction mixture was then diluted with EtOAc (40 mL), washed with 1N HCl (3 mL), NaHCO3 saturated solution (3 mL×3). The organic layer was dried and concentrated in vacuo. The residue was chromatographed (70% EtOAc/Hexanes) to afford 28 mg (76.9%) of the desired product.

EXAMPLE 81

Preparation of 7.13-Sis-TES-1-DMS-C-4-[C(O)C$_6$H$_5$] Baccatin

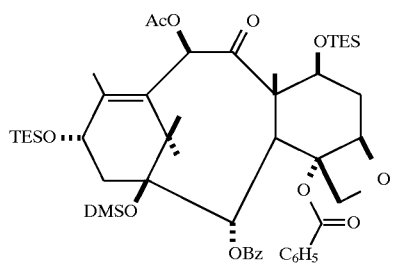

The compound of Example 19 (279 mg, 0.336 mmol) was dissolved in dry THF (7 mL). To this solution at 0° C. was added LHMDS (0.403 mL, 1M, 0.403 mmol). After 30 minutes, benzoyl chloride (0.0585 mL, 0.504 mmol) was added. After 30 minutes, the reaction was quenched with NH4Cl saturated solution. The reaction mixture was extracted with EtOAc (150 mL). The organic layer was washed with water and brine and dried and concentrated in vacuo. The residue was chromatographed (10% EtOAc/Hexanes) to afford 215.5 mg (68.6%) of the desired product.

EXAMPLE 82

Preparation of C-4-Benzoyl Baccatin

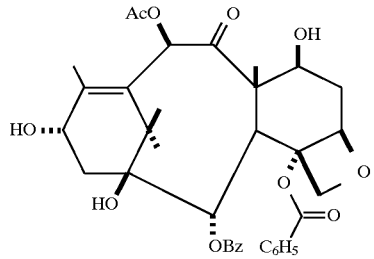

The compound of Example 81 (161 mg, 0.172 mmol) was dissolved in CH3CN. To this solution at 0° C. was added pyridine (0.57 mL), followed by 48% HF (1.80 mL). After 5 hours at 4° C., another dose of reagent was added. The reaction was kept at 4° C. overnight. The reaction mixture was then diluted with EtOAc (100 mL), and washed with 1N HCl (5 mL), NaHCO3 (5 mL×3). The organic phase was dried and concentrated in vacuo. The residue thus obtained was chromatographed (30–50% EtOAc/Hexanes) to afford 48 mg (43.0%) of the desired end product.

EXAMPLE 83

Preparation of 7-TES-C-4-Benzoyl Baccatin

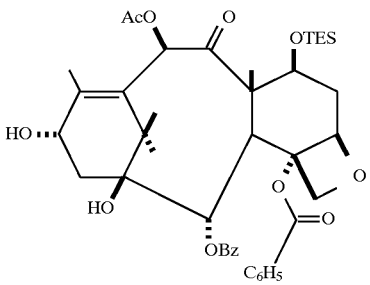

The triol of Example 82 (48.0 mg, 0.074 mmol) was dissolved in DMF (0.40 mL). To this solution at 0° C. was added imidazole (20.1 mg, 0.296 mmol), followed by TESCl (0.0496 mL, 0.296 mmol). After 30 minutes, the reaction mixture was diluted with EtOAc (45 mL), and washed with water (1mL×3) and brine. The organic phase was dried and concentrated in vacuo. The residue was chromatographed (40% EtOAc/Hexanes) to afford 48 mg (85.0%) of the desired end product.

EXAMPLE 84

Preparation of C-4-Benzoyl Paclitaxel

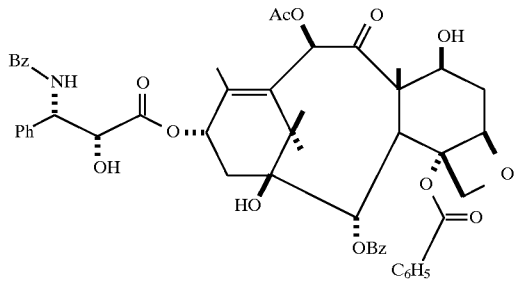

The compound of Example 83 (364.6 mg, 0.478 mmol) was dissolved in THF (9.6 mL). To this solution at −40° C. was added LHMDS (0.718 mL, 1M, 0.718 mmol), followed by β-lactam of Example 23 (273.5 mg, 0.718 mmol). Following the same procedure as in previous examples, 415 mg (75.9%) of compound was obtained. Thereafter the deprotected paclitaxel analogue may be obtained by dissolving the above compound in $CH_3CN$ (16.5 mL) and at 0° C. adding pyridine (0.36 mL) followed by 48% HF (3.0 mL). Following the steps outlined in Example 80, the paclitaxel analogue is obtained in 315 mg (94.8%) yield.

EXAMPLE 85

Preparation of 4-Cyclobutane taxane with fury side chain

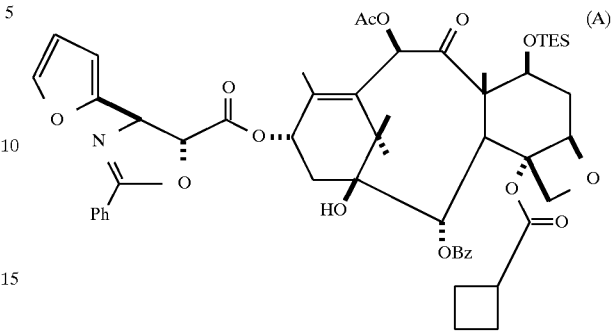

7-TES-4-cyclobutyl baccatin of Example 27 (154 mg, 0.208 mmol) was dissolved in dry toluene (4 mL). To this solution at room temperature was added free acid of Example 63 (64.2 mg, 0.250 mmol) and DMAP (30.5 mg, 0.250 mmol). After 10 minutes, DCC (51.4 mg, 0.250 mmol) was added. The reaction was stirred for 2 hours, and at this time another dose of DCC/DMAP was added. The reaction was further stirred for 12 hours. The reaction mixture was then filtered through Celite, and the "cake" was rinsed with EtOAc. The combined organic layer was concentrated in vacuo, and the residue was chromatographed (30–40% ethyl acetate in hexanes) to afford 222 mg (100%) of the desired product.

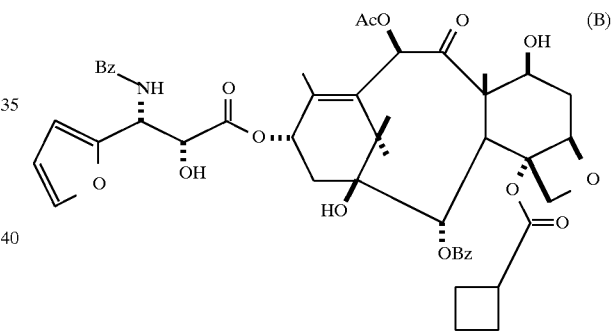

A THF (2 mL) and MeOH (2 mL) solution of (A) (182 mg, 0.186 mmol) was treated at 0° C. with 1N HCl (1.86 mL). After 1hour at 0° C., the reaction was kept at 4° C. overnight. The reaction mixture was then treated with saturated $NaHCO_3$ (9.6 mL). After 5 hours at room temperature, the reaction mixture was diluted with EtOAc (120 mL), and washed with water (4×10 mL). The organic layer was then dried with $MgSO_4$, and concentrated in vacuo. The residue was chromatographed (40–60% ethyl acetate in hexanes) to afford 77 mg (47%) of the desired product.

$^1$H NMR ($CDCl_3$): 8.15–8.12 (m, 2H), 7.73–7.35 (m, 9H), 6.87 (d, J=9.2 Hz, 1H), 6.44 (m, 2H), 6.28 (s, 1H), 6.20 (m, 1H), 5.89 (d, J=9.2 Hz, 1H), 5.66 (d, J=7.1 Hz, 1H), 4.90 (d, J=8.1 Hz, 1H), 4.85 (s, 1H), 4.44 (m, 1H), 4.27 (AB q, J=8.4 Hz, 2H), 3.80 (d, J=7.0 Hz, 1H), 3.56 (m, 1H), 2.61–0.92 (m, 25H, incl. singlets at 2.22, 1.83, 1.69, 1.23, 1.13 3H each). $^{13}$C NMR ($CDCl_3$): 203.6, 174.4, 172.4, 171.2, 166.9, 166.8, 150.9, 142.5, 142.0, 133.5, 133.3, 132.9, 131.9, 130.1, 130.0, 129.7, 129.0, 128.5, 127.0, 110.8, 108.0, 84.6, 80.8, 78.9, 76.4, 75.4 75.0, 72.5, 72.0, 71.3, 58.5, 50.1, 45.6, 43.1, 38.8, 35.6, 35.5, 26.7, 25.3, 25.1, 21.9, 20.7, 18.2, 14.6, 9.5.

HRMS calcd. for $C_{48}H_{54}NO_{15}$ ($MH^+$): 884.3493, found: 884.3472.

EXAMPLE 86

Preparation of Paclitaxel

The compound of Example 10(b) was added to a 5 ml flask and dissolved in THF. Methanol was added and the slightly yellowish homogeneous solution was cooled to 0° C. HCl was added and the resulting homogeneous solution was stirred at 0° C. for ½ hour and then transferred to a 4° C. cold room. After 19½ hours from the addition of HCl, TLC showed no starting material. The reaction solution was added to a flask containing 20 ml of ½ saturated solution of NaCl. The resulting heterogeneous mixture was stirred at room temperature for 45 minutes. The mixture was filtered and the solid was washed with 15 ml of $H_2O$ and air-dried on the fitted funnel. The white solid was then washed through the frit by dissolution in THF into another flask and concentrated to give 0.169 gr. of a glassy solid. The material was transferred to a vial and dissolved in 1.0 ml of THF. $NEt_3$ (4 eq.; 0.63 mmoles; 88 ml) was added, a precipitate formed. The heterogeneous mixture was stirred at room temperature. TLC showed the reaction to be essentially complete after 4.25 hours after the addition of $NEt_3$. The mixture was diluted with 5 ml EtOAc and 5 ml of $H_2O$ and shaken. The layers were separated. The aqueous fraction was extracted twice with 5 ml EtOAc. The combined organic fractions were washed with 5 ml of HCl (in), 5 ml of saturated aqueous NaCl, dried over $Na_2SO_4$, filtered and concentrated to give 0.127 gr. of a white solid (paclitaxel) in 93.9% yield.

What is claimed is:

1. The compound of the formula

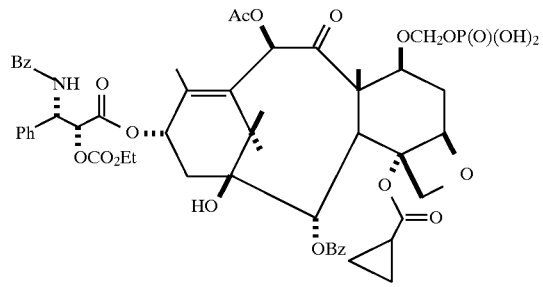

2. The compound of the formula

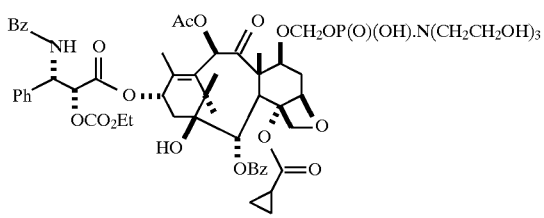

* * * * *